(12) United States Patent
Chang

(10) Patent No.: US 10,201,692 B2
(45) Date of Patent: Feb. 12, 2019

(54) SOLUTION DELIVERY DEVICE AND METHOD

(71) Applicant: Byeong Seon Chang, Sherman Oaks, CA (US)

(72) Inventor: Byeong Seon Chang, Sherman Oaks, CA (US)

(*) Notice: Subject to any disclaimer, the term of this patent is extended or adjusted under 35 U.S.C. 154(b) by 587 days.

(21) Appl. No.: 14/848,062

(22) Filed: Sep. 8, 2015

(65) Prior Publication Data

US 2016/0067144 A1 Mar. 10, 2016

Related U.S. Application Data

(60) Provisional application No. 62/048,089, filed on Sep. 9, 2014.

(51) Int. Cl.
*A61M 39/10* (2006.01)
*A61M 5/24* (2006.01)
(Continued)

(52) U.S. Cl.
CPC .......... *A61M 39/10* (2013.01); *A61M 5/1407* (2013.01); *A61M 5/1409* (2013.01);
(Continued)

(58) Field of Classification Search
CPC .............. A61M 5/1407; A61M 5/1409; A61M 5/2448; A61M 5/284; A61M 39/10; A61M 39/1011
See application file for complete search history.

(56) References Cited

U.S. PATENT DOCUMENTS

| | | |
|---|---|---|
| 2,708,438 A | 5/1955 | Cohen |
| 3,330,280 A | 7/1967 | Ogle |

(Continued)

FOREIGN PATENT DOCUMENTS

| | | |
|---|---|---|
| EP | 298585 A1 | 1/1989 |
| EP | 664136 A2 | 7/1995 |
| WO | 2001026718 A1 | 4/2001 |
| WO | 2006073505 A2 | 7/2006 |

(Continued)

OTHER PUBLICATIONS

PCT International Preliminary Report on Patentability, PCT/US2008/003065, pp. 6 (dated Sep. 15, 2009).

(Continued)

*Primary Examiner* — Nathan R Price
*Assistant Examiner* — Courtney Fredrickson
(74) *Attorney, Agent, or Firm* — Entralta P.C.; Justin G. Sanders; Peter D. Weinstein

(57) ABSTRACT

The present specification discloses a solution delivery device having a container component and a plug component configured for selective engagement with the container component. The container component has an internal cavity including an elongated mixing channel containing a first constituent, and the plug component provides an internal flow path configured for introduction of a second constituent into the mixing channel for mixing with the first constituent. The plug component may be inserted within the container component partially in a first operational mode and fully in a second operational mode. The first constituent may be a drug and the second constituent a diluent, such that the drug may be lyophilized with the device in the first operational mode and reconstituted with the device in the second operational mode. Multiple devices may be employed in tandem for the co-delivery of multiple constituents. The device may be included in a kit or installed within an injector.

29 Claims, 33 Drawing Sheets

(51) Int. Cl.
*A61M 5/14* (2006.01)
*A61M 5/28* (2006.01)
*A61M 5/19* (2006.01)
*A61M 5/20* (2006.01)
*A61M 5/32* (2006.01)

(52) U.S. Cl.
CPC ............ *A61M 5/19* (2013.01); *A61M 5/2033* (2013.01); *A61M 5/2066* (2013.01); *A61M 5/2448* (2013.01); *A61M 5/284* (2013.01); *A61M 5/3293* (2013.01); *A61M 5/3294* (2013.01); *A61M 5/288* (2013.01); *A61M 2005/2013* (2013.01)

(56) References Cited

U.S. PATENT DOCUMENTS

| | | |
|---|---|---|
| 3,342,180 A | 9/1967 | Sandhage et al. |
| 3,477,432 A | 11/1969 | Shaw |
| 3,678,931 A | 7/1972 | Cohen |
| 3,685,514 A | 8/1972 | Cheney |
| 3,739,947 A | 6/1973 | Baumann et al. |
| 3,766,917 A | 10/1973 | Wimmer |
| 3,826,260 A | 7/1974 | Killinger |
| 3,838,689 A | 10/1974 | Cohen |
| 4,041,945 A | 8/1977 | Guiney |
| 4,153,186 A | 5/1979 | Nye |
| 4,172,457 A | 10/1979 | Choksi et al. |
| 4,318,386 A | 3/1982 | Showalter et al. |
| 4,328,802 A | 5/1982 | Curley et al. |
| 4,410,321 A | 10/1983 | Pearson et al. |
| 4,411,662 A | 10/1983 | Pearson |
| 4,432,755 A | 2/1984 | Pearson |
| 4,458,733 A | 7/1984 | Lyons |
| 4,563,174 A | 1/1986 | Dupont |
| 4,610,669 A | 9/1986 | Meyer et al. |
| 4,872,867 A | 10/1989 | Joh |
| 4,886,495 A | 12/1989 | Reynolds |
| 4,898,209 A | 2/1990 | Zbed |
| 5,080,649 A | 1/1992 | Vetter |
| 5,429,603 A | 7/1995 | Morris |
| 5,435,076 A | 7/1995 | Hjertman et al. |
| 5,472,422 A | 12/1995 | Ljungquist |
| 5,489,266 A | 2/1996 | Grimard |
| 5,549,561 A | 8/1996 | Hjertman |
| 5,569,193 A | 10/1996 | Hofstetter et al. |
| 5,685,846 A | 11/1997 | Michaels, Jr. |
| 5,716,339 A | 2/1998 | Tanaka et al. |
| 5,752,940 A | 5/1998 | Grimard |
| 5,779,668 A | 7/1998 | Grabenkort |
| 5,785,682 A | 7/1998 | Grabenkort |
| 5,817,055 A | 10/1998 | Ljungquist |
| 5,833,653 A | 11/1998 | Vetter et al. |
| 5,876,372 A | 3/1999 | Grabenkort et al. |
| 5,899,881 A | 5/1999 | Grimard et al. |
| 5,950,819 A | 9/1999 | Sellars |
| 6,149,628 A | 11/2000 | Szapiro et al. |
| 6,152,897 A | 11/2000 | Limrell et al. |
| 6,319,225 B1 | 11/2001 | Sugita et al. |
| 6,386,872 B1 | 5/2002 | Mukasa et al. |
| 6,406,455 B1 | 6/2002 | Willis et al. |
| 6,419,656 B1 | 7/2002 | Vetter et al. |
| 6,440,101 B1 | 8/2002 | Grabenkort et al. |
| 6,514,231 B1 | 2/2003 | Szapiro et al. |
| 6,547,755 B1 | 4/2003 | Lippe et al. |
| 6,692,468 B1 | 2/2004 | Waldenburg |
| 6,752,292 B2 | 6/2004 | Van Herpen |
| 6,808,511 B2 | 10/2004 | Pond |
| 6,817,987 B2 | 11/2004 | Vetter et al. |
| 6,846,300 B2 | 1/2005 | Horth et al. |
| 6,852,103 B2 | 2/2005 | Fowles et al. |
| 6,902,543 B1 | 6/2005 | Cherif-Cheikh et al. |
| 7,959,600 B2 | 6/2011 | Chang et al. |
| 7,963,937 B2 | 6/2011 | Pauser et al. |
| 2002/0068896 A1 | 6/2002 | Robinson et al. |
| 2002/0198490 A1 | 12/2002 | Wirt et al. |
| 2003/0176834 A1 | 9/2003 | Horth et al. |
| 2003/0187388 A1 | 10/2003 | Sharon et al. |
| 2005/0096588 A1 | 5/2005 | Hagmann et al. |
| 2005/0137566 A1 | 6/2005 | Fowles et al. |
| 2005/0263615 A1 | 12/2005 | Kriesel et al. |
| 2006/0052747 A1 | 3/2006 | Nishimura et al. |
| 2006/0100587 A1 | 5/2006 | Bertron et al. |
| 2006/0144869 A1 | 7/2006 | Chang et al. |
| 2006/0157507 A1 | 7/2006 | Chang et al. |
| 2007/0225640 A1 | 9/2007 | Chang et al. |
| 2008/0195082 A1 | 8/2008 | Pauser et al. |
| 2008/0228163 A1 | 9/2008 | Smith |
| 2011/0288531 A1 | 11/2011 | Chang |
| 2012/0104045 A1* | 5/2012 | Chang ................ A61M 5/2448 222/145.5 |
| 2013/0319885 A1 | 12/2013 | Chang |

FOREIGN PATENT DOCUMENTS

| | | |
|---|---|---|
| WO | 2008112155 A1 | 9/2008 |
| WO | 2010139669 A1 | 12/2010 |
| WO | 2012097007 A2 | 7/2012 |

OTHER PUBLICATIONS

PCT International Preliminary Report on Patentability, PCT/US2005/028035, pp. 6 (dated Jul. 3, 2007).
PCT International Preliminary Report on Patentability, PCT/US2012/020838, pp. 4 (dated Jul. 10, 2013).
Written Opinion of the International Searching Authority for PCT/US2015/04902, dated Dec. 4, 2015.
International Search Report, PCT/US2005/028035, dated Sep. 26, 2006.
International Search Report, PCT/US2008/003065, dated Jun. 10, 2008.
International Search Report, PCT/US2012/020838, dated Jul. 30, 2012.
International Search Report, PCT/US2015/049002, dated Dec. 4, 2015.

* cited by examiner

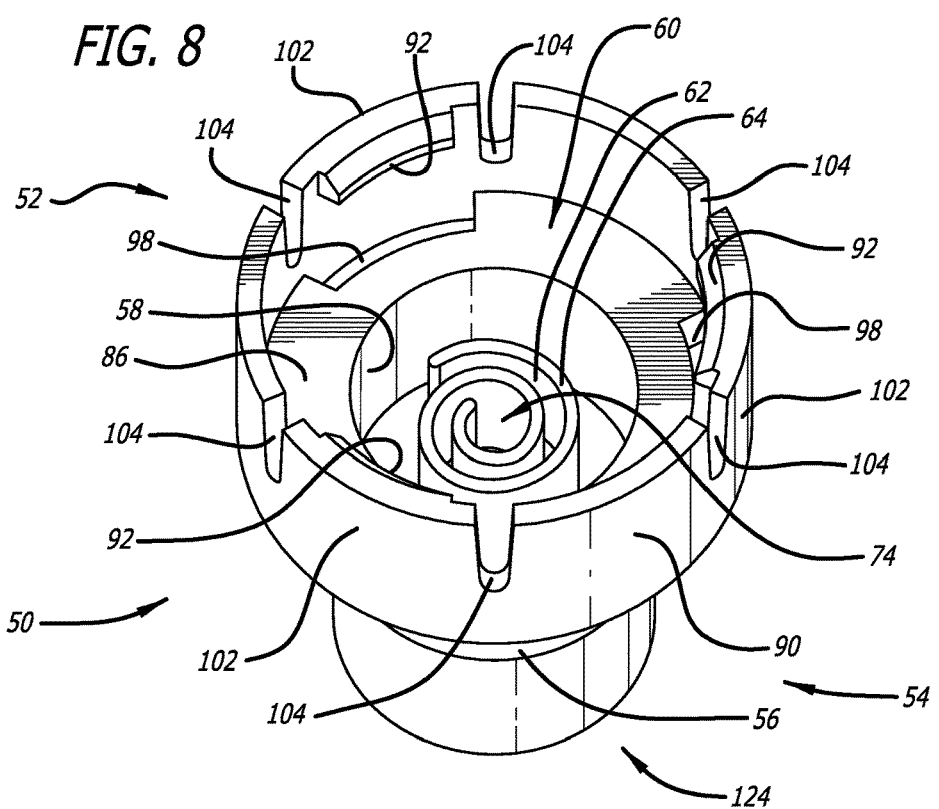
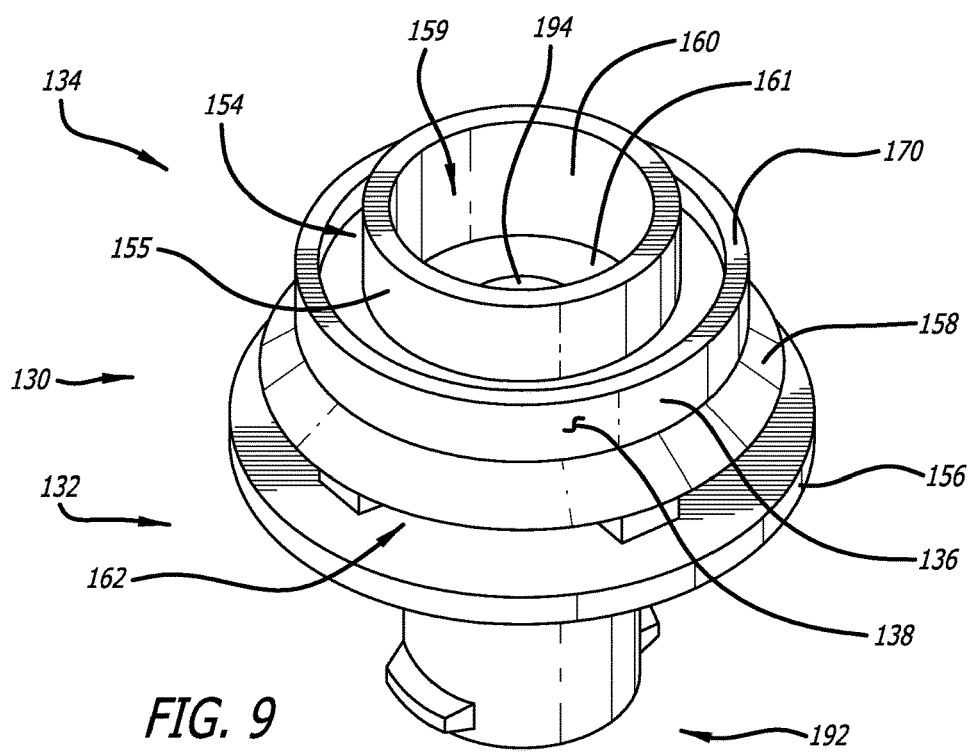

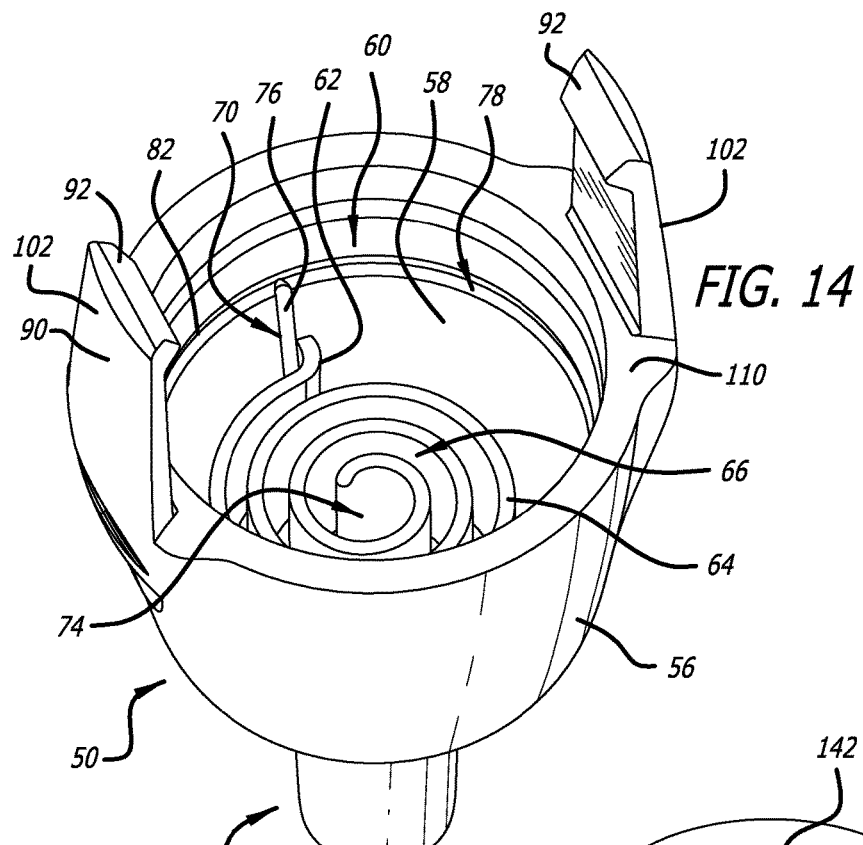
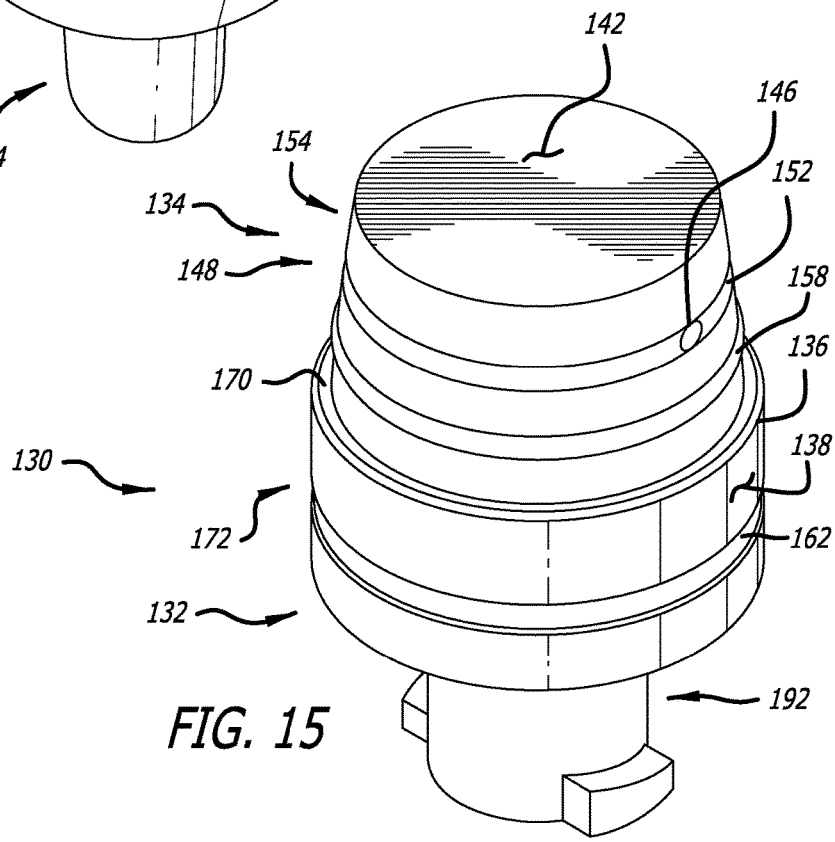

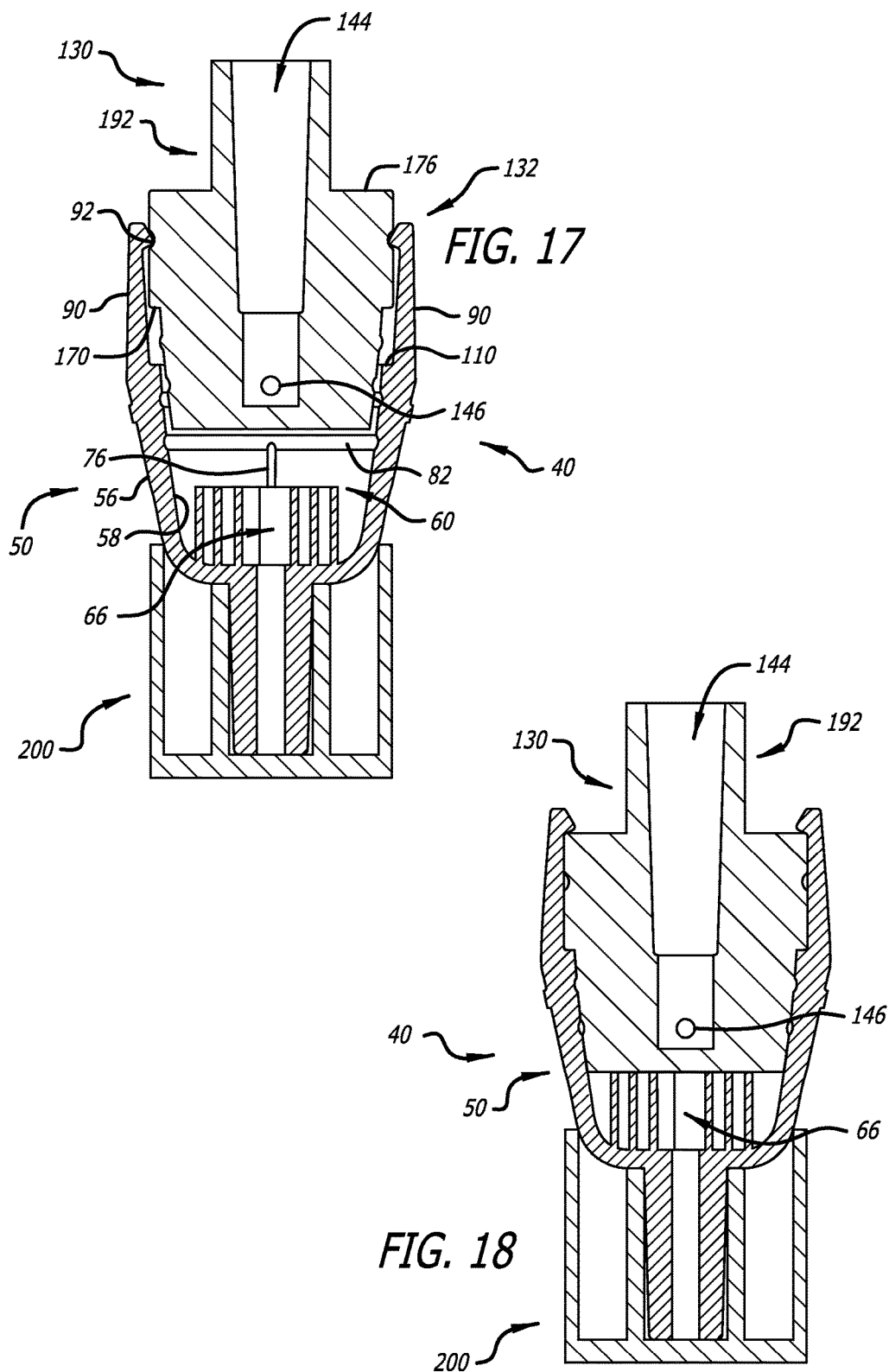

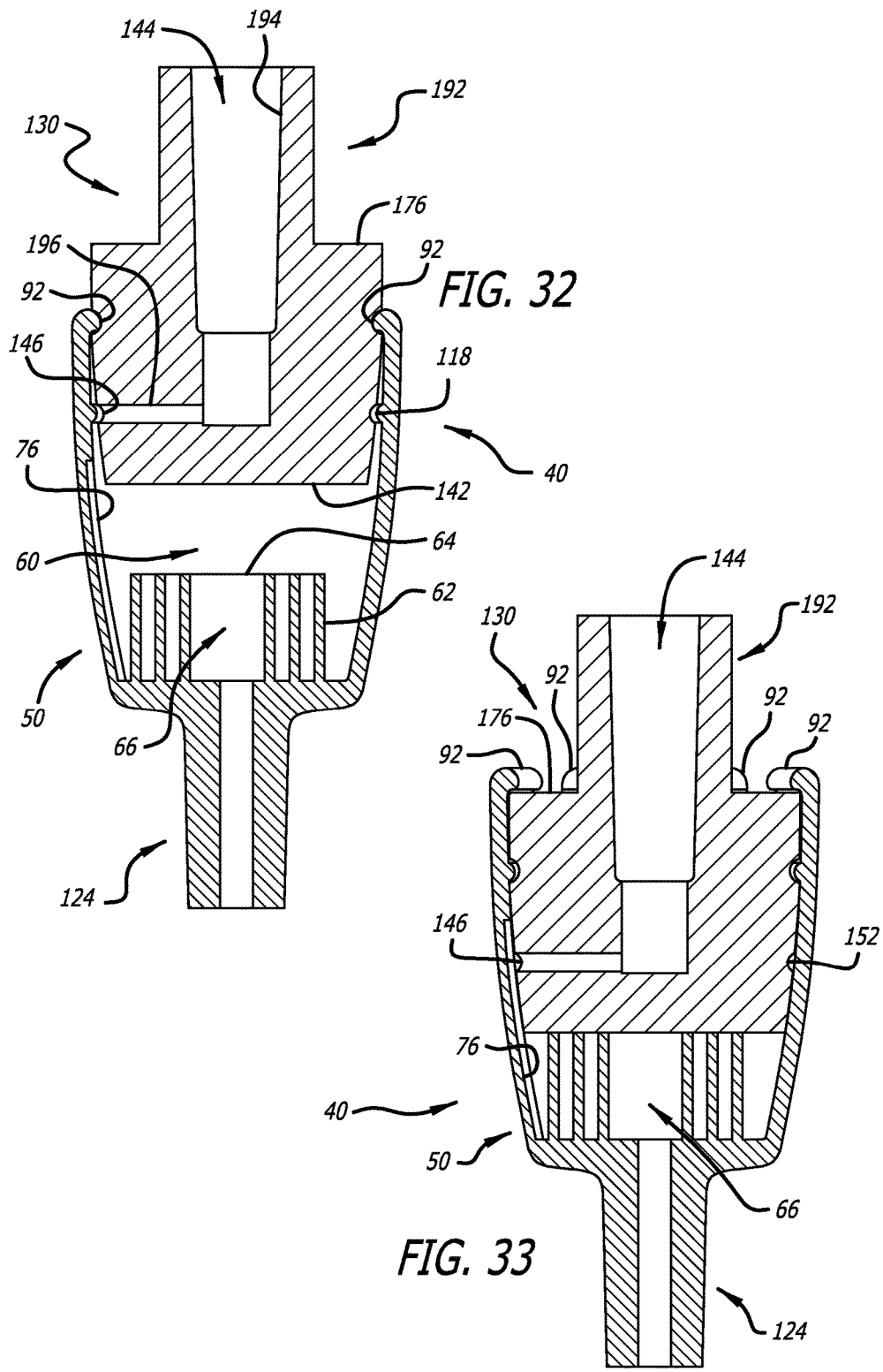

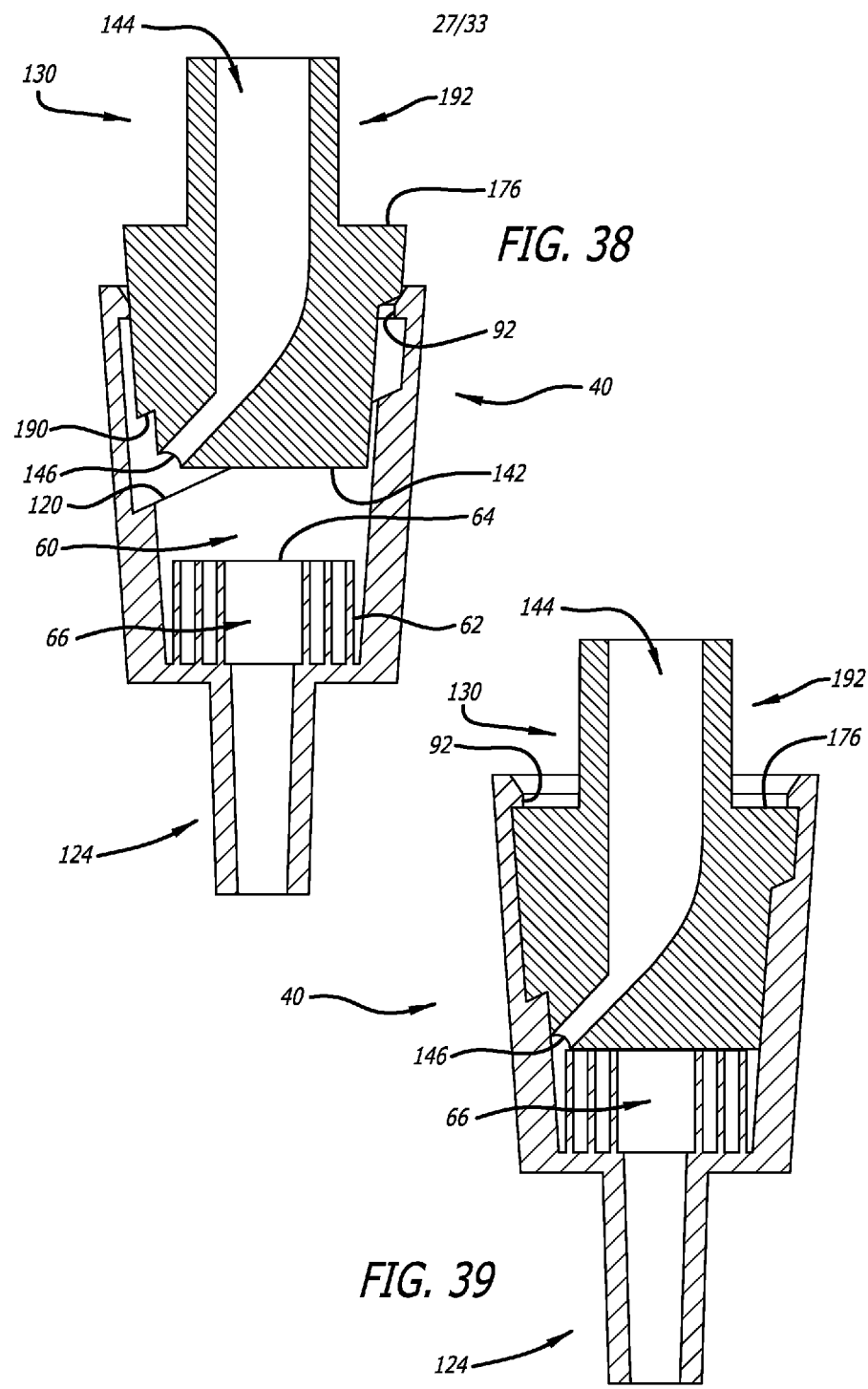

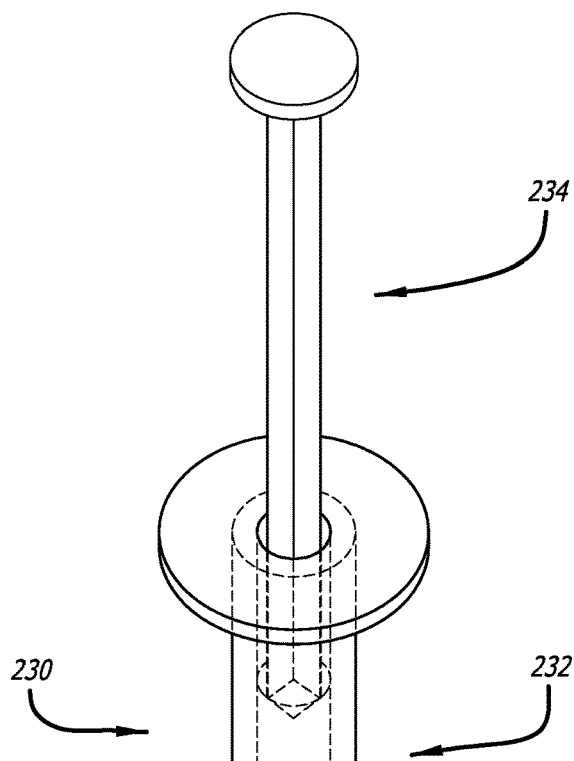
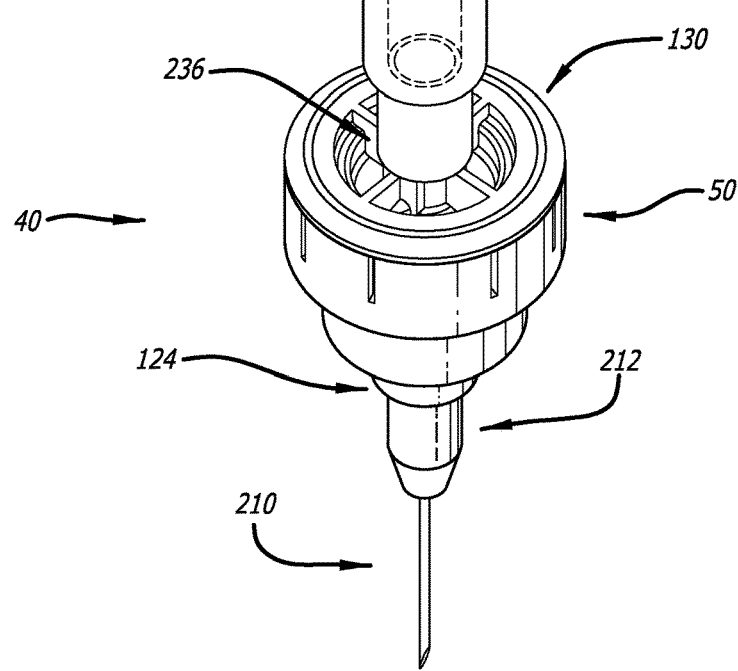
FIG. 40

SOLUTION DELIVERY DEVICE AND METHOD

This application claims priority pursuant to 35 U.S.C. § 119(e) to U.S. Provisional Patent Application 62/048,089, filed Sep. 9, 2014, and entitled "Solution Delivery Device and Method," which is hereby incorporated by reference in its entirety.

The invention relates generally to drug delivery and more particularly, to a solution delivery device and method for storing and mixing medications and related chemicals.

Due to continued advances in genetic and cell engineering technologies, proteins known to exhibit various pharmacological actions in vivo are capable of production in large amounts for pharmaceutical applications. However, one of the most challenging tasks in the development of protein pharmaceuticals is to deal with the inherent physical and chemical instabilities of such proteins, especially in aqueous dosage forms. Pre-filled hypodermic syringes in which these protein pharmaceuticals and other medications are stored in aqueous form offer many efficiencies. However, many injectable medications degrade rapidly and lose their effectiveness in solution. Refrigeration and special packaging can increase shelf-life, but add to cost, complicate storage, and offset many efficiencies provided by pre-filled syringes.

Because of the instability associated with the aqueous dosage forms, powder formulations are generally preferred to achieve sufficient stability for the desired shelf-life of a product. Various techniques to prepare dry powders are known and practiced in the pharmaceutical and biotechnology industry. Such techniques include lyophilization, spray-drying, spray-freeze drying, bulk crystallization, vacuum drying, and foam drying. Lyophilization (freeze-drying) is often a preferred method used to prepare dry powders (lyophilizates) containing proteins. Various methods of lyophilization are well known to those skilled in the art. The lyophilization apparatus and process applies a vacuum that converts liquid portions of a medication into a solid which is subject to a sub-atmospheric pressure to create a vapor. The vapor is drawn from the lyophilization chamber through vapor passages and exhausted to regions external of the lyophilizing apparatus. The lyophilizing process reduces the liquid medication to a dried powdery or granular form.

More particularly, freeze drying, or lyophilization, is a dehydration technique. It takes place while a product is in a frozen state (ice sublimation under a vacuum) and under a vacuum (drying by gentle heating). These conditions stabilize the product, and minimize oxidation and other degradative processes. The conditions of freeze drying permit running the process at low temperatures, therefore, thermally labile products can be preserved. Freeze drying has become an accepted method of processing heat sensitive products that require long term storage at temperatures above freezing.

Steps in freeze drying include pretreatment, freezing, primary drying, and secondary drying. Pretreatment includes any method of treating the product prior to freezing. This may include concentrating the product, formulation revision (i.e., addition of components to increase stability and/or improve processing), decreasing a high vapor pressure solvent or increasing the surface area. Methods of pretreatment include: freeze concentration, solution phase concentration, and formulating specifically to preserve product appearance or to provide lyoprotection for reactive products.

The second step is to freeze the product. Freezing the product decreases chemical activity by decreasing molecular movement. Freezing is essentially the dehydration step in freeze drying; once the solvent matrix is in the solid (frozen) state, the solute matrix is "dry," (although it may contain some amorphous water). A rule of thumb for freezing product is that the product container should preferably not be filled with product to more than half of its total volumetric rating. In practice this may also mean filling the product only to certain depth to facilitate freezing, ice sublimation, and final water/solvent removal. This helps insure, in most cases, that the surface to depth ratio is such that freeze drying is not impeded by the product depth.

Once the product is at the end of its lyophilization cycle it should be removed from the freeze dryer. In a stoppering shelf/tray dryer, an inert gas may be bled into the chamber forming an inert "gas cap" over the product prior to stop. Many products are simply stoppered while under vacuum. The stoppers used most commonly on serum vials/bottles have a vacuum integrity of approximately five years when used in conjunction with tear-off seals. Once the product is stoppered, the system is returned to atmospheric pressure and the lyophilizing shelves are unloaded.

Many devices presently exist in which lyophilized medication is stored in the chamber of a hypodermic syringe. Shortly prior to delivery to a patient, reconstitution is achieved by removing the tip cap from the syringe and placing the sharpened cannula of the syringe into a diluent container such as a vial, ampule, or any other rigid or flexible reservoir which could be engaged to the syringe. The plunger of the syringe is then pulled proximally to draw the diluent into the lyophilized medication chamber for mixing. The diluent reservoir is then removed and discarded. The diluent/powder solution in the syringe is then shaken sufficiently for complete mixing. Unless a sharpened cannula is already attached, one is mounted to the distal end of the syringe and the cannula is used to pierce the patient's skin at an injection site. The syringe plunger is then pushed into the syringe barrel to deliver the mixture to the patient. If necessary, the needle used for reconstitution of the lyophilized medication can be removed and replaced with a cannula more suitable for injection into a patient. An example of a system of this nature is that shown in U.S. Pat. No. 5,752,940 to Grimard.

More complex prior art includes hypodermic syringes made of glass or plastic having multiple chambers; in most cases two chambers. In one particular case, a chamber has a stopper slidably disposed at an intermediate position. A lyophilized medication is stored in the chamber distally located to the stopper, while a selected diluent is stored in the chamber proximally of the stopper. A plunger is slidably disposed in fluid-tight engagement with the chamber wall proximally of the diluent. Movement of the plunger in a distal direction urges both the diluent and the stopper toward the lyophilized medication. The stopper eventually will align with a bypass region formed in the syringe barrel, and further movement of the plunger will cause the diluent to flow through the bypass and into the distal portion of the chamber for fully mixing with the lyophilized medication. An example of a hypodermic syringe similar to the above is shown in U.S. Pat. No. 4,599,082 to Grimard.

The two-component hypodermic syringe assembly described above can function well; however, the need for two axially-spaced chambers along the body of the hypodermic syringe necessitates a longer syringe. In particular, the need for a chamber large enough to mix all of the diluent with all of the lyophilized medication before delivery to the patient dictates a space requirement that makes a container larger than if all the diluent and medication were not mixed before the delivery step. Since the lyophilizing process generally is carried out in the syringe, the lyophilizing apparatus must then be large enough to accommodate the longer syringe. Larger hypodermic syringes and correspondingly larger lyophilizing apparatus are more costly and require more space, which also increases cost.

Currently known devices and methods require thorough reconstitution and mixing of a lyophilized product into a diluent prior to injection, and can typically involve lengthy procedures (in excess of ten steps) in order to reconstitute a solid medication into a liquid formulation prior to administration. Such lengthy reconstitution steps can be complex, arduous, and tedious and may render injection of the lyophilized product unfeasible. Moreover, these complicated procedures present risks of foaming, contamination, and accidental needle pricks to the caregiver.

One of the most important aspects with the distribution of lyophilized product is the reliability of the container. Another important aspect is the control over costs of distribution. Devices used for pharmaceutical products must be disposable but at the same time, of high quality so that the patient is assured of accurately receiving the medication prescribed. Containers for lyophilized medical products should have a low cost, should be reliably usable, and should not negatively affect the shelf life of the product or its quality. Additionally, the container should be easily and safely usable and intuitive to use. Containers having a large number of parts can be less reliable and more expensive to manufacture. Those with movable parts are more so.

By using a diluent from a separate vial or ampule, a separate space for a diluent is not required in the medication container, and it can be more compact. Thus, the syringe barrel can be substantially shorter than prior art two-component syringe assemblies, and a smaller lyophilizing apparatus also can be used. Even better is the use of blunt cannulas to conduct the diluent into the lyophilized medication. Providing a reconstitution container that does not include a movable plunger is even better for reliability and reduced cost.

In prior reconstitution devices and methods, the diluent is fully mixed with the lyophilized medication before delivery to the patient. In such fully mixed form, the concentration of the medication in the patient delivery is constant throughout the entire injection; i.e., there is no gradient. However, it has been found in some therapeutic settings that a gradient delivery of medication would be clinically beneficial to a patient. In particular, a higher concentration of the medication in the initial delivery tapering to a lower concentration during later delivery has been found to provide certain advantages. A device and method that provide such a concentration gradient delivery profile without any separate manipulation would be beneficial.

In other drug or other solution delivery contexts, there are at times needs related to delivering multiple drugs or substances substantially simultaneously as being advantageous in both efficiency in administration and clinical effect. One or more such drugs or substances may be in powder form as having been lyophilized as above-described or may be stored in liquid form, in either case it being desirable not to mix such drugs or substances until administration so as to avoid instability, a premature or unwanted chemical reaction, or other adverse effects; storage of such a combination in mixed form may in cases also simply be prohibited or unsupported by regulatory authorities. Similarly, there may be clinical contexts for on-demand mixing of two liquid drugs or of a liquid drug and other chemical that in any such case would be adversely affected by pre-mixing and would benefit from a substantially simultaneous mixing and delivery step. There is thus a need for a solution delivery device and method that allows for on-demand mixing of drugs and/or chemicals or other substances where prior mixing is undesirable.

Hence those skilled in the art have recognized the need for an improved reconstitution device that facilitates lyophilization, storage, and the rapid reconstitution of dried medications as well as the on-demand mixing and delivery of various combinations of drugs and chemicals stored in solid or liquid form. Another need has been recognized for a reduced size reconstitution device so that costs both in lyophilization and storage are reduced. Another recognized need is for the ability to reduce the number of steps in reconstitution of a dried medication. A further such need has been recognized to be able to quickly and safely administer lyophilized medications "in the field" in emergency situations or otherwise. Reduction in manufacturing complexity and cost are also needs recognized by those of skill in the art. Relatedly, a need has been recognized to enable initial filling of the reconstitution device with the liquid medications pre-lyophilization on a vial fill line or syringe fill line. Yet another need has been recognized to prevent access to the medication within the reconstitution device once lyophilization is completed. An additional need has been recognized for a device that controllably delivers with a gradient concentration. The present invention fulfills these needs and others.

SUMMARY

Aspects of the present invention teach certain benefits in construction and use which give rise to the exemplary advantages described below.

Aspects of the present specification provide a solution delivery device having a container component and a plug component configured for selective engagement with the container component. The container component has an internal cavity including an elongated mixing channel containing a first constituent, and the plug component provides an internal flow path configured for introduction of a second constituent into the mixing channel for mixing with the first constituent. The plug component may be inserted within the container component partially in a first operational mode and fully in a second operational mode.

Other aspects of the present specification provide for the first constituent being a drug and the second constituent a diluent, such that the drug may be lyophilized with the device in the first operational mode and reconstituted with the device in the second operational mode.

Other aspects of the present specification provide for multiple solution delivery devices being employed in tandem for the co-delivery of multiple constituents.

Other aspects of the present specification provide for such a solution delivery device being included in a kit.

Other aspects of the present specification provide for such a solution delivery device being installed within an injector.

Other features and advantages of aspects of the present invention will become apparent from the following more detailed description, taken in conjunction with the accompanying drawings, which illustrate, by way of example, the principles of aspects of the invention.

BRIEF DESCRIPTION OF THE DRAWINGS

The accompanying drawings illustrate aspects of the present invention. In such drawings:

FIG. 8 illustrates an enlarged perspective view of an exemplary container component thereof;

FIG. 9 illustrates an enlarged perspective view of an exemplary plug component thereof;

FIG. 14 illustrates an enlarged perspective view of an exemplary container component thereof;

FIG. 15 illustrates an enlarged perspective view of an exemplary plug component thereof;

FIG. 17 illustrates an assembled side cross-sectional view thereof in a first mode of operation;

FIG. 18 illustrates an assembled side cross-sectional view thereof in a second mode of operation;

FIG. 32 illustrates a reduced scale assembled side cross-sectional view thereof in a first mode of operation;

FIG. 33 illustrates a reduced scale assembled side cross-sectional view thereof in a second mode of operation;

FIG. 38 illustrates an assembled side cross-sectional view thereof in a first mode of operation;

FIG. 39 illustrates an assembled side cross-sectional view thereof in a second mode of operation;

FIG. 40 illustrates a perspective view of an exemplary solution delivery device according to aspects of the present invention as in FIGS. 1-6 shown in use in combination with a syringe and cannula;

Figure 1:
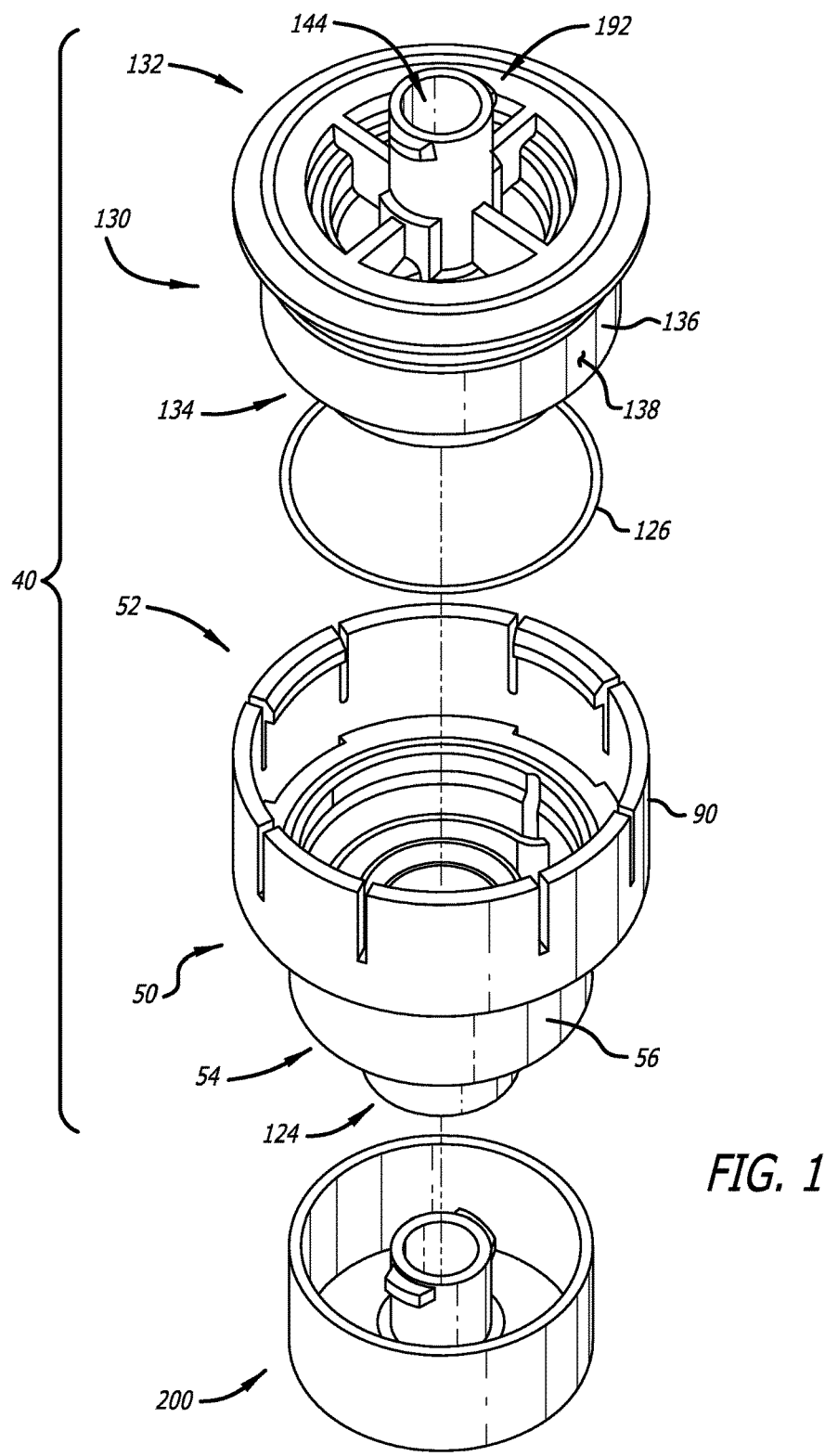
FIG. 1 illustrates an exploded perspective view of an exemplary solution delivery device according to aspects of the present invention.

The above described drawing figures illustrate aspects of the invention in at least one of its exemplary embodiments, which are further defined in detail in the following description. Features, elements, and aspects of the invention that are referenced by the same numerals in different figures represent the same, equivalent, or similar features, elements, or aspects, in accordance with one or more embodiments.

DETAILED DESCRIPTION

The present specification relates generally to a solution delivery device configured for delivering a delivery solution comprising at least two constituents without the need for a separate mixing, shaking, reconstituting, or priming step. It should be understood that the word "solution" is to be interpreted broadly as any combination of two substances, whether any such substances begin in solid, semi-solid, liquid, or gaseous phase and whether any such combination ends in solid, semi-solid, liquid, or gaseous phase and further whether the combination is a mechanical mixture, involves a chemical reaction, or both. Such a solution expressly need not be homogeneous. Further, the word "constituent" is also to be interpreted broadly as any substance combined with another to form a delivery solution according to aspects of the present invention, such constituents including but not limited to a drug, a chemical, a matrix, an albumin, an antibody fragment, a marker, a carrier, a targeting molecule, a diagnostic, and a diluent or any combination thereof. Those skilled in the art will thus appreciate that while exemplary constituents forming exemplary delivery solutions in cooperation with exemplary solution delivery devices and methods and contexts of use are disclosed herein, the invention is not so limited, but may take numerous other forms in numerous other contexts without departing from the spirit and scope of the invention.

Referring now to FIGS. 1-6, there is shown a first exemplary solution delivery device 40 according to aspects of the present invention. The device 40 generally comprises a container component 50 and a plug component 130. The container component 50 has an open proximal end 52 and an opposite distal end 54 at which is formed an external ejection connector port 124. The container component 50 is formed having a lower base wall 56 and an upper engagement wall 90, more about which is said below as relating to engagement with the plug component 130. The base wall 56 has an inner surface 58 and defines an internal cavity 60 with a size selected to contain a predetermined quantity of a first constituent. Within the cavity 60 there is formed or installed an elongated channel wall 62 to form an elongated mixing channel 66 having a substantially open top 68 and a substantially closed bottom 72. Nearer to the open top 68 of the mixing channel 66 and substantially adjacent the inner surface 58 of the base wall 56 there is formed or defined a channel input end 70 in fluid communication with the plug outlet port 146 when the device 40 is in its second operational mode and an opposite output end 74 in fluid communication with the ejection connector port 124, more about which is said below, particularly in connection with FIG. 6. The plug component 130 is generally configured for selective engagement with the container component 50 in at least first and second operational modes, the plug component 130 having a proximal end 132, an opposite distal end 134, and a side wall 136 having an outer surface 138 disposed between the ends, the side wall 136 and distal end 134 together defining a plug periphery 140. The plug component has an external inlet connector port 192 substantially at the proximal end 132 and an internal flow path 144 from the inlet connector port 192 to a plug outlet port 146 intersecting the plug periphery 140. It will be appreciated by those skilled in the art that while the container and plug components 50, 130 generally are shown as being annular, the invention is not so limited; rather, the components and their various features can take a variety of other geometric shapes and configurations without departing from the spirit and scope of the invention. Relatedly, and as will be appreciated with reference to the numerous alternative embodiments shown and described herein, the particular configurations of the walls, engagement surfaces and features, and sizes and proportions of any such features are merely illustrative of aspects of the present invention and non-limiting.

Figure 2:
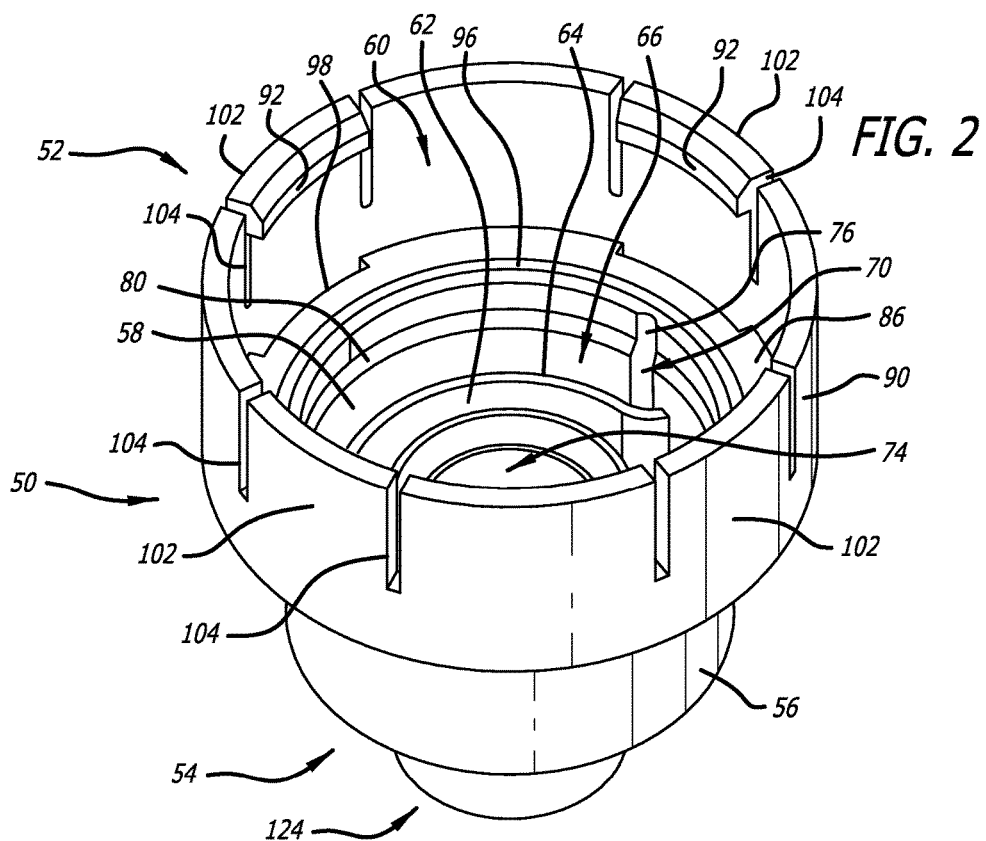
FIG. 2 illustrates an enlarged perspective view of an exemplary container component thereof.
Figure 5:
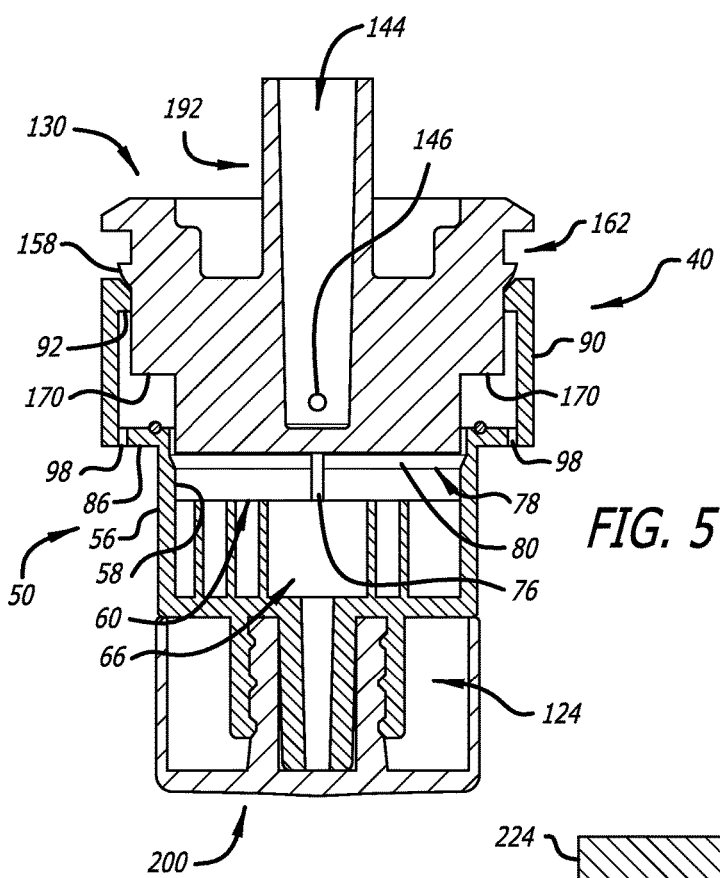
FIG. 5 illustrates an assembled side cross-sectional view thereof in a first mode of operation.
Figure 6:
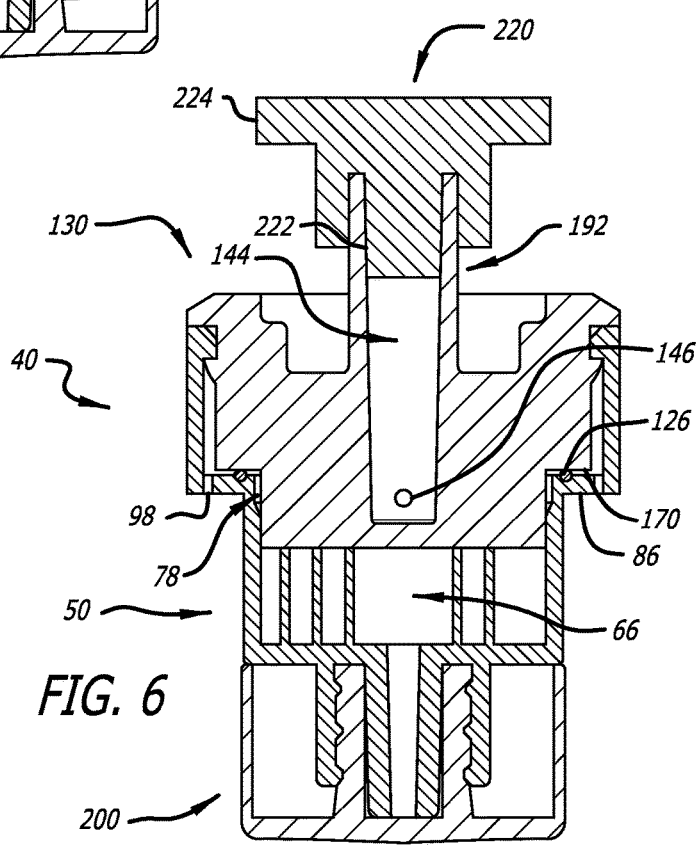
FIG. 6 illustrates an assembled side cross-sectional view thereof in a second mode of operation.

Referring to FIG. 2, there is shown an enlarged perspective view of the exemplary container component 50. Once more, the container component 50 generally comprises a lower base wall 56 and an upper engagement wall 90 forming its body. In the illustrated embodiment, the container component 50 further comprises an interconnecting groove 76 formed in the inner surface 58 of the base wall 56 so as to be in fluid communication with the input end 70 of the mixing channel 66. Preferably, the interconnecting groove 76 is substantially lengthwise along the container component base wall 56, though it will be appreciated that other orientations of the groove 76 may also be employed. The interconnecting groove 76 is of sufficient length to be in fluid communication with the plug outlet port 146 (FIGS. 3-6) upon assembly of the plug component 130 within the container component 50 in the second operational mode, as shown in FIG. 6, whereby the mixing channel 66 provides an indirect flow path between the plug outlet port 146 and the ejection connector port 124. The container component 50 further generally comprises a distribution groove 78 formed in the inner surface 58 of the base wall 56 so as to be in fluid communication with the interconnecting groove 76. In the exemplary embodiment, the distribution groove 78 is configured as an upwardly-opening step 80 in the inner surface 58 of the base wall 56, such that the base wall 56 has a stepped inner bore. As shown, the step 80 is angled so as to provide a countersink transition to the inner surface 58 of the base wall 56 beneath or proximal of the step 80. Further, the step 80 has a depth terminating along the inner surface 58 of the base wall 56 proximal of the channel wall top surface 64, thereby forming a container seating portion 84 of the inner surface 58 between the step 80 and the mixing channel 66, more about which is said below regarding the device 40 in use. In the exemplary embodiment as shown, once again, the container component 50 being substantially annular, it follows, though not necessarily so, that the distribution groove 78 here defined by the step 80 formed within the container component lower wall 56 is also substantially annular. Furthermore, as illustrated, the distribution groove is substantially continuous, though once more, there are configurations of the device in which there may not be a distribution groove or if there is it may not be continuous. Those skilled in the art will again appreciate that a variety of such components and configurations are possible without departing from the spirit and scope of the invention.

Figure 4:
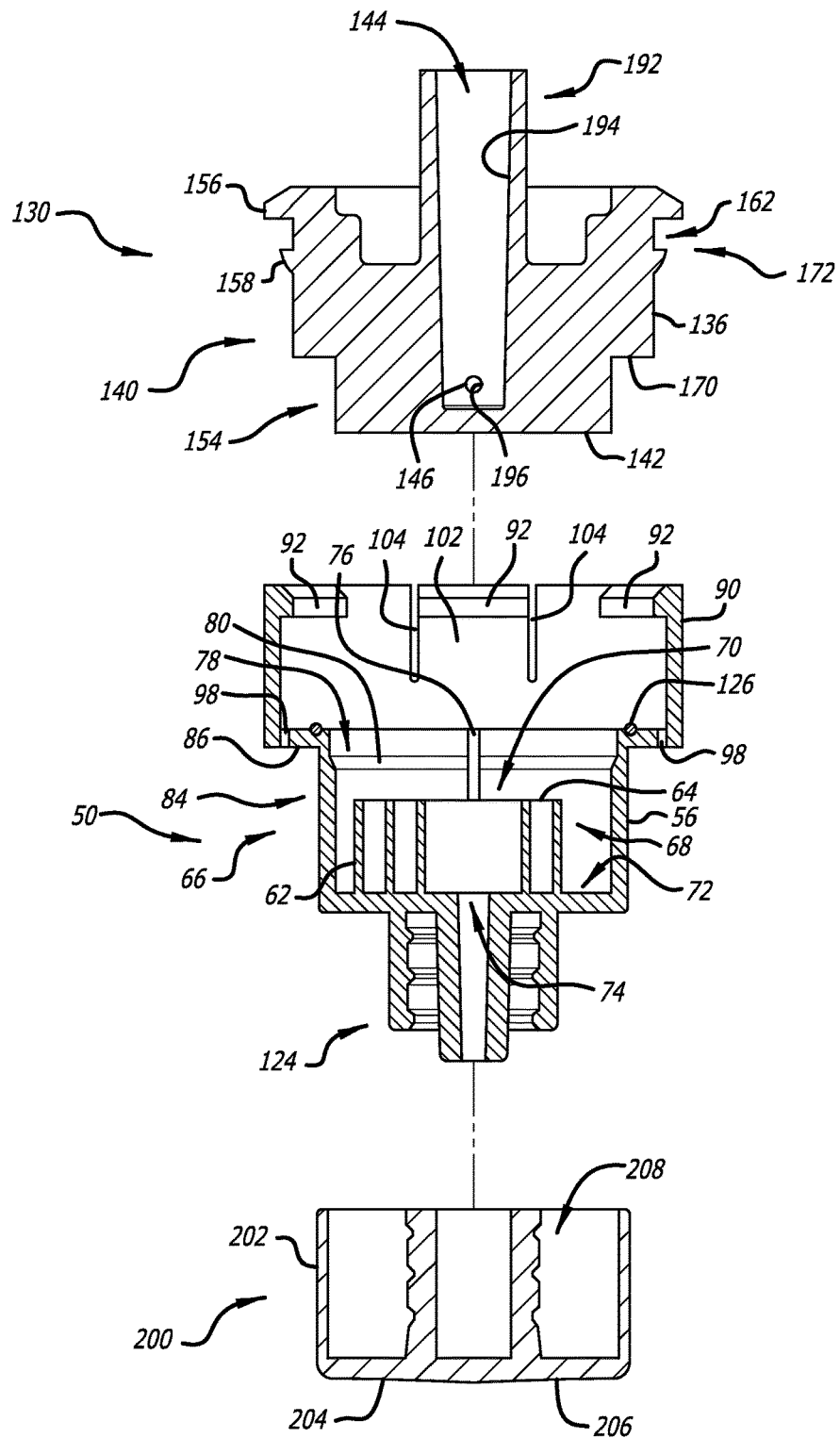
FIG. 4 illustrates an exploded side cross-sectional view thereof.

With continued reference to FIG. 2 in conjunction with FIG. 4, the base wall 56 of the container component 50 is shown as terminating proximally in a substantially radially-outwardly extending container flange 86 that transitions to or terminates radially in the proximally extending engagement wall 90, which itself terminates proximally in a radially-inwardly projecting engagement lip 92. In the exemplary embodiment, the radially-inwardly projecting engagement lip 92 is formed on a flexible leg 102 defining a portion of the engagement wall 90 of the container component 50. More particularly, as illustrated, four such flexible legs 102 are formed spaced about the engagement wall 90, as by forming opposite and substantially vertical and parallel notches 104 in the wall 90, with the flexible legs 102 being defined by the upwardly-extending portions of the wall 90 bound by the notches 104 so as to operate like living hinges. It will be appreciated that the container component 50 may thus be configured with virtually any number of flexible legs 102 with proximal, radially-inwardly projecting engagement lips 92, such as two, three, four as shown, or more. Further, alternatively, the at least one radially-inwardly projecting engagement lip 92 itself may be flexible and configured for shifting relative to the plug component 130 as it is inserted within the container component 50. For example, and by way of non-limiting illustration, the material from which the container component 50 may be formed, and particularly the legs 102 and/or lips 92, so as to have the desired flexibility or resiliency, as well as meeting the requirements for medical use, including sterility, may include polyethylene, polypropylene, acrylic, nylon, silicone, or any combinations thereof or any other such materials now known or later developed. Those skilled in the art will appreciate that any such material now known or later developed may be employed in the present invention. As also shown, at least one container vent hole 98 is formed within the container flange 86 radially outwardly of the base wall 56, whereby in the first operational mode of the device 40 with the plug component 130 partially inserted within the container component 50, as shown in FIG. 5, there is fluid communication between the inner cavity 60 of the container component and the surrounding atmosphere at least through the at least one container vent hole 98. In the exemplary embodiment, the size and locations of the vent holes substantially correspond to the locations of the legs 102 and related lips 92, as might result from or be accomplished through an injection molding process with a core pull to simultaneously form each vent hole 98 and undercut of the respective engagement lip 92, though it will be appreciated that a wide variety of configurations and locations of such vent holes is possible without departing from the spirit and scope of the invention.

Figure 3:
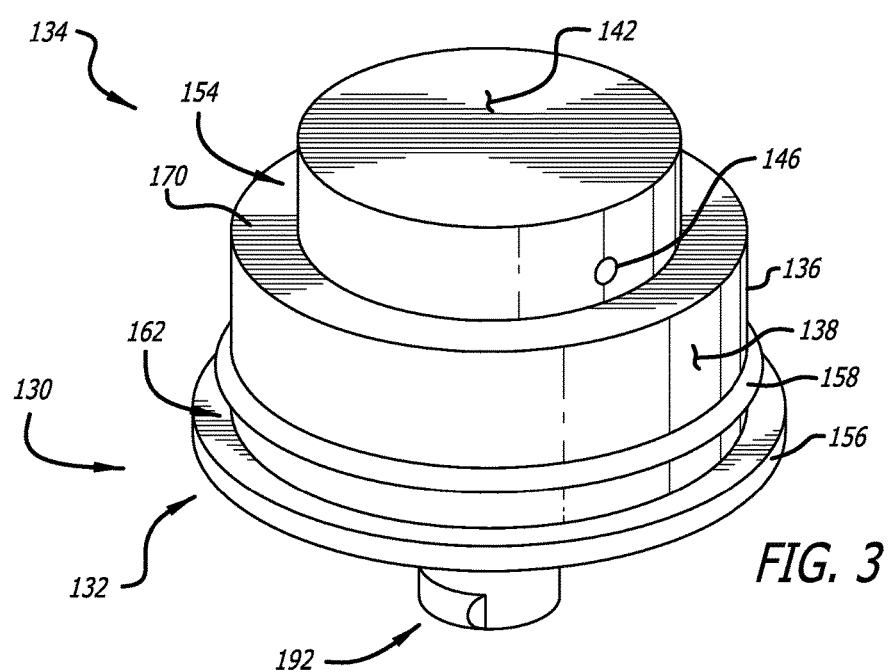
FIG. 3 illustrates an enlarged perspective view of an exemplary plug component thereof.

Turning to FIG. 3, the exemplary plug component 130 is shown enlarged and inverted relative to FIG. 1. The outer surface 138 of the side wall 136 of the plug component 130 is formed having a plug seating portion 154 configured to seat against the container seating portion 84 (FIG. 4) of the inner surface 58 of the base wall 56 of the container component 50 upon assembly of the plug component 130 within the container component 50 in the second operational mode as shown in FIG. 6. The plug outlet port 146 is located in the side wall 136 proximal of the plug seating portion 154, such that in the second operational mode the plug outlet port 146 is adjacent to and in fluid communication with the distribution groove 78, here configured as or formed by the step 80 in the bore of the container component 50 (FIG. 4), more about which is said below, particularly in connection with FIG. 6. As best seen in FIG. 4, the flow path 144 through the plug component 130 comprises a substantially axial bore 194 formed in the inlet connector port 192 intersected by and in fluid communication with a substantially transverse bore 196 defining the plug outlet port 146. It will be appreciated that a variety of other flow path configurations through the plug component and related placement of the plug outlet port 146 are possible without departing from the spirit and scope of the invention. An outwardly-opening engagement groove 162 is formed in the outer surface 138 of the side wall 136 of the plug component 130 so as to be selectively engaged by the engagement lip 92 of the container component 50 (FIGS. 2 and 4) during operation of the device 40. In the exemplary embodiment, the engagement groove 162 is formed between a proximal radially-outwardly extending plug flange 156 and a distally offset radially-outwardly projecting retention lip 158. In an alternative embodiment, there is no plug flange, such that the retention lip 158 defines a substantially proximally-facing engagement groove proximally engaged by the engagement lip 92 upon assembly of the plug component 130 within the container component 50 in the second operational mode. As shown, the retention lip 158 is in this exemplary embodiment substantially continuous while the engaggement lip 92 is circumferentially associated only with each flexible leg 102 or is thereby discontinuous or discretely formed per leg 102. It will be appreciated that by here forming the retention lip 158 of the plug component 130 to be substantially continuous, no matter the orientation of the plug component 130 relative to the container component 50 the two components may be engaged as by the engagement lips 92 of the one or more flexible legs 102 formed on the container component 50 engaging the substantially continuous retention lip 158 of the plug component 130 when the two components are fully assembled as shown in FIG. 6 and any fluid introduced into the plug component 130 through its inlet connector port 192 and the associated internal flow path 144 will be able to make its way into the mixing channel 66 of the container component 50 due to the plug outlet port 146 being in fluid communication with the interconnecting groove 76, and hence the mixing channel 66, through the substantially continuous distribution groove 78 formed as the step 80 in the inner surface 58 of the base wall 56 of the container component 50. With continued reference to FIGS. 3 and 4, the plug component 130 is further formed having a stepped side wall 136 defined by a distally-facing shoulder 170 separating a relatively larger diameter proximal plug engagement portion 172 from the relatively smaller diameter distal plug seating portion 154. The distance from the engagement lip 92 to the container flange 86 of the container component 50 is substantially equivalent to the distance from the engagement groove 162 to the shoulder 170 of the plug component 130, whereby engagement of the engagement lip 92 within the engagement groove 162 upon assembly of the plug component 130 within the container component 50 in the second operational mode substantially positions the shoulder 170 of the plug component 130 adjacent to the container flange 86 of the container component 50. In this embodiment, the container flange 86 is formed with a proximally-opening o-ring groove 96 radially offset from the base wall 56, and an o-ring 126 is seated in the o-ring groove 96 so as to provide a seal between the distally-facing shoulder 170 of the plug component 130 and the proximally-facing surface of the container flange 86 of the container component 50 upon assembly of the plug component 130 within the container component 50 in the second operational mode. Furthermore, the distance from the container flange 86 to the wall top surface 64 of the elongated channel wall 62 installed within the internal cavity 60 of the container component 50 is substantially equivalent to the distance from the shoulder 170 to the distal end 134 of the plug component 130, or the plug distal surface 142, whereby assembly of the plug component 130 within the container component 50 in the second operational mode such that the engagement lip 92 of the container component 50 is engaged within the engagement groove 162 of the plug component 50 and the shoulder 170 of the plug component 130 is positioned adjacent to the container flange 86 of the container component 50 causes the plug distal surface 142 of the plug component 130 to substantially seat against the wall top surface 64 of the elongated channel wall 62 of the container component 50 to substantially close the top 68 of the elongated mixing channel 66 and further causes the plug seating portion 154 of the plug component 130 to seat within the container seating portion 84 of the container component 50 to substantially seal the elongated mixing channel 66 other than the input end 70 in fluid communication with the plug outlet port 146. In this embodiment, the at least one container vent hole 98 is formed as shown within the container flange 86 radially outwardly of the o-ring groove 96, more about which is said below in connection with FIGS. 5 and 6.

In use of such a solution delivery device 40 as shown in FIGS. 1-4, in the exemplary context of a liquid medication to be subjected to a lyophilization procedure, it will be appreciated that a first step is essentially to fill the internal cavity 60, and particularly the elongated mixing channel 66, of the container component 50 with the desired amount of liquid to be lyophilized. Preferably, as shown in FIG. 5, the container component 50 has its external ejection connector port 124 capped as by engaging therewith a container outlet cap 200, thereby closing the bottom or distal opening of the container component 50 and thus the device 40. The container outlet cap 200 is configured for selective sealable engagement with the external ejection connector port 124, each of which may be configured as standard luer connectors as are known and used in the art. Alternatively, a thin membrane (not shown) may be positioned over the opening to the ejection connector port 124, or substantially at the output end 74 of the mixing channel 66, so as to completely contain the liquid within the mixing channel 66 and not have any pass into the ejection connector port 124; even so, the outlet cap 200 would be installed both for further sealing and integrity of the ejection connector port 124 and for facilitating the filling and lyophilization processes. Preferably, the device 40 would remain substantially upright or vertical for the filling step as well as during the subsequent lyophlization procedure. Accordingly, as shown particularly in FIGS. 4 and 5, the container outlet cap 200 has an outlet cap wall 202 terminating distally in an outlet cap base 204 defining an outlet cap base surface 206. Preferably, as shown, the outlet cap base surface 206 is substantially flat or planar so as to be capable of resting flush against a substantially flat or planar horizontal support surface. Instead or additionally, the outlet cap wall 202 may be configured to seat within a receptacle (not shown) or other support structure on a vial fill line and/or within a lyophilization machine. Relatedly, in the exemplary embodiment, the outlet cap wall 202 is substantially coterminous with the container base wall 56 when the outlet cap 200 is removably installed on the container component 50. Alternatively, the outlet cap wall 202 has an outlet cap diameter that is at least as large as the diameter of the container base wall 56. The idea is that the device 40 in at least one embodiment would be capable of standing vertically on the container outlet cap 200, such that the outlet cap perimeter is generally sufficient to permit such self-support or free standing of the device 40. Thus, if the outlet cap perimeter has an outlet cap cross-sectional area and the container base wall defines a container perimeter having a container cross-sectional area, in one embodiment the outlet cap cross-sectional area is at least 50% of the container cross-sectional area, in a further embodiment the outlet cap cross-sectional area is at least 60% of the container cross-sectional area, in a still further embodiment the outlet cap cross-sectional area is at least 70% of the container cross-sectional area, in a still further embodiment the outlet cap cross-sectional area is at least 80% of the container cross-sectional area, in a still further embodiment the outlet cap cross-sectional area is at least 90% of the container cross-sectional area, in a still further embodiment the outlet cap cross-sectional area is at least 95% of the container cross-sectional area, and in a still further embodiment the outlet cap cross-sectional area is at least 100% of the container cross-sectional area. It will be appreciated that a variety of other sizes and component proportions are possible according to aspects of the present invention. It will also be appreciated that once so configured with the container outlet cap 200 engaged with or installed on the container component 50 as shown and described, the device 40 may then be placed in any suitable automated, semi-automated, or manual filling machine for the purpose of filling the cavity 60 or particularly the mixing channel 66 with the desired predetermined quantity of liquid. In one exemplary embodiment, the predetermined quantity of the first constituent is nominally one tenth of a cubic centimeter (0.1 cc), in a further exemplary embodiment, the predetermined quantity of the first constituent is nominally two tenths of a cubic centimeter (0.2 cc), in a still further exemplary embodiment, the predetermined quantity of the first constituent is nominally three tenths of a cubic centimeter (0.3 cc), in a still further exemplary embodiment, the predetermined quantity of the first constituent is nominally four tenths of a cubic centimeter (0.4 cc), in a still further exemplary embodiment, the predetermined quantity of the first constituent is nominally one half of a cubic centimeter (0.5 cc), in a still further exemplary embodiment, the predetermined quantity of the first constituent is nominally six tenths of a cubic centimeter (0.6 cc), in a still further exemplary embodiment, the predetermined quantity of the first constituent is nominally seven tenths of a cubic centimeter (0.7 cc), in a still further exemplary embodiment, the predetermined quantity of the first constituent is nominally eight tenths of a cubic centimeter (0.8 cc), in a still further exemplary embodiment, the predetermined quantity of the first constituent is nominally nine tenths of a cubic centimeter (0.9 cc), in a still further exemplary embodiment, the predetermined quantity of the first constituent is nominally one cubic centimeter (1.0 cc), in a still further exemplary embodiment, the predetermined quantity of the first constituent is nominally one and one tenth cubic centimeters (1.1 cc), in a still further exemplary embodiment, the predetermined quantity of the first constituent is nominally one and two tenths cubic centimeters (1.2 cc), in a still further exemplary embodiment, the predetermined quantity of the first constituent is nominally one and three tenths cubic centimeters (1.3 cc), in a still further exemplary embodiment, the predetermined quantity of the first constituent is nominally one and four tenths cubic centimeters (1.4 cc), in a still further exemplary embodiment, the predetermined quantity of the first constituent is nominally one and one half cubic centimeters (1.5 cc), in a still further exemplary embodiment, the predetermined quantity of the first constituent is nominally one and six tenths cubic centimeters (1.6 cc), in a still further exemplary embodiment, the predetermined quantity of the first constituent is nominally one and seven tenths cubic centimeters (1.7 cc), in a still further exemplary embodiment, the predetermined quantity of the first constituent is nominally one and eight tenths cubic centimeters (1.8 cc), in a still further exemplary embodiment, the predetermined quantity of the first constituent is nominally one and nine tenths cubic centimeters (1.9 cc), in a still further exemplary embodiment, the predetermined quantity of the first constituent is nominally two cubic centimeters (2.0 cc), in a still further exemplary embodiment, the predetermined quantity of the first constituent is nominally two and one tenth cubic centimeters (2.1 cc), in a still further exemplary embodiment, the predetermined quantity of the first constituent is nominally two and two tenths cubic centimeters (2.2 cc), in a still further exemplary embodiment, the predetermined quantity of the first constituent is nominally two and three tenths cubic centimeters (2.3 cc), in a still further exemplary embodiment, the predetermined quantity of the first constituent is nominally two and four tenths cubic centimeters (2.4 cc), in a still further exemplary embodiment, the predetermined quantity of the first constituent is nominally two and one half cubic centimeters (2.5 cc), in a still further exemplary embodiment, the predetermined quantity of the first constituent is nominally two and six tenths cubic centimeters (2.6 cc), in a still further exemplary embodiment, the predetermined quantity of the first constituent is nominally two and seven tenths cubic centimeters (2.7 cc), in a still further exemplary embodiment, the predetermined quantity of the first constituent is nominally two and eight tenths cubic centimeters (2.8 cc), in a still further exemplary embodiment, the predetermined quantity of the first constituent is nominally two and nine tenths cubic centimeters (2.9 cc), and in a still further exemplary embodiment, the predetermined quantity of the first constituent is nominally three cubic centimeters (3.0 cc). Those skilled in the art will appreciate that a wide variety of sizes or nominal volumes particularly of the predetermined quantity of the first constituent and thus the volume of the cavity 60 and/or the mixing channel 66, accounting for the elongated channel wall 62, are possible within the present invention. In one context, the container component 50 so sized and engaged with the outlet connector cap 200 is positioned for filling without the plug component 130 yet in place as shown in FIG. 5, such that the plug component 130 is subsequently inserted within the container component 50 after the filling step is completed, as again by an automated, semi-automated, or manual process. Alternatively, the filling of the container component 50 can be accomplished even with the plug component 130 partially inserted in the first operational mode of the device 40 as shown in FIG. 5, such as through the inlet connector port 192, as by passing through the flow path 144 and out the plug outlet port 146 so as to flow down into the cavity 60 of the container component 50.

With continued reference to FIG. 5, there is again shown the device 40 in its first operational mode, wherein the plug component 130 is partially inserted within the container component 50. Specifically, the radially-outwardly projecting retention lip 158 formed on the outer surface 138 of the side wall 136 (FIGS. 3 and 4) of the plug component 130 seats on the radially-inwardly projecting engagement lip 92 formed proximally on the engagement wall 90 of the container component 50. In this position, the shoulder 170 of the plug component 130 is suspended above the container flange 86 of the container component 50 and the plug seating portion 154 (FIGS. 3 and 4) of the plug component 130 is at least partially suspended within the distribution groove 78 formed as an upwardly-opening step 80 in the inner surface 58 of the base wall 56 of the container component 50 and is not yet within the container seating portion 84 (FIG. 4), thereby providing clearance between the plug and container components so as to facilitate fluid communication between the internal cavity 60 of the container component 50, and particularly the elongated mixing channel 66, and the surrounding atmosphere through one or more container vent holes 98. It will be appreciated by those skilled in the art that in such a first operational mode or position of the device 40, the device may then be subjected to a lyophilization process whereby the interior of the container component 50 can vent or have a vacuum pulled on it or be subjected to any other process that requires fluid flow relative to the liquid to be processed.

Referring now to FIG. 6, once, as in the exemplary context, the lyophlization procedure is complete, the plug component 130 may then be fully inserted within the container component 50 as shown, which may again be accomplished by an automated, semi-automated, or manual process. As shown, a plug inlet cap 220 may be installed on the inlet connector port 192 so as to cap the plug component 130 and thus close off the fluid flow path 144. Such inlet cap 220 may be of any configuration now known or later developed in the art for removable and sealable engagement with the inlet port 192; in the exemplary embodiment each is configured as a standard luer connector, such that the cap 220 is particularly formed with a male inlet cap luer connector 222 configured to engage the female luer inlet port connector 192 in a conventional manner. A flange 224 is shown as being provided on the inlet cap 220 to enhance gripping and manipulation, though those skilled in the art will appreciate that other enhancements such as knurling of the exterior surface of the cap 220 may be employed instead of or in addition to such a flange 224. The inlet cap 220 may be positioned on the inlet connector port 192 before or after the plug component 130 is inserted into the container component 50, and whether in the first operational mode depicted in FIG. 5 or the second operational mode depicted in FIG. 6, though of course the cap 220 is here only shown for illustration on the inlet connector port 192 in FIG. 6 relating to the device 40 in the second operational mode. As described above and will thus be appreciated by those skilled in the art, pushing the plug component 130 all the way into the container component 50 such that, here, the container's engagement lip 92 engages the plug's engagement groove 162 (FIGS. 4 and 5), most notably, the plug distal surface 142 is thus brought into engagement or substantially abutting contact with or otherwise substantially adjacent to the top surface 64 of the wall 62 of the mixing channel 66 (FIG. 4), thereby effectively closing off the mixing channel 66 except for its input end 70 (FIG. 2) substantially fluidly connected to the flow path 144 through the plug component 130. More about the device 40 so configured in its second operational mode post-lyophilization in various exemplary contexts and clinical uses and hence various constituents within the device 40 are all discussed further below, particularly in connection with FIGS. 40-42, but here it is sufficient to note that flowing a second constituent into the device 40 as through the inlet connector port 192 and associated flow path 144 of the plug component 130 allows such second constituent to exit the plug outlet port 146, fill the distribution groove 78, and then find its way into the mixing channel 66 through the longitudinal interconnecting groove 76 (FIGS. 4 and 5) that is somewhat contiguous with the mixing channel input end 70 (FIG. 2) so as to then reconstitute the previously lyophilized first constituent housed within the mixing channel 66, once again without any separate mixing, shaking, priming, or other reconstitution step. Relatedly, when the plug component 130 is thus seated within the container component 50 so as to configure the device 40 in the second operational mode, the plug shoulder 170 is brought adjacent to the container flange 86 so as to squeeze and seal against the o-ring 126 and thereby seal off the container vent holes 98 and form or completely bound the distribution groove 78, such that any second constituent entering the device 40 and making its way into the interior cavity 60, and particularly the distribution groove 78, of the container component 50 can only then flow into the mixing channel 66 and not back out of the device 40 through any other path, thus again forcing the reconstitution of the first constituent or the mixing of the first and second constituents within the mixing channel 66. Relatedly, if the distribution groove 78 is effectively sealed "above" by the o-ring 126, then it is effectively sealed "below" through the engagement between the plug seating portion 154 and the container seating portion 84. In the exemplary embodiment, the effective engagement between these surfaces is a net-fit arrangement. Particularly, the two surfaces or seating portions 84, 154 are here shown as substantially straight annular walls configured to be brought into substantially abutting contact upon full assembly of the plug component 130 within the container component 50. It will be appreciated by those skilled in the art, with further reference to the numerous alternative embodiments presented herein, that a variety of other configurations and interoperability of the components of a solution delivery device according to aspects of the present invention are thus possible without departing from its spirit and scope. It is further noted in connection with putting the device 40 into the second operational mode shown in FIG. 6, or shifting the device 40 from the first operational mode as shown in FIG. 5 to the second operational mode as shown in FIG. 6, that the flexible legs 102 of the container component 50 on which are formed the engagement lips 92 allow the lips 92 to deflect or shift radially outwardly to pass over the retention lip 158 and then spring or seat into the plug engagement groove 162. In the exemplary embodiment of FIGS. 1-6, each flexible leg 102 is attached to the engagement wall 90 along a lower edge so as to function as a living hinge, such that the geometric or mechanical design along with the selection of an appropriate medical grade plastic with sufficient elasticity enables the requisite flexibility and functionality. Moreover, as can be seen and will be appreciated, the engaging or opposed surfaces of the respective engagement lip 92 and retention lip 158 are sloped so as to effectively provide a ramp along which the engagement lip 92 travels as it shifts radially outwardly as the plug component 130 is advanced distally within or relative to the container component 50 until the engagement lip 92 clears the retention lip 158 proximally and seats within the engagement groove 162 to effectively lock the plug component 130 within the container component 50 in the configuration of the device 40 shown in FIG. 6. As will also be appreciated from FIG. 6, in the exemplary embodiment the plug flange 156 defines a plug perimeter that is substantially radially coterminous with the engagement wall 90 of the container component 50 for a substantially flush fit between the plug and container components when the device 40 is in its second operational mode as shown.

Turning next to FIGS. 7-12, there is shown a second exemplary solution delivery device 40 according to aspects of the present invention. The device 40 being somewhat analogous to that of FIGS. 1-6 again generally comprises a container component 50 having an open proximal end 52 and an opposite distal end 54 at which is formed an external ejection connector port 124 and a plug component 130 configured to be inserted at least partially within the open end 52 of the container component 50. The plug component 130 is generally configured for selective engagement with the container component 50 in at least first and second operational modes, the plug component 130 having a proximal end 132, an opposite distal end 134, and a side wall 136 having an outer surface 138 disposed between the ends, the side wall 136 and distal end 134 together defining a plug periphery 140. The plug component has an external inlet connector port 192 substantially at the proximal end 132 and an internal flow path 144 from the inlet connector port 192 to a plug outlet port intersecting the plug periphery 140, here in the form of vertical grooves 320 formed in a plug insert 310 positioned at the distal end 134 of the plug component 130, more about which is said below. As also shown in the exploded perspective view of FIG. 7, a container outlet cap 200 may also be provided for selectively engaging the distal end 54 and external ejection connector port 124 of the container component 50 as disclosed herein.

Figure 7:
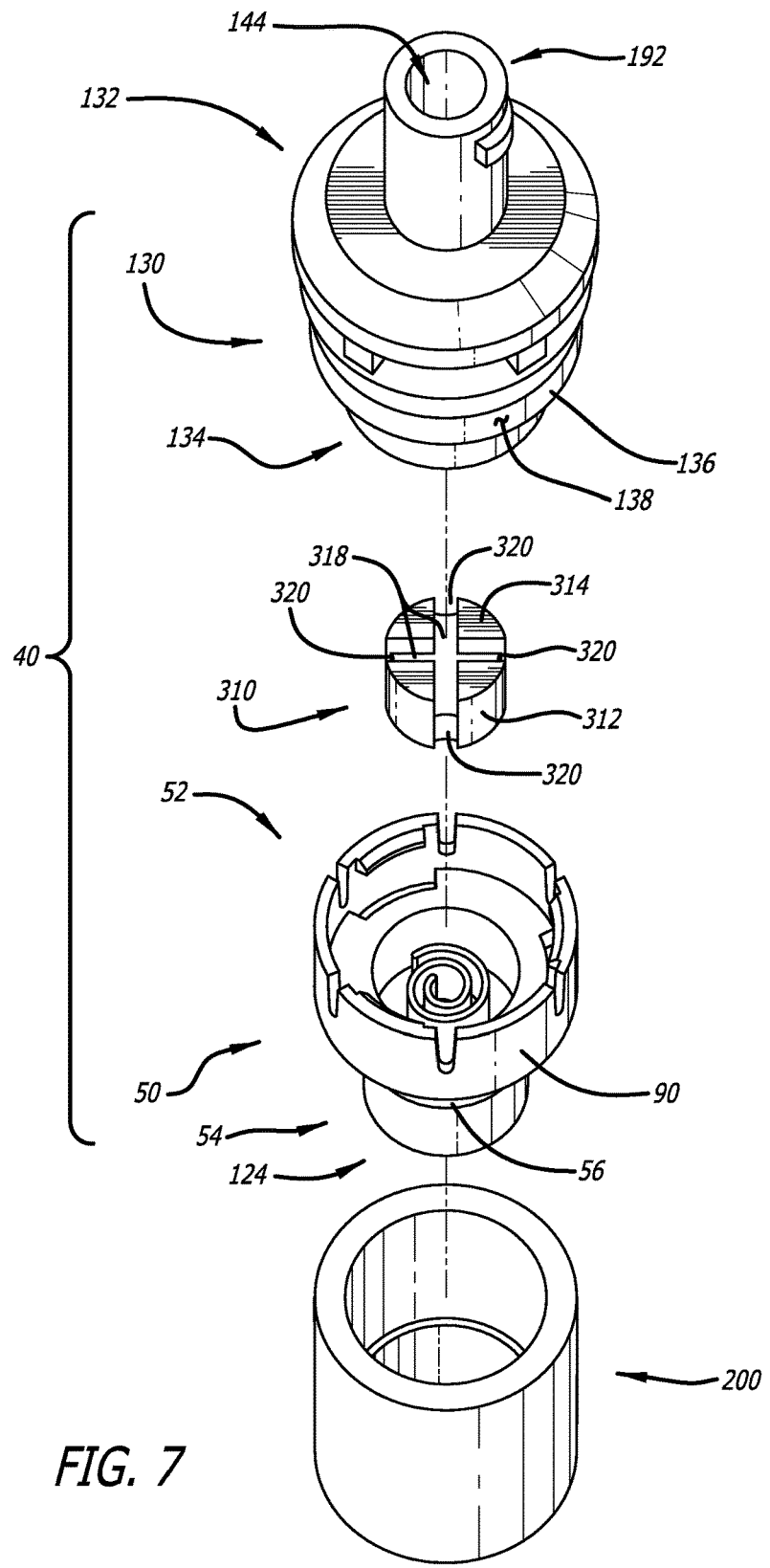
FIG. 7 illustrates an exploded perspective view of an alternative exemplary solution delivery device according to aspects of the present invention.
Figure 10:
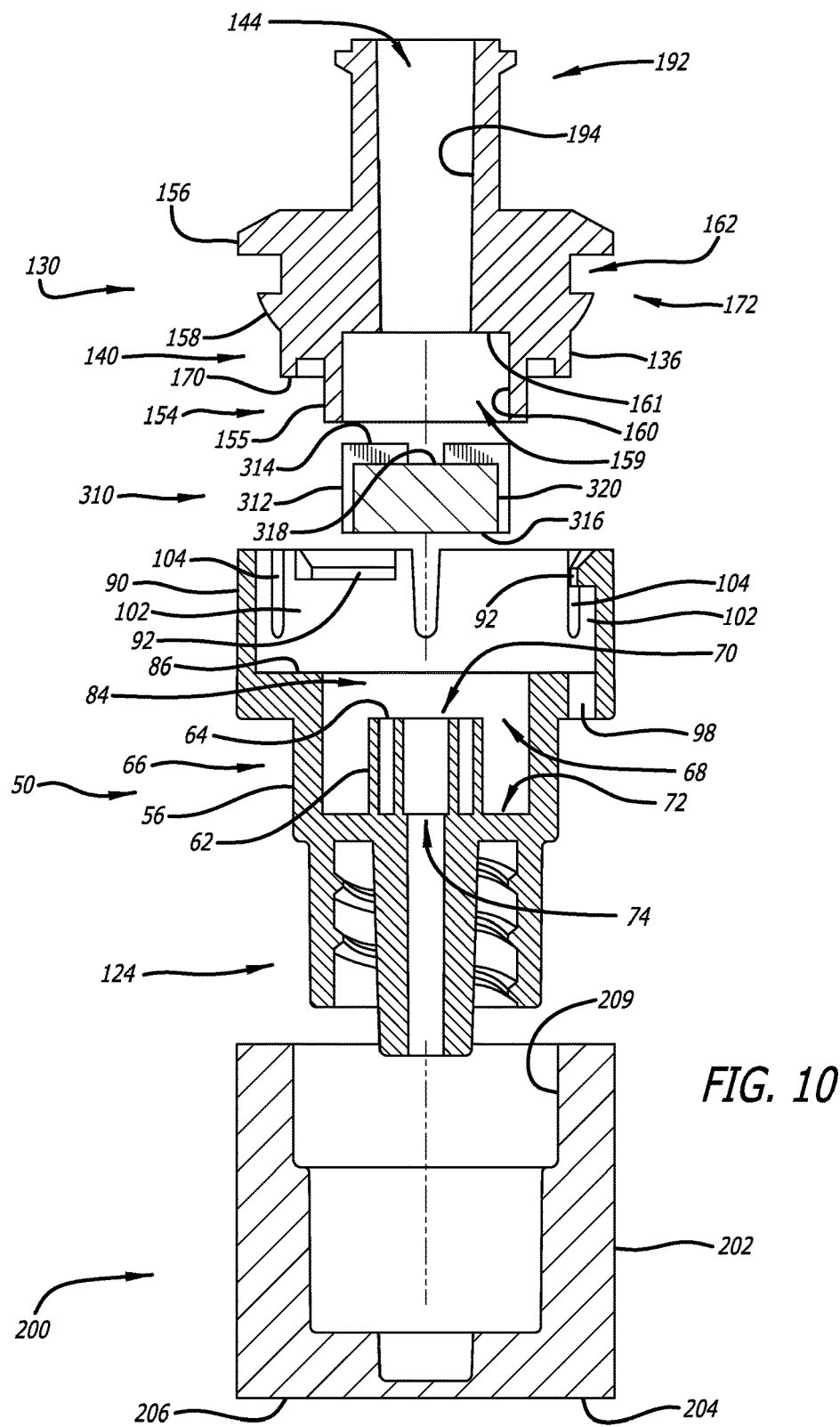
FIG. 10 illustrates an exploded side cross-sectional view thereof.
Figure 11:
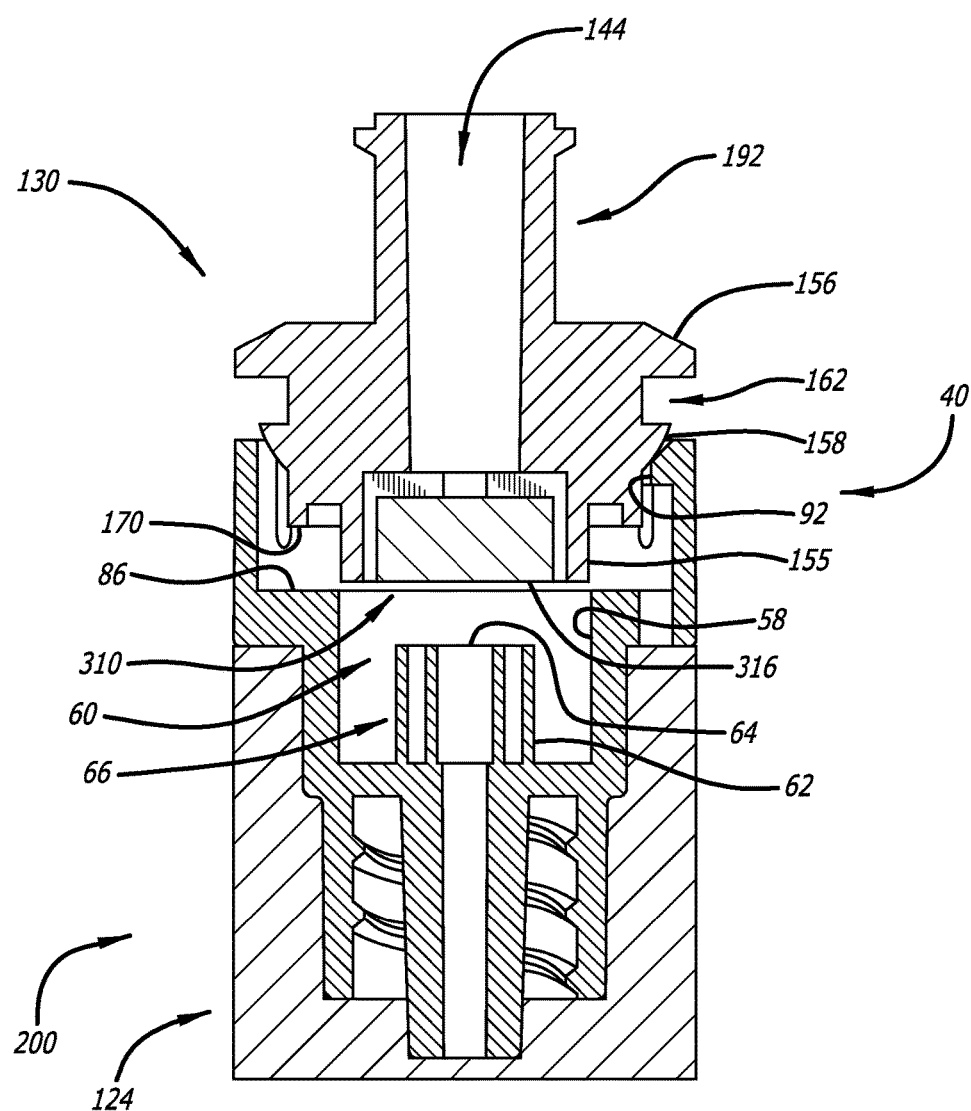
FIG. 11 illustrates an assembled side cross-sectional view thereof in a first mode of operation.
Figure 12:
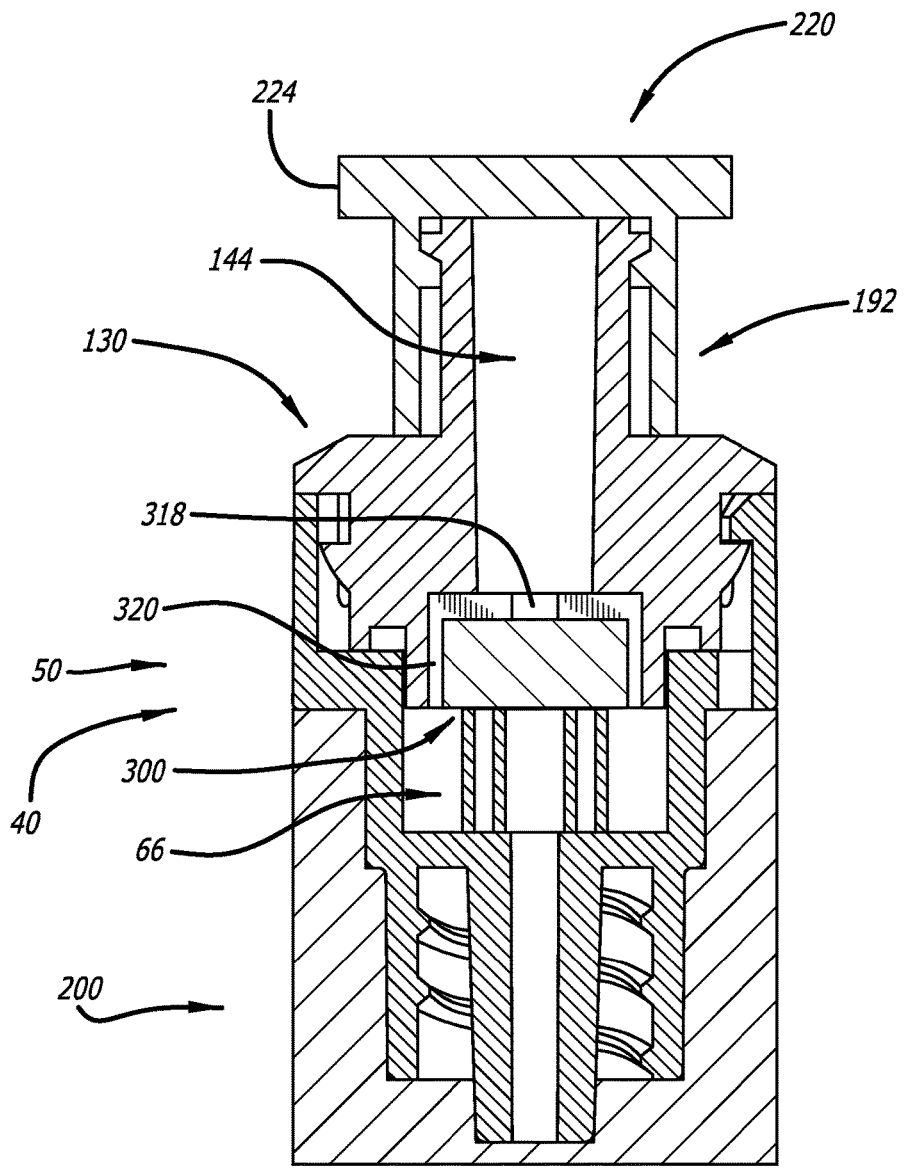
FIG. 12 illustrates an assembled side cross-sectional view thereof in a second mode of operation.

With continued reference to particularly FIG. 7, there is shown a plug insert 310 to be effectively installed between the plug component 130 and the container component 50, more particularly seated within the distal end 134 of the plug component 130 as best seen in FIGS. 10-12. The plug insert 310 is shown as being a substantially annular or cylindrical component, though it will again be appreciated, as noted above and is applicable to all embodiments herein, that while the container and plug components 50, 130 generally are shown as being annular, the invention is not so limited; rather, the components and their various features can take a variety of other geometric shapes and configurations without departing from the spirit and scope of the invention. Relatedly, and as will be appreciated with reference to the numerous alternative embodiments shown and described herein, the particular configurations of the walls, engagement surfaces and features, and sizes and proportions of any such features are merely illustrative of aspects of the present invention and non-limiting. In the particular exemplary plug insert 310 shown in FIG. 7, two horizontal grooves 318 are formed in the top surface 314 substantially perpendicular to each other, so as to form a "plus sign" appearance from above. Further, intersecting and in fluid communication with the horizontal grooves 318 are formed lengthwise vertical grooves 320, four in this case, spaced substantially evenly or at roughly ninety degrees about the outer surface 312 of the plug insert 310, thereby communicating between the insert's top and bottom surfaces 314, 316. It will be appreciated that the cooperation of the horizontal and vertical grooves 318, 320 forms a fluid flow path from the top surface 314 and around the side surfaces 312 of the plug insert 310, even when and particularly when the insert 310 is installed in a matching bore, more about which is said below in connection with FIGS. 10-12. It will be further appreciated that a variety of other groove configurations (number and arrangement, including but not limited to position, shape, and depth) are possible without departing from the spirit and scope of the invention, such that the two horizontal grooves 318 and corresponding four vertical grooves 320 as shown and described are to be understood as merely illustrative and non-limiting. In this exemplary embodiment, it will be appreciated that the four vertical grooves 320 form effectively four plug outlet ports intersecting the plug periphery 140 when the plug insert 310 is inserted within the plug component 130.

Referring to FIG. 8, there is shown an enlarged perspective view of the further exemplary container component 50. Once more, the container component 50 generally comprises a lower base wall 56 and an upper engagement wall 90 forming its body and together defining or bounding, at least in part, the internal cavity 60 of the container component 50. Particularly, it is noted that the inner surface 58 of the base wall 56 is substantially smooth, without any grooves or undercuts. Furthermore, the elongated channel wall 62 that defines the elongated mixing channel 66 (FIG. 10) does not touch the inner surface 58, instead leaving a circumferential path or space within the cavity 60 about the mixing channel 66. As such, those skilled in the art will appreciate that in this alternative embodiment even again without providing any means for indexing the plug component 130 relative to the container component 50, upon assembly of the plug component 130 within the container component 50 in the second operational mode, as shown in FIG. 12, the flow path through the device 40 and particularly through any dried medication or other material in the container component 130 that is to be reconstituted or solubilized is achieved by way of the multiple plug outlet ports formed by the vertical grooves 320 of the plug insert 310 through which a diluent or other solution may flow in use as by being delivered to and through the external inlet connector port 192 and the internal flow path 144 to the plug insert 310 and then into the cavity 60 of the container component 50, the mixing channel 66 thus again providing an indirect flow path between the functional plug outlet port and the ejection connector port 124. As such, in this alternative exemplary embodiment there is no need for the interconnecting groove 76 and/or distribution groove 78 of the first exemplary embodiment of FIGS. 1-6. Even so, it will be further appreciated that the mixing channel 66 still defines an input end 70, or an area where the constituents flow into the channel 66, and an output end 74, or an area where the constituents flow out of the mixing channel 66 into the external ejection connector port 124.

With continued reference to FIG. 8 in conjunction with FIG. 10, the base wall 56 of the container component 50 is shown as terminating proximally in a substantially radially-outwardly extending container flange 86 that transitions to or terminates radially in the proximally extending engagement wall 90, which itself terminates proximally in a radially-inwardly projecting engagement lip 92. In the exemplary embodiment, the radially-inwardly projecting engagement lip 92 is formed on a flexible leg 102 defining a portion of the engagement wall 90 of the container component 50. More particularly, as illustrated, three such flexible legs 102 are formed spaced about the engagement wall 90, as by forming opposite and substantially vertical and parallel notches 104 in the wall 90, with the flexible legs 102 being defined by the upwardly-extending portions of the wall 90 bound by the notches 104 so as to operate like living hinges. It will be appreciated that the container component 50 may thus be configured with virtually any number of flexible legs 102 with proximal, radially-inwardly projecting engagement lips 92, such as two, three as shown here, four as shown in FIGS. 1-6, or more. Other variations including those disclosed herein in connection with alternative embodiments are possible according to aspects of the present invention. As also shown, at least one container vent hole 98 is formed within the container flange 86 radially outwardly of the base wall 56, whereby in the first operational mode of the device 40 with the plug component 130 partially inserted within the container component 50, as shown in FIG. 11, there is fluid communication between the inner cavity 60 of the container component and the surrounding atmosphere at least through the at least one container vent hole 98, assuming some space between the bottom of the flange 86 and the container outlet cap 200; even without substantial venting there, it will be appreciated that the cavity 60 may already vent through the notches 104 and round the engagement lips 92 where there is no contact with the retention lip 158 of the plug component 130, such that the vent holes 98 may not even be necessary and regardless may be formed for other purposes, including manufacturability.

Turning to FIG. 9, the exemplary plug component 130 is shown enlarged and inverted relative to FIG. 7. The outer surface 138 of the side wall 136 of the plug component 130 is formed having a plug seating portion 154 configured to seat against the container seating portion 84 (FIG. 10) of the inner surface 58 of the base wall 56 of the container component 50 upon assembly of the plug component 130 within the container component 50 in the second operational mode as shown in FIG. 12. Here, the plug component 130 further comprises a seating portion wall 155 that defines a downwardly- or distally-opening insert receiving cavity 159 having an inner surface 160 and a top surface 161. It will be appreciated with further reference to FIG. 10 that by forming the inner surface 160 of the insert receiving cavity 159 for a net fit with the outer surface 312 of the plug insert 310 and the top surface 161 of the insert receiving cavity 159 for a net fit with the top surface 314 of the plug insert 310, the cooperation of the horizontal and vertical grooves 318, 320 forms a fluid flow path from the top surface 314 of the insert 310 through the horizontal grooves 318 as bound by the top surface 161 of the cavity 159 and around the side surfaces 312 of the plug insert 310 through the vertical grooves 320 as bound by the inner surface 160 of the cavity 159. As such, the exit of the vertical grooves 320, or where the vertical grooves 320 intersect the plug insert's bottom surface 316 effectively define or form the plug outlet port in this alternative embodiment, such that in the second operational mode the plug outlet port, in the form of the vertical grooves 320, is adjacent to and in fluid communication with container component cavity 60, and the mixing channel 66, specifically, more about which is said below, particularly in connection with FIG. 12. As best seen in FIG. 10, the flow path 144 through the plug component 130 comprises a substantially axial bore 194 formed in the inlet connector port 192 in fluid communication with the insert receiving cavity 159 and from there to the plug outlet port as above-described. It will again be appreciated that a variety of other flow path configurations through the plug component and related configuration and placement of the plug outlet port are possible without departing from the spirit and scope of the invention. An outwardly-opening engagement groove 162 is formed in the outer surface 138 of the side wall 136 of the plug component 130 so as to be selectively engaged by the engagement lip 92 of the container component 50 (FIGS. 8 and 10) during operation of the device 40. In the exemplary embodiment, the engagement groove 162 is formed between a proximal radially-outwardly extending plug flange 156 and a distally offset radially-outwardly projecting retention lip 158. In an alternative embodiment, there is no plug flange, such that the retention lip 158 defines a substantially proximally-facing engagement groove proximally engaged by the engagement lip 92 upon assembly of the plug component 130 within the container component 50 in the second operational mode. As shown, the retention lip 158 is in this exemplary embodiment substantially continuous while the engagement lip 92 is circumferentially associated only with each flexible leg 102 or is thereby discontinuous or discretely formed per leg 102. It will be appreciated that by here forming the retention lip 158 of the plug component 130 to be substantially continuous, no matter the orientation of the plug component 130 relative to the container component 50 the two components may be engaged as by the engagement lips 92 of the one or more flexible legs 102 formed on the container component 50 engaging the substantially continuous retention lip 158 of the plug component 130 when the two components are fully assembled as shown in FIG. 12, and any fluid introduced into the plug component 130 through its inlet connector port 192 and the associated internal flow path 144 will be able to make its way into the mixing channel 66 of the container component 50 due to the plug insert grooves 318, 320 being in fluid communication between the bore 194 and the mixing channel 66. With continued reference to FIGS. 9 and 10, the plug component 130 is further formed having a stepped side wall 136 defined by a distally-facing shoulder 170 separating a relatively larger diameter proximal plug engagement portion 172 from the relatively smaller diameter distal plug seating portion 154. The distance from the engagement lip 92 to the container flange 86 of the container component 50 is substantially equivalent to the distance from the engagement groove 162 to the shoulder 170 of the plug component 130, whereby engagement of the engagement lip 92 within the engagement groove 162 upon assembly of the plug component 130 within the container component 50 in the second operational mode substantially positions the shoulder 170 of the plug component 130 adjacent to the container flange 86 of the container component 50. Though an o-ring is here not shown, one could again be employed between such mating surfaces if desired. Furthermore, the distance from the container flange 86 to the wall top surface 64 of the elongated channel wall 62 installed within the internal cavity 60 of the container component 50 is substantially equivalent to the distance from the shoulder 170 to the distal end 134 of the plug component 130, or the plug distal surface 142, here substantially defined by the bottom surface 316 of the plug insert 310, whereby assembly of the plug component 130 within the container component 50 in the second operational mode such that the engagement lip 92 of the container component 50 is engaged within the engagement groove 162 of the plug component 50 and the shoulder 170 of the plug component 130 is positioned adjacent to the container flange 86 of the container component 50 causes the plug distal surface 142 of the plug component 130, and more specifically the bottom surface 316 of the plug insert 310, to substantially seat against the wall top surface 64 of the elongated channel wall 62 of the container component 50 to substantially close the top 68 of the elongated mixing channel 66 and further causes the plug seating portion 154 of the plug component 130 to seat within the container seating portion 84 of the container component 50 to substantially seal the elongated mixing channel 66 other than the area in fluid communication with the plug outlet port here defined by the vertical grooves 320 of the plug insert 310 installed within the plug component 130.

In use of such a solution delivery device 40 as shown in FIGS. 7-10, in the exemplary context of a liquid medication to be subjected to a lyophilization procedure, it will be appreciated that a first step is essentially to fill the internal cavity 60, and particularly the elongated mixing channel 66, of the container component 50 with the desired amount of liquid to be lyophilized. Preferably, as shown in FIG. 11, the container component 50 has its external ejection connector port 124 capped as by engaging therewith a container outlet cap 200, thereby closing the bottom or distal opening of the container component 50 and thus the device 40. The container outlet cap 200 is configured for selective sealable engagement with the external ejection connector port 124, each of which may be configured as standard luer connectors as are known and used in the art. Alternatively, as shown in FIGS. 10-12, cap 200 may have an inner bore 209 that is stepped to match or provide a net fit relative to the outside of the ejection connector port 124, with the opening of the port 124 closed as by being seated or sealing against the inside of the cap 200. Preferably, the device 40 would remain substantially upright or vertical for the filling step as well as during the subsequent lyophlization procedure. Accordingly, as shown particularly in FIGS. 10 and 11, the container outlet cap 200 has an outlet cap wall 202 terminating distally in an outlet cap base 204 defining an outlet cap base surface 206. Preferably, as shown, the outlet cap base surface 206 is substantially flat or planar so as to be capable of resting flush against a substantially flat or planar horizontal support surface. Instead or additionally, the outlet cap wall 202 may be configured to seat within a receptacle (not shown) or other support structure on a vial fill line and/or within a lyophilization machine. Relatedly, in the exemplary embodiment, the outlet cap wall 202 is substantially coterminous with the container engagement wall 90 when the outlet cap 200 is removably installed on the container component 50. The idea is that the device 40 in at least one embodiment would be capable of standing vertically on the container outlet cap 200, such that the outlet cap perimeter is generally sufficient to permit such self-support or free standing of the device 40. Here, if the outlet cap perimeter has an outlet cap cross-sectional area and the container base wall defines a container perimeter having a container cross-sectional area, the outlet cap cross-sectional area is shown as being approximately equivalent to or 100% of the container cross-sectional area. It will again be appreciated that a variety of other sizes and component proportions are possible according to aspects of the present invention. It will also be appreciated that once so configured with the container outlet cap 200 engaged with or installed on the container component 50 as shown and described, the device 40 may then be placed in any suitable automated, semi-automated, or manual filling machine for the purpose of filling the cavity 60 or particularly the mixing channel 66 with the desired predetermined quantity of liquid. Those skilled in the art will appreciate that a wide variety of sizes or nominal volumes particularly of the predetermined quantity of the first constituent and thus the volume of the cavity 60 and/or the mixing channel 66, accounting for the elongated channel wall 62, are possible within the present invention. In one context, the container component 50 so sized and engaged with the outlet connector cap 200 is positioned for filling without the plug component 130 yet in place as shown in FIG. 11, such that the plug component 130 is subsequently inserted within the container component 50 after the filling step is completed, as again by an automated, semi-automated, or manual process. Alternatively, the filling of the container component 50 can be accomplished even with the plug component 130 partially inserted in the first operational mode of the device 40 as shown in FIG. 11, such as through the inlet connector port 192, as by passing through the flow path 144 and out the plug outlet port defined by the vertical grooves 320 so as to flow down into the cavity 60 of the container component 50.

With continued reference to FIG. 11, there is again shown the device 40 in its first operational mode, wherein the plug component 130 is partially inserted within the container component 50. Specifically, the radially-outwardly projecting retention lip 158 formed on the outer surface 138 of the side wall 136 (FIGS. 9 and 10) of the plug component 130 seats on the radially-inwardly projecting engagement lip 92 formed proximally on the engagement wall 90 of the container component 50. In this position, the shoulder 170 of the plug component 130 is suspended above the container flange 86 of the container component 50 and the plug seating portion 154 (FIGS. 9 and 10) of the plug component 130 is at least partially suspended within the cavity 60 of the container component 50 and is not yet within the container seating portion 84 (FIG. 10), thereby providing clearance between the plug and container components so as to facilitate fluid communication between the internal cavity 60 of the container component 50, and particularly the elongated mixing channel 66, and the surrounding atmosphere through one or more container vent holes 98 and/or through the notches 104 or otherwise around the plug component 130. It will be appreciated by those skilled in the art that in such a first operational mode or position of the device 40, the device may then be subjected to a lyophilization process whereby the interior of the container component 50 can vent or have a vacuum pulled on it or be subjected to any other process that requires fluid flow relative to the liquid to be processed.

Referring now to FIG. 12, once, as in the exemplary context, the lyophlization procedure is complete, the plug component 130 may then be fully inserted within the container component 50 as shown, which may again be accomplished by an automated, semi-automated, or manual process. As shown, a plug inlet cap 220 may be installed on the inlet connector port 192 so as to cap the plug component 130 and thus close off the fluid flow path 144. Such inlet cap 220 may be of any configuration now known or later developed in the art for removable and sealable engagement with the inlet port 192. A flange 224 is shown as being provided on the inlet cap 220 to enhance gripping and manipulation, though those skilled in the art will appreciate that other enhancements such as knurling of the exterior surface of the cap 220 may be employed instead of or in addition to such a flange 224. The inlet cap 220 may be positioned on the inlet connector port 192 before or after the plug component 130 is inserted into the container component 50, and whether in the first operational mode depicted in FIG. 11 or the second operational mode depicted in FIG. 12, though of course the cap 220 is here only shown for illustration on the inlet connector port 192 in FIG. 12 relating to the device 40 in the second operational mode. As described above and will thus be appreciated by those skilled in the art, pushing the plug component 130 all the way into the container component 50 such that, here, the container's engagement lip 92 engages the plug's engagement groove 162 (FIGS. 10 and 11), most notably, the plug distal surface defined by the bottom surface 316 of the plug insert 310 is thus brought into engagement or substantially abutting contact with or otherwise substantially adjacent to the top surface 64 of the wall 62 of the mixing channel 66 (FIG. 10), thereby effectively closing off the mixing channel 66 except for the area substantially fluidly connected to the flow path 144 through the plug component 130 by way of the horizontal and vertical grooves 318, 320 of the plug insert 310. Once again, flowing a second constituent into the device 40 as through the inlet connector port 192 and associated flow path 144 of the plug component 130 allows such second constituent to exit the plug outlet port defined by the vertical grooves 320 and flow into the mixing channel 66 so as to then reconstitute the previously lyophilized first constituent housed within the mixing channel 66, once again without any separate mixing, shaking, priming, or other reconstitution step. Relatedly, when the plug component 130 is thus seated within the container component 50 so as to configure the device 40 in the second operational mode, the plug shoulder 170 is brought adjacent to the container flange 86 so as to seal therebetween as by a net fit and thereby seal off the container vent holes 98 and completely bound the cavity 60 such that any second constituent entering the device 40 and making its way into the interior cavity 60 of the container component 50 can only then flow into the mixing channel 66 and not back out of the device 40 through any other path, thus again forcing the reconstitution of the first constituent or the mixing of the first and second constituents within the mixing channel 66. Relatedly, if the cavity 60 is effectively sealed "above" by the engagement between the plug shoulder 170 and the container flange 86, then it is effectively sealed "below" through the engagement between the plug seating portion 154 and the container seating portion 84. In the exemplary embodiment, the effective engagement between these surfaces is again a net-fit arrangement. Particularly, the two surfaces or seating portions 84, 154 are here shown as substantially straight annular walls configured to be brought into substantially abutting contact upon full assembly of the plug component 130 within the container component 50. It will be appreciated by those skilled in the art, with further reference to the numerous alternative embodiments presented herein, that a variety of other configurations and interoperability of the components of a solution delivery device according to aspects of the present invention are thus possible without departing from its spirit and scope. It is further noted in connection with putting the device 40 into the second operational mode shown in FIG. 12, or shifting the device 40 from the first operational mode as shown in FIG. 11 to the second operational mode as shown in FIG. 12, that the flexible legs 102 of the container component 50 on which are formed the engagement lips 92 allow the lips 92 to deflect or shift radially outwardly to pass over the retention lip 158 and then spring or seat into the plug engagement groove 162. In the exemplary embodiment of FIGS. 7-12, each flexible leg 102 is attached to the engagement wall 90 along a lower edge so as to function as a living hinge, such that the geometric or mechanical design along with the selection of an appropriate medical grade plastic with sufficient elasticity enables the requisite flexibility and functionality. Moreover, as can be seen and will be appreciated, the engaging or opposed surfaces of the respective engagement lip 92 and retention lip 158 are sloped so as to effectively provide a ramp along which the engagement lip 92 travels as it shifts radially outwardly as the plug component 130 is advanced distally within or relative to the container component 50 until the engagement lip 92 clears the retention lip 158 proximally and seats within the engagement groove 162 to effectively lock the plug component 130 within the container component 50 in the configuration of the device 40 shown in FIG. 12. As will also be appreciated from FIG. 12, in the exemplary embodiment the plug flange 156 defines a plug perimeter that is substantially radially coterminous with the engagement wall 90 of the container component 50 for a substantially flush fit between the plug and container components when the device 40 is in its second operational mode as shown.

Turning now to FIGS. 13-18, there is shown a third exemplary solution delivery device 40 according to aspects of the present invention. The device 40 again generally comprises a container component 50 having an open proximal end 52 and an opposite distal end 54 at which is formed an external ejection connector port 124 and a plug component 130 configured to be inserted at least partially within the open end 52 of the container component 50. The plug component 130 is generally configured for selective engagement with the container component 50 in at least first and second operational modes, the plug component 130 having a proximal end 132, an opposite distal end 134, and a side wall 136 having an outer surface 138 disposed between the ends, the side wall 136 and distal end 134 together defining a plug periphery 140. The plug component has an external inlet connector port 192 substantially at the proximal end 132 and an internal flow path 144 from the inlet connector port 192 to a plug outlet port 146 intersecting the plug periphery 140. It will again be appreciated by those skilled in the art, with reference to the numerous alternative embodiments shown and described herein, that the particular configurations of the walls, engagement surfaces and features, and sizes and proportions of any such features are merely illustrative of aspects of the present invention and non-limiting.

Figure 16:
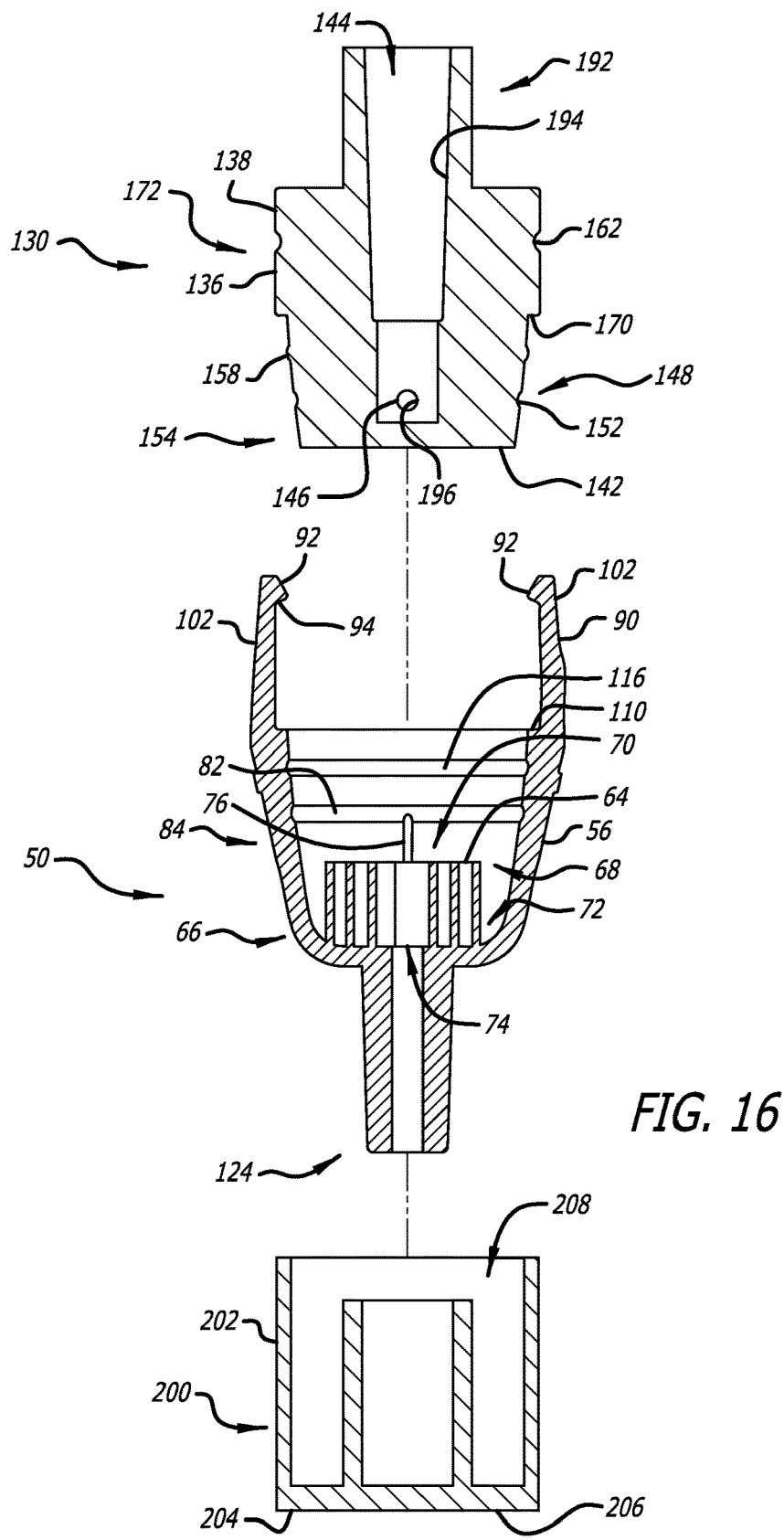
FIG. 16 illustrates an exploded side cross-sectional view thereof.

Referring to FIGS. 14 and 16, the container component 50 is formed with a lower base wall 56 having an inner surface 58 and defining an internal cavity 60 with a size selected to contain a predetermined quantity of a first constituent. Within the cavity 60 there is formed or installed an elongated channel wall 62 to form an elongated mixing channel 66 having a substantially open top 68 and a substantially closed bottom 72. Nearer to the open top 68 of the mixing channel 66 and substantially adjacent the inner surface 58 of the base wall 56 there is formed or defined a channel input end 70 in fluid communication with the plug outlet port 146 when the device 40 is in its second operational mode and an opposite output end 74 in fluid communication with the ejection connector port 124, more about which is said below, particularly in connection with FIG. 18. In the illustrated embodiment, the container component 50 further comprises an interconnecting groove 76 formed in the inner surface 58 of the base wall 56 so as to be in fluid communication with the input end 70 of the mixing channel 66. Preferably, the interconnecting groove 76 is substantially lengthwise along the container component base wall 56, though it will be appreciated that other orientations of the groove 76 may also be employed. The interconnecting groove 76 is of sufficient length to be in fluid communication with the plug outlet port 146 upon assembly of the plug component 130 within the container component 50 in the second operational mode, as shown in FIG. 18, whereby the mixing channel 66 provides an indirect flow path between the plug outlet port 146 and the ejection connector port 124. The container component 50 further generally comprises a distribution groove 78 formed in the inner surface 58 of the base wall 56 so as to be in fluid communication with the interconnecting groove 76. In the alternative exemplary embodiment shown, the distribution groove 78 is configured as a radially inwardly-opening circumferential recess 82 in the inner surface 58 of the base wall 56, positioned in the inner surface 58 proximal of the channel wall top surface 64 so as to form a container seating portion 84 of the inner surface 58 between the recess 82 and the mixing channel 66, more about which is said below regarding the device 40 in use. In the exemplary embodiment as shown, once again, the container component 50 being substantially annular, it follows, though not necessarily so, that the distribution groove 78 here defined by the recess 82 formed within the container component lower wall 56 is also substantially annular. Furthermore, as illustrated, the distribution groove is substantially continuous, though once more, there are configurations of the device in which there may not be a distribution groove or if there is it may not be continuous. Those skilled in the art will again appreciate that a variety of such components and configurations are possible without departing from the spirit and scope of the invention.

With continued reference to FIGS. 14 and 16, the base wall 56 of the container component 50 is shown as terminating in the proximally extending engagement wall 90, which itself terminates proximally in a radially-inwardly projecting engagement lip 92. In the alternative exemplary embodiment, the radially-inwardly projecting engagement lip 92 is formed on a flexible leg 102 defining effectively the entirety of the engagement wall 90 of the container component 50. More particularly, as illustrated, a pair of opposed proximally-extending flexible legs 102 are formed as the engagement wall 90 so as to operate like living hinges. As shown, the base wall 56 and the engagement wall 90 are thus substantially contiguous, though it will be appreciated that a flange or other exterior step may be formed at the transition between base wall 56 and the engagement wall 90 as in other exemplary embodiments shown and described herein. In fact, as best seen in FIG. 16, the container component 50 may be effectively formed with a proximally-facing container shoulder 110 defining the top of the base wall 56 and configured for engagement with a distally-facing plug shoulder 170 when the plug component 130 is fully inserted within the container component 50. Those skilled in the art will again appreciate that the container component 50 may thus be configured having a variety of geometrical components and arrangements for the operable receipt of the plug component 130. Again, the legs 102 and/or the lips 92 themselves may be flexible and configured for shifting relative to the plug component 130 as it is inserted within the container component 50. As also shown, at least one container vent hole 98 is formed within the container flange 86 radially outwardly of the base wall 56, whereby in the first operational mode of the device 40 with the plug component 130 partially inserted within the container component 50, as shown in FIG. 11, there is fluid communication between the inner cavity 60 of the container component and the surrounding atmosphere at least through the at least one container vent hole 98. In the exemplary embodiment, the size and locations of the vent holes substantially correspond to the locations of the legs 102 and related lips 92, as might result from or be accomplished through an injection molding process with a core pull to simultaneously form each vent hole 98 and undercut of the respective engagement lip 92, though it will be appreciated that a wide variety of configurations and locations of such vent holes is possible without departing from the spirit and scope of the invention.

Figure 13:
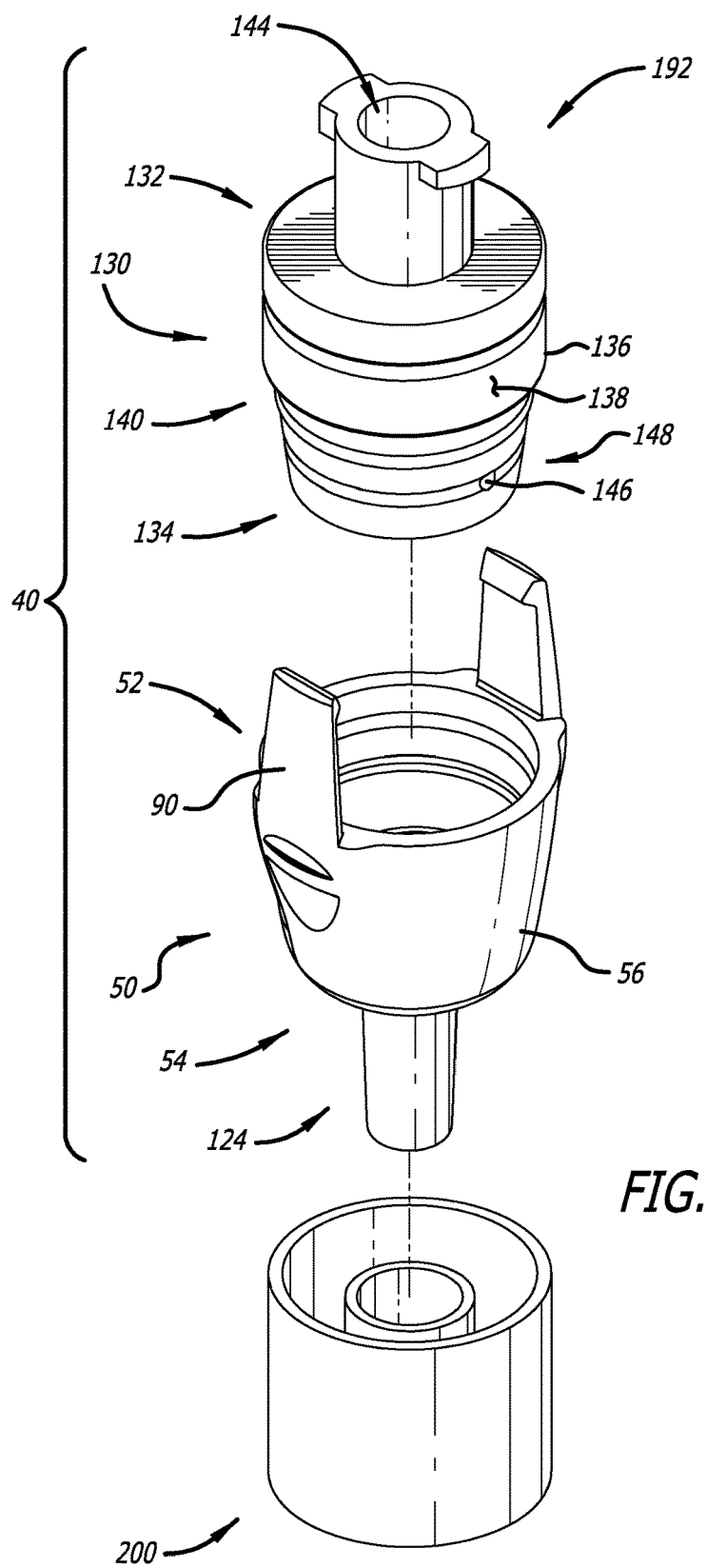
FIG. 13 illustrates an exploded perspective view of an alternative exemplary drug delivery device according to aspects of the present invention.

Turning to FIGS. 15 and 16, the plug component 130 of the alternative exemplary embodiment of the solution delivery device 40 according to aspects of the present invention is shown enlarged and inverted relative to FIG. 13. The outer surface 138 of the side wall 136 of the plug component 130 is formed having a distal plug seating portion 154 configured to seat against the container seating portion 84 (FIG. 16) of the inner surface 58 of the base wall 56 of the container component 50 upon assembly of the plug component 130 within the container component 50 in the second operational mode as shown in FIG. 18. The plug outlet port 146 is located in the side wall 136 proximal of the plug seating portion 154, such that in the second operational mode the plug outlet port 146 is adjacent to and in fluid communication with the distribution groove 78 formed in the container component 50, here as by the recess 82 in the bore of the container component 50 (FIGS. 14 and 16), more about which is said below, particularly in connection with FIG. 18. Furthermore, in the alternative exemplary embodiment, the plug component 130 further comprises a distribution groove 148 of its own formed in the outer surface 138 of the side wall 136 as an outwardly-opening circumferential recess 152 so as to be in fluid communication with the plug outlet port 146; that is, the plug outlet port 146 is effectively formed in or intersects the plug distribution groove 148 or plug recess 152. Accordingly, it will be appreciated that the respective container and plug distribution grooves 78, 148 are substantially co-planar when the plug component 130 is fully seated within the container component 50 so as to have the plug outlet port 146 in fluid communication with both, thus each with the other so as to form the overall distribution groove within which the second constituent may flow after exiting the plug outlet port 146 as it makes its way to the interconnecting groove 76 and the input end 70 of the mixing channel 66 (FIGS. 14 and 16). As best seen in FIG. 16, the flow path 144 through the plug component 130 comprises a substantially axial bore 194 formed in the inlet connector port 192 intersected by and in fluid communication with a substantially transverse bore 196 defining the plug outlet port 146. It will be appreciated that a variety of other flow path configurations through the plug component and related placement of the plug outlet port 146 are possible without departing from the spirit and scope of the invention. As in the embodiment of FIGS. 1-6, an outwardly-opening engagement groove 162 is formed in the outer surface 138 of the side wall 136 of the plug component 130 proximal of the plug outlet port 146 and recess 152 so as to be selectively engaged by the engagement lips 92 of the container component 50 during operation of the device 40, particularly in the first operational mode shown in FIG. 17, more about which is said below. With continued reference to FIGS. 15 and 16, the plug component 130 is further formed having a stepped side wall 136 defined by a distally-facing shoulder 170 separating a relatively larger diameter proximal plug engagement portion 172 from the relatively smaller diameter distal plug seating portion 154, which shoulders 110, 170 are configured for engagement or abutment when the device 40 is in its second operational mode as shown in FIG. 18.

In use of such a solution delivery device 40 as shown in FIGS. 13-16, again in the exemplary context of a liquid medication to be subjected to a lyophilization procedure, as shown in FIGS. 17 and 18, the container component 50 has its external ejection connector port 124 capped as by engaging therewith a container outlet cap 200, thereby closing the bottom or distal opening of the container component 50 and thus the device 40. The container outlet cap 200 may be configured for selective sealable engagement with the external ejection connector port 124, and though not shown, each of which may be configured as standard luer connectors as are known and used in the art. The outlet cap 200 again provides for sealing and integrity of the ejection connector port 124, with or without an internal membrane (not shown) or other seal, and for facilitating the filling and lyophilization processes. Preferably, the device 40 would remain substantially upright or vertical for the filling step as well as during the subsequent lyophlization procedure. Accordingly, as shown particularly in FIGS. 17 and 18, the container outlet cap 200 has an outlet cap wall 202 terminating distally in an outlet cap base 204 defining an outlet cap base surface 206. As shown, the outlet cap base surface 206 is substantially flat or planar so as to be capable of resting flush against a substantially flat or planar horizontal support surface. Instead or additionally, the outlet cap wall 202 may be configured to seat within a receptacle (not shown) or other support structure on a vial fill line and/or within a lyophilization machine. Relatedly, in the exemplary embodiment, the outlet cap wall 202 is substantially coterminous with the container base wall 56 when the outlet cap 200 is removably installed on the container component 50. The idea once more is that the device 40 in at least one embodiment would be capable of standing vertically on the container outlet cap 200, such that the outlet cap perimeter is generally sufficient to permit such self-support or free standing of the device 40. It will also be appreciated that once so configured with the container outlet cap 200 engaged with or installed on the container component 50 as shown and described, the device 40 may then be placed in any suitable automated, semi-automated, or manual filling machine for the purpose of filling the cavity 60 or particularly the mixing channel 66 with the desired predetermined quantity of liquid.

With continued reference to FIG. 17, there is again shown the device 40 in its first operational mode, wherein the plug component 130 is partially inserted within the container component 50. Specifically, the radially-inwardly projecting retention lips 92 formed integrally with the resilient legs 102 of the engagement wall 90 of the container component 50 temporarily engage or seat within the plug engagement groove 162 on the outer surface 138 of the side wall 136 (FIGS. 15 and 16) of the plug component 130. In this position, the shoulder 170 of the plug component 130 is suspended above the shoulder 110 of the container component 50 and the plug seating portion 154 (FIGS. 15 and 16) of the plug component 130 is at least partially suspended within or adjacent to the distribution groove 78 formed as an inwardly-opening recess 82 in the inner surface 58 of the base wall 56 of the container component 50 and is not yet within the container seating portion 84 (FIG. 16), thereby providing clearance between the plug and container components so as to facilitate fluid communication between the internal cavity 60 of the container component 50, and particularly the elongated mixing channel 66, and the surrounding atmosphere. It will be appreciated by those skilled in the art that in such a first operational mode or position of the device 40, the device may then be subjected to a lyophilization process whereby the interior of the container component 50 can vent or have a vacuum pulled on it or be subjected to any other process that requires fluid flow relative to the first constituent liquid to be processed.

Referring now to FIG. 18, when the illustrative lyophilization procedure or other such procedure is complete, the plug component 130 may then be fully inserted within the container component 50 as shown, which may again be accomplished by an automated, semi-automated, or manual process. In the alternative exemplary embodiment, pushing the plug component 130 all the way into the container component 50 such that, here, the container's engagement lip 92 engages the proximal end 132 of the plug component 130 (FIG. 17), most notably, the plug distal surface 142 (FIG. 15) is thus brought into engagement or substantially abutting contact with or otherwise substantially adjacent to the top surface 64 of the wall 62 of the mixing channel 66 (FIGS. 14 and 16), thereby effectively closing off the mixing channel 66 except for its input end 70 (FIG. 14) substantially fluidly connected to the flow path 144 through the plug component 130. Particularly, as shown, the proximal end 132 of the plug component 130 is formed having a proximally-facing plug proximal surface 176, and the engagement lip 92 is formed having a substantially distally-facing lip distal surface 94 configured to seat against the plug proximal surface 176 when the plug component 130 is fully seated within the container component 150 in the second operational mode of the device 40. Once again, more about the device 40 so configured in its second operational mode post-lyophilization in various exemplary contexts and clinical uses and hence various constituents within the device 40 are all discussed further below, particularly in connection with FIGS. 40-42, but here it is sufficient to note that flowing a second constituent into the device 40 as through the inlet connector port 192 and associated flow path 144 of the plug component 130 allows such second constituent to exit the plug outlet port 146, fill the substantially adjacent container and plug distribution grooves 78, 148, and then find its way into the mixing channel 66 through the longitudinal interconnecting groove 76 (FIGS. 14-16) that is somewhat contiguous with the mixing channel input end 70 (FIG. 2) so as to then reconstitute the previously lyophilized first constituent housed within the mixing channel 66, once again without any separate mixing, shaking, priming, or other reconstitution step. Relatedly, when the plug component 130 is thus seated within the container component 50 so as to configure the device 40 in the second operational mode, the plug shoulder 170 is brought adjacent to the container shoulder 110 so as to further seat the components together and help seal off the container interior cavity 60. That is, in the exemplary embodiment, the distance from each engagement lip 92 to the container shoulder 110 is substantially equivalent to the distance from the engagement groove 162 to the shoulder 170 of the plug component 130, whereby engagement of the engagement lip 92 within the engagement groove 162 upon assembly of the plug component 130 within the container component 50 in the second operational mode substantially positions the shoulder 170 of the plug component 130 adjacent to the shoulder 110 of the container component 50. Moreover, in the exemplary embodiment, a radially-outwardly projecting retention lip 158 is formed on the outer surface 138 of the side wall 136 of the plug component 130 and configured for engagement with a corresponding radially-inwardly opening retention groove 116 formed in the inner surface 58 of the base wall 56 of the container component 50 in the second operational mode of the device 40. As illustrated, both the retention groove 116 and the retention lip 158 are positioned proximal of the respective container and plug distribution grooves 78, 148. It will be appreciated that such retention lip-groove engagement when the plug component 130 is fully inserted within the container component 50 serves to further lock the two components together as well as to seal off the internal cavity 60 and particularly the mixing channel 66 and the distribution grooves 78, 148 in communication therewith through the interconnecting groove 76. Accordingly, any second constituent entering the device 40 and making its way into the interior cavity 60, and particularly the distribution grooves 78, 148, of the respective container and plug components 50, 130 can only then flow into the mixing channel 66 through the interconnecting groove 76 and not back out of the device 40 through any other path or into the mixing channel 66 anywhere but substantially at its input end 70, thus again forcing the reconstitution of the first constituent or the mixing of the first and second constituents within the mixing channel 66. Relatedly, if the distribution grooves 78, 148 are effectively sealed "above" by the seating of the shoulders 110, 170 and the engagement of the retention lip 158 within the retention groove 116, then the grooves 78, 148 are effectively sealed "below" through the engagement between the plug seating portion 154 and the container seating portion 84. In the exemplary embodiment, the effective engagement between these surfaces is a net-fit arrangement. Particularly, the two surfaces or seating portions 84, 154 are here shown as somewhat tapered annular walls configured to be brought into substantially abutting contact upon full assembly of the plug component 130 within the container component 50. It will be appreciated by those skilled in the art, with further reference to the numerous alternative embodiments presented herein, that a variety of other configurations and interoperability of the components of a solution delivery device according to aspects of the present invention are thus possible without departing from its spirit and scope. For example, once more, the engagement surfaces between the container and plug components may also be substantially straight-walled or curve-walled. It is further noted in connection with putting the device 40 into the second operational mode shown in FIG. 18, or shifting the device 40 from the first operational mode as shown in FIG. 17 to the second operational mode as shown in FIG. 18, that the flexible legs 102 of the container component 50 on which are formed the engagement lips 92 allow the lips 92 to deflect or shift radially outwardly to pass over the outside surface 138 of the plug component, particularly over the shoulder 170, and then in and out of the engagement groove 162 before springing back into place over or abutting the proximal end 132 of the plug component 130. In the exemplary embodiment of FIGS. 13-18, each flexible leg 102 is attached to the engagement wall 90 along a lower edge so as to function as a living hinge, such that the geometric or mechanical design along with the selection of an appropriate medical grade plastic with sufficient elasticity enables the requisite flexibility and functionality. As shown, with the proximal plug surface 176 in this exemplary embodiment being substantially continuous, no matter the orientation of the plug component 130 relative to the container component 50 the two components may be engaged and retained in such assembled state by virtue of the engagement lips 92 snapping over the plug proximal end 132 and any fluid introduced into the plug component 130 through its inlet connector port 192 and the associated internal flow path 144 will be able to make its way into the mixing channel 66 of the container component 50 due to the plug outlet port 146 being in fluid communication with the interconnecting groove 76, and hence the mixing channel 66, through the substantially continuous distribution grooves 78, 148 of the components.

Figure 19:
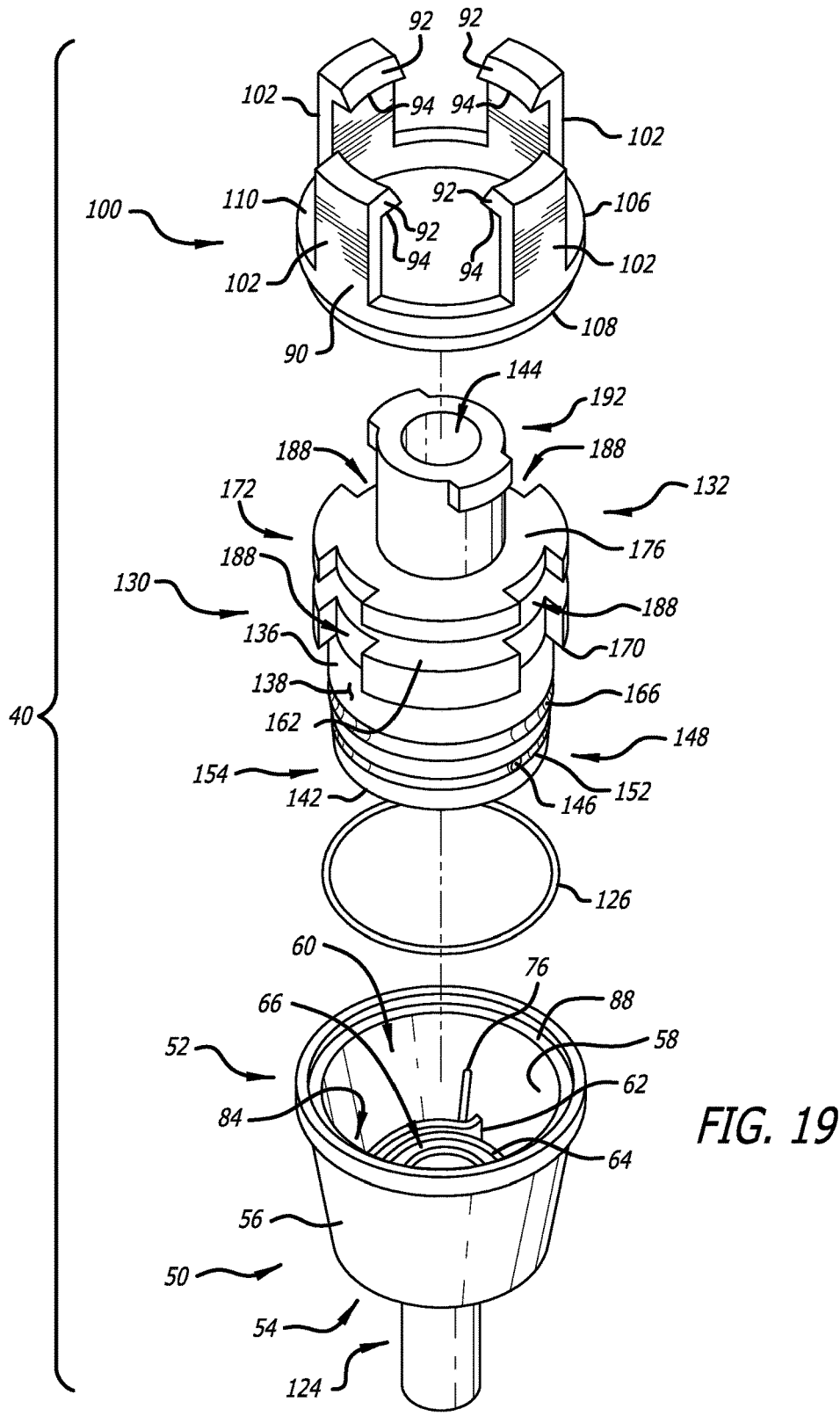
FIG. 19 illustrates an exploded perspective view of a further alternative exemplary drug delivery device according to aspects of the present invention.
Figure 20:
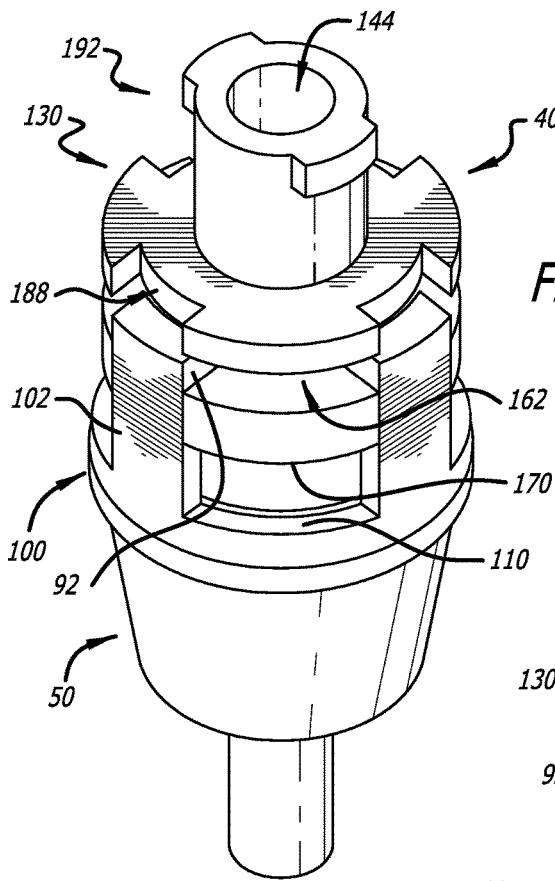
FIG. 20 illustrates an enlarged assembled perspective view thereof in a first mode of operation.
Figure 21:
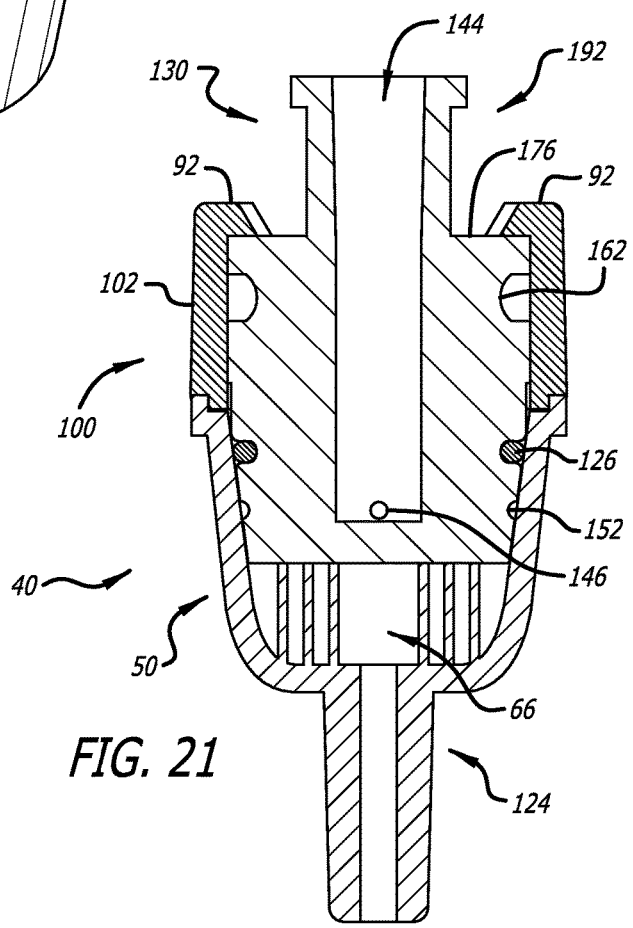
FIG. 21 illustrates an enlarged assembled side cross-sectional view thereof in a second mode of operation.

Turning now to FIGS. 19-21, there is shown a further alternative exemplary embodiment similar to that of FIGS. 13-18, though with several notable differences. With reference to the exploded perspective view of FIG. 19, it can be seen that here the engagement portion or wall 90 is formed separately from the container component 50 and its base wall 56. Particularly, there is provided a separate engagement component 100 having a base engagement ring 106 from which extend substantially proximally the one or more resilient legs 102 formed proximally with radially-inwardly projecting engagement lips 92. In the alternative embodiment shown, the engagement component 100 is formed having four spaced-apart legs 102, though once again those skilled in the art will appreciate that a variety of legs 102 in configuration and number is possible. Substantially between the legs 102 the proximally-facing surface of the engagement ring 10 defines the container shoulder 110. The engagement ring 106 is further formed having a substantially distally-facing ring step 108 configured to engage a substantially proximally-facing base wall step 88 of the container component 50, as best shown in FIG. 21. Those skilled in the art will appreciate that the assembly of the engagement component 100 onto the container component 50 as by engagement of the respective ring and base wall steps 108, 88 may be accomplished through an interference fit, ultrasonic welding, solvent bonding, or any other such assembly technique now known or later developed in the art. The container component 50 is otherwise similar to that in other embodiments, particularly once the engagement component 100 is assembled thereon to effectively form the upper engagement wall 90 of the container component 50, it also having a base wall 56 having an inner surface 58 and defining an internal cavity 60 with a size selected to contain a predetermined quantity of a first constituent. Within the cavity 60 there is again formed or installed an elongated channel wall 62 to form an elongated mixing channel 66. An interconnecting groove 76 is also formed in the inner surface 58 of the base wall 56 so as to be in fluid communication between the distribution groove 148 formed as a radially-outwardly opening recess 152 in the plug component 130 and the mixing channel 66 of the container component 50 upon assembly of the plug component 130 within the container component 50 in the second operational mode, as shown in FIG. 21, whereby the mixing channel 66 provides an indirect flow path between the plug outlet port 146 and the ejection connector port 124. Here, the container component 50 does not include a separate distribution groove formed in the inner surface 58 of the base wall 56 as in other alternative embodiments, such that only the plug distribution groove 148 provides the function of fluidly connecting the plug outlet port 146 and the interconnecting groove 76. Regarding the plug component 130, the outer surface 138 of the side wall 136 is again formed having a radially-outwardly opening recess 152 defining the distribution groove 148, with the plug outlet port 146 located in the side wall 136 so as to intersect and be in fluid communication with the distribution groove 148 or plug recess 152. As in the embodiments of FIGS. 1-18, an outwardly-opening engagement groove 162 is formed in the outer surface 138 of the side wall 136 of the plug component 130 proximal of the plug outlet port 146 and recess 152 so as to be selectively engaged by the engagement lips 92 of the container component 50 during operation of the device 40, particularly in the first operational mode shown in FIG. 20, more about which is said below. The plug component 130 is further formed having a stepped side wall 136 defined by a substantially distally-facing shoulder 170 separating a relatively larger diameter proximal plug engagement portion 172 from the relatively smaller diameter distal plug seating portion 154, with the shoulder 170 configured for engagement or abutment relative to the container shoulder 110 formed as the proximally-facing surface of the engagement ring 106 of the engagement component 100 when the device 40 is in its second operational mode as shown in FIG. 21. Particularly, in the exemplary alternative embodiment, there are formed in the plug outer surface 138, and specifically the proximal plug engagement portion 172, substantially lengthwise plug cut-outs 188 corresponding to the size and location of the flexible engagement legs 102 so as to thereby provide clearance for the legs 102 as well as in indexing function in some embodiments. As shown, the cut-outs 188 extend lengthwise across the otherwise relatively larger proximal plug engagement portion 172 so as to render the thickness or part diameter within the cut-outs 188 substantially equivalent to that of the distal plug seating portion 154, particularly at the shoulder 170, or the transition between the distal seating portion 154 and the proximal engagement portion 172.

Referring to FIGS. 20 and 21 depicting the exemplary solution delivery device 40 in its first and second operational modes, as a threshold matter, it is noted that for convenience and clarity neither the container outlet cap 200 (FIGS. 1, 7 and 13) nor the plug inlet cap 220 (FIGS. 6 and 12) are shown, though it will be appreciated that both will be employed generally as described herein. In use of such a solution delivery device 40 as shown in FIG. 19, again in the exemplary context of a liquid medication to be subjected to a lyophilization procedure, the device 40 may be placed in any suitable automated, semi-automated, or manual filling machine for the purpose of filling the cavity 60 or particularly the mixing channel 66 (FIG. 19) with the desired predetermined quantity of liquid first constituent. Before or after that step, though most often after, the plug component 130 is again then inserted partway into the container component 50 as shown here in FIG. 20 so as to put the device 40 in the first operational mode as when it is to be placed in a lyophilizer or otherwise be processed. Particularly, it is noted that the radially-inwardly projecting engagement lips 92 formed proximally on the flexible legs 102 of the container engagement component 100 temporarily engage or seat within the plug engagement groove 162 on the outer surface 138 of the side wall 136 (FIG. 19) of the plug component 130 as by the legs 102 flexing radially outwardly as the plug component 130 is advanced distally within the container component 150 and thus the engagement lips 92 are shifted proximally within the plug cut-outs 188 until the lips 92 enter the plug engagement groove 162 substantially as shown in FIG. 20. In this position, the shoulder 170 of the plug component 130 is suspended above the shoulder 110 of the container component 50 and the plug seating portion 154 of the plug component 130 is not yet seated or engaged with the container seating portion 84 (FIG. 19), thereby providing clearance between the plug and container components so as to facilitate fluid communication between the internal cavity 60 of the container component 50, and particularly the elongated mixing channel 66, and the surrounding atmosphere. It will be appreciated by those skilled in the art that in such a first operational mode or position of the device 40, the device may then be subjected to a lyophilization process whereby the interior of the container component 50 can vent or have a vacuum pulled on it or be subjected to any other process that requires fluid flow relative to the first constituent liquid to be processed. Then, as shown in FIG. 21, when the illustrative lyophlization procedure or other such procedure is complete, the plug component 130 may then be fully inserted within the container component 50, which may again be accomplished by an automated, semi-automated, or manual process. In the alternative exemplary embodiment, pushing the plug component 130 all the way into the container component 50 such that, here, the container's engagement lip 92 engages the proximal end 132 of the plug component 130 (FIG. 19), the plug distal surface 142 is thus brought into engagement or substantially abutting contact with or otherwise substantially adjacent to the top surface 64 of the wall 62 of the mixing channel 66 (FIG. 19), thereby effectively closing off the mixing channel 66 except for its input end in the vicinity of the interconnecting groove 76 (FIG. 19). Particularly, as shown, the proximal end 132 of the plug component 130 is formed having a proximally-facing plug proximal surface 176, and the engagement lip 92 is formed having a substantially distally-facing lip distal surface 94 configured to seat against the plug proximal surface 176 when the plug component 130 is fully seated within the container component 150 in the second operational mode of the device 40. Once again, more about the device 40 so configured in its second operational mode post-lyophilization in various exemplary contexts and clinical uses and hence various constituents within the device 40 are all discussed further below, particularly in connection with FIGS. 40-42, but here it is sufficient to note that flowing a second constituent into the device 40 as through the inlet connector port 192 and associated flow path 144 of the plug component 130 allows such second constituent to exit the plug outlet port 146, fill or flow into the plug distribution groove 148, and then find its way into the mixing channel 66 through the longitudinal interconnecting groove 76 (FIG. 19) so as to then reconstitute the previously lyophilized first constituent housed within the mixing channel 66, once again without any separate mixing, shaking, priming, or other reconstitution step. Relatedly, when the plug component 130 is thus seated within the container component 50 so as to configure the device 40 in the second operational mode, the plug shoulder 170 is brought adjacent to the container shoulder 110 so as to further seat the components together and help seal off the container interior cavity 60. Moreover, in the exemplary embodiment, an o-ring 126 is seated in an o-ring groove 166 formed in the outer surface 138 of plug side wall 136 between the distal distribution groove 148 or recess 152 and the proximal engagement groove 162 and shoulder 170 (FIG. 19). It will be appreciated that in the second operational mode with the plug component 130 fully inserted within the container component 50, the o-ring 126 forms a seal effectively between the inner surface 58 of the container component 50 and the outer surface 138 of the plug component 130 and thus serves to seal off the internal cavity 60 and particularly the mixing channel 66 and the distribution groove 148 in communication therewith through the interconnecting groove 76. Accordingly, any second constituent entering the device 40 and making its way into the interior cavity 60, and particularly the distribution groove 148, can only then flow into the mixing channel 66 through the interconnecting groove 76 and not back out of the device 40 through any other path or into the mixing channel 66 anywhere but substantially at its input end, thus again forcing the reconstitution of the first constituent or the mixing of the first and second constituents within the mixing channel 66. Relatedly, if the distribution groove 148 is effectively sealed "above" by the o-ring 126, then the groove 148 is effectively sealed "below" through the engagement between the plug seating portion 154 and the container seating portion 84 (FIG. 19). In the exemplary embodiment, the effective engagement between these surfaces is a net-fit arrangement. Particularly, the two surfaces or seating portions 84, 154 are here shown as somewhat tapered annular walls configured to be brought into substantially abutting contact upon full assembly of the plug component 130 within the container component 50. It will be appreciated by those skilled in the art, with further reference to the numerous alternative embodiments presented herein, that a variety of other configurations and interoperability of the components of a solution delivery device according to aspects of the present invention are thus possible without departing from its spirit and scope. For example, once more, the engagement surfaces between the container and plug components may also be substantially straight-walled or curve-walled. It is further noted in connection with putting the device 40 into the second operational mode shown in FIG. 21, or shifting the device 40 from the first operational mode as shown in FIG. 20 to the second operational mode as shown in FIG. 21, that the flexible legs 102 of the container component 50, or more precisely here the engagement component 100, on which are formed the engagement lips 92 allow the lips 92 to deflect or shift radially outwardly to pass out of the engagement groove 162 and traverse the cut-outs 188 before springing back into place over or abutting the proximal end 132 of the plug component 130. Once more, the geometric or mechanical design along with the selection of an appropriate medical grade plastic with sufficient elasticity enables the requisite flexibility and functionality of the device 40.

Figure 22:
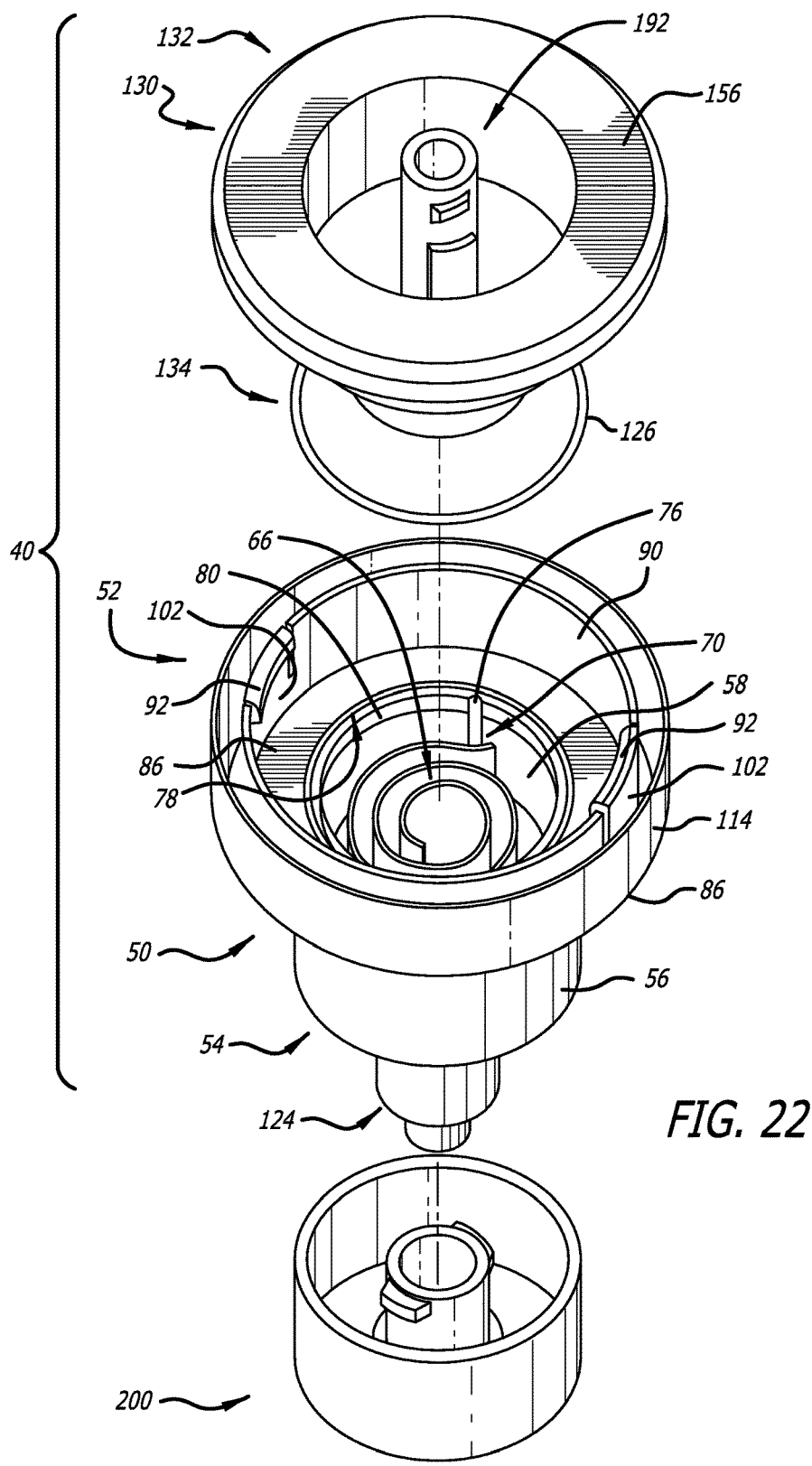
FIG. 22 illustrates an exploded perspective view of a further alternative exemplary drug delivery device according to aspects of the present invention.
Figure 23:
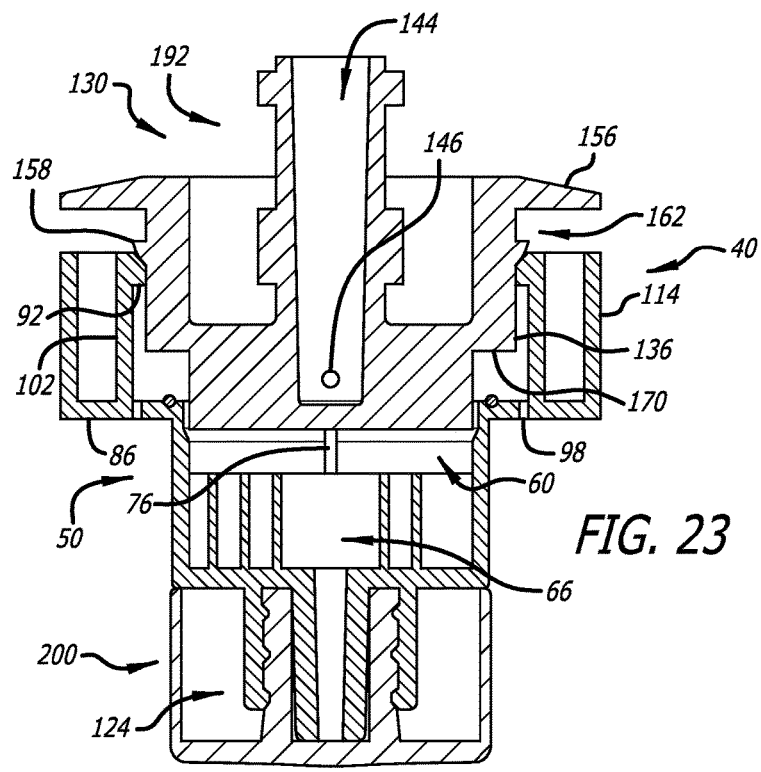
FIG. 23 illustrates an enlarged assembled side cross-sectional view thereof in a first mode of operation.
Figure 24:
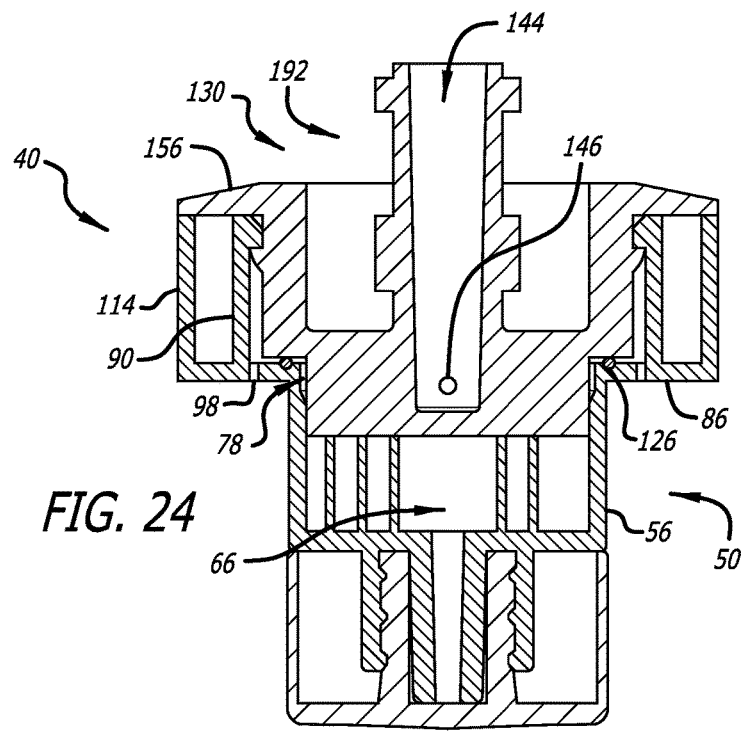
FIG. 24 illustrates an enlarged assembled side cross-sectional view thereof in a second mode of operation.

Turning next to FIGS. 22-24, there is shown a further alternative exemplary embodiment analogous to that of FIGS. 1-6, with the primary difference being that a perimeter wall 114 is formed on the container component 50 so as to extend proximally from a point radially outward of the engagement wall 90. The plug flange 156 is then also configured to extend radially outward of the engagement wall 90 when the components are assembled so as to be substantially coterminous with the perimeter wall 114, such that when the plug component 130 is fully inserted within the container component 50 the perimeter wall 114 in cooperation with the plug flange 156 serve to substantially completely enclose the engagement wall 90, and particularly the flexible legs 102 with engagement lips 92, thereby further securing the engagement of the two components or preventing tampering with or other improper or unintended separation of the components or opening of the device 40 once assembled as shown in FIG. 24 in the second operational mode. It will be appreciated by those skilled in the art that a number of other such configurations for securing or tamper-proofing the assembly of the plug component 130 within the container component 50 are possible without departing from the spirit and scope of the invention, such as a radial skirt (not shown) extending distally from the plug flange 156 so as to meet the container flange 86 or at least substantially cover or enclose the engagement wall 90. The container component 50 again generally comprises a lower base wall 56 and an upper engagement wall 90 forming its body. In the illustrated embodiment, the container component 50 further comprises an interconnecting groove 76 formed in the inner surface 58 of the base wall 56 so as to be in fluid communication with the input end 70 of the mixing channel 66. Preferably, the interconnecting groove 76 is substantially lengthwise along the container component base wall 56, though it will be appreciated that other orientations of the groove 76 may also be employed. The interconnecting groove 76 is of sufficient length to be in fluid communication with the plug outlet port 146 (FIGS. 23 and 24) upon assembly of the plug component 130 within the container component 50 in the second operational mode, as shown in FIG. 24, whereby the mixing channel 66 provides an indirect flow path between the plug outlet port 146 and the ejection connector port 124. The container component 50 further generally comprises a distribution groove 78 formed in the inner surface 58 of the base wall 56 so as to be in fluid communication with the interconnecting groove 76. In the exemplary embodiment, the distribution groove 78 is configured as an upwardly-opening step 80 in the inner surface 58 of the base wall 56, such that the base wall 56 has a stepped inner bore. The base wall 56 of the container component 50 is further shown as again terminating proximally in a substantially radially-outwardly extending container flange 86 that extends radially-outwardly beyond the proximally extending engagement wall 90. Once more, the perimeter wall 114 then extends substantially proximally from the container flange 86 radially outwardly of and spaced from the engagement wall 90. In the exemplary embodiment, the container flange 86 thus terminates radially in the proximally extending perimeter wall 114, with the engagement wall 90 being intermediate. As shown, the engagement and perimeter walls 90, 114 are substantially annular, concentric, and coterminous proximally, though those skilled in the art will appreciate that this need not be the case and that other geometric configurations are possible according to aspects of the present invention. The engagement wall 90 again itself terminates proximally in at least one radially-inwardly projecting engagement lip 92. In the exemplary embodiment, the radially-inwardly projecting engagement lip 92 is formed on two opposing flexible legs 102 defining a portion of the engagement wall 90 of the container component 50. Further regarding the plug component 130, again, the side wall 136 terminates proximally in a radially-outwardly extending plug flange 156 defining a plug perimeter that is substantially radially coterminous with the perimeter wall 114 of the container component 50 when the components are assembled. Otherwise, the plug component 130 is much the same as in the exemplary embodiment of FIGS. 1-6. Further details concerning the plug component 130 and its engagement with the container component 50 are appreciated from the below discussion regarding FIGS. 23 and 24 depicting in section the device 40 in its two illustrated operational modes.

Referring to FIG. 23, there is again shown the device 40 of FIG. 22 in its first operational mode, wherein the plug component 130 is partially inserted within the container component 50. Specifically, the radially-outwardly projecting retention lip 158 formed on the side wall 136 of the plug component 130 seats on the radially-inwardly projecting engagement lip 92 formed proximally on the flexible legs 102 of the engagement wall 90 (FIG. 22) of the container component 50. In this position, the plug component 130 is effectively suspended within the container component 50 with the shoulder 170 of the plug component 130 spaced above the container flange 86 of the container component 50, thereby providing clearance between the plug and container components so as to facilitate fluid communication between the internal cavity 60 of the container component 50, and particularly the elongated mixing channel 66, and the surrounding atmosphere through one or more container vent holes 98. It will be appreciated that with the legs 102 and corresponding lips 92 in contact with the retention lip 158 only comprising a portion of the engagement wall perimeter, there is actually clearance between the plug component 130 and the container component 50 for ventilation beyond the vent holes; but in cases where both the engagement lip 92 and the retention lip 158 are substantially continuous, it will be understood that the one or more container vent holes 98 will provide effectively the only means of venting the internal cavity 60 of the container component 50 during the first operational mode of the device 40. It will thus again be appreciated by those skilled in the art that in such a first operational mode or position of the device 40, the device may then be subjected to a lyophilization process whereby the interior of the container component 50 can vent or have a vacuum pulled on it or be subjected to any other process that requires fluid flow relative to the liquid to be processed. Then, as shown in FIG. 24, the plug component 130 is fully inserted within the container component 50 such that the container's engagement lip 92 engages the plug's engagement groove 162 (FIG. 23) and the plug seats on or is otherwise substantially adjacent to the mixing channel 66. Again, when the plug component 130 is thus seated within the container component 50 so as to configure the device 40 in the second operational mode, the plug shoulder 170 (FIG. 23) is brought adjacent to the container flange 86 so as to squeeze and seal against the o-ring 126 and thereby seal off the container vent holes 98 and form or completely bound the distribution groove 78, such that any second constituent entering the device 40 and making its way into the interior cavity 60, and particularly the distribution groove 78, of the container component 50 can only then flow into the mixing channel 66 and not back out of the device 40 through any other path, thus again forcing the reconstitution of the first constituent or the mixing of the first and second constituents within the mixing channel 66. Relatedly, if the distribution groove 78 is effectively sealed "above" by the o-ring 126, then it is effectively sealed "below" through the engagement between plug's outer surface and the container's inner surface as described herein. It will again be appreciated by those skilled in the art, with further reference to the numerous alternative embodiments presented herein, that a variety of other configurations and interoperability of the components of a solution delivery device according to aspects of the present invention are thus possible without departing from its spirit and scope. It is again further noted in connection with putting the device 40 into the second operational mode shown in FIG. 24, or shifting the device 40 from the first operational mode as shown in FIG. 23 to the second operational mode as shown in FIG. 24, that the flexible legs 102 of the container component 50 on which are formed the engagement lips 92 allow the lips 92 to deflect or shift radially outwardly to pass over the retention lip 158 of the plug component 130 and then spring or seat into the plug engagement groove 162 (FIG. 23). In the exemplary embodiment, each flexible leg 102 is attached to the engagement wall 90 along a lower edge so as to function as a living hinge, such that the geometric or mechanical design along with the selection of an appropriate medical grade plastic with sufficient elasticity enables the requisite flexibility and functionality. Moreover, as can be seen and will be appreciated, the engaging or opposed surfaces of the respective engagement lip 92 and retention lip 158 are sloped so as to effectively provide a ramp along which the engagement lip 92 travels as it shifts radially outwardly as the plug component 130 is advanced distally within or relative to the container component 50 until the engagement lip 92 clears the retention lip 158 proximally and seats within the engagement groove 162 to effectively lock the plug component 130 within the container component 50 in the configuration of the device 40 shown in FIG. 24. As will also be appreciated particularly from FIG. 24, in the exemplary embodiment the plug flange 156 defines a plug perimeter that is substantially radially coterminous now with the outer perimeter wall 114 of the container component 50 for a substantially flush fit between the plug and container components when the device 40 is in its second operational mode as shown. While a fairly significant space or separation between the outer perimeter wall 114 and the inner engagement wall 90 is shown, it will be appreciated that the radial gap or distance between the walls may be relatively smaller, in which case the plug flange 156 may be reduced in size proportionately as well. So long as the space between the engagement wall 90 and the perimeter wall 114 is sufficient to allow the legs 102 to flex radially outwardly as the engagement lips 92 pass over the retention lip 158, then the device will function properly. Or, the legs 102 and/or lips 92 may be formed of resilient materials that can deform under pressure, thereby allowing for an even smaller clearance between the perimeter wall 114 and the engagement wall 90. Again, those skilled in the art will appreciate that a variety of other configurations beyond those shown and described are possible according to aspects of the present invention, such that the illustrated embodiments are to be understood as exemplary and non-limiting.

Figure 25:
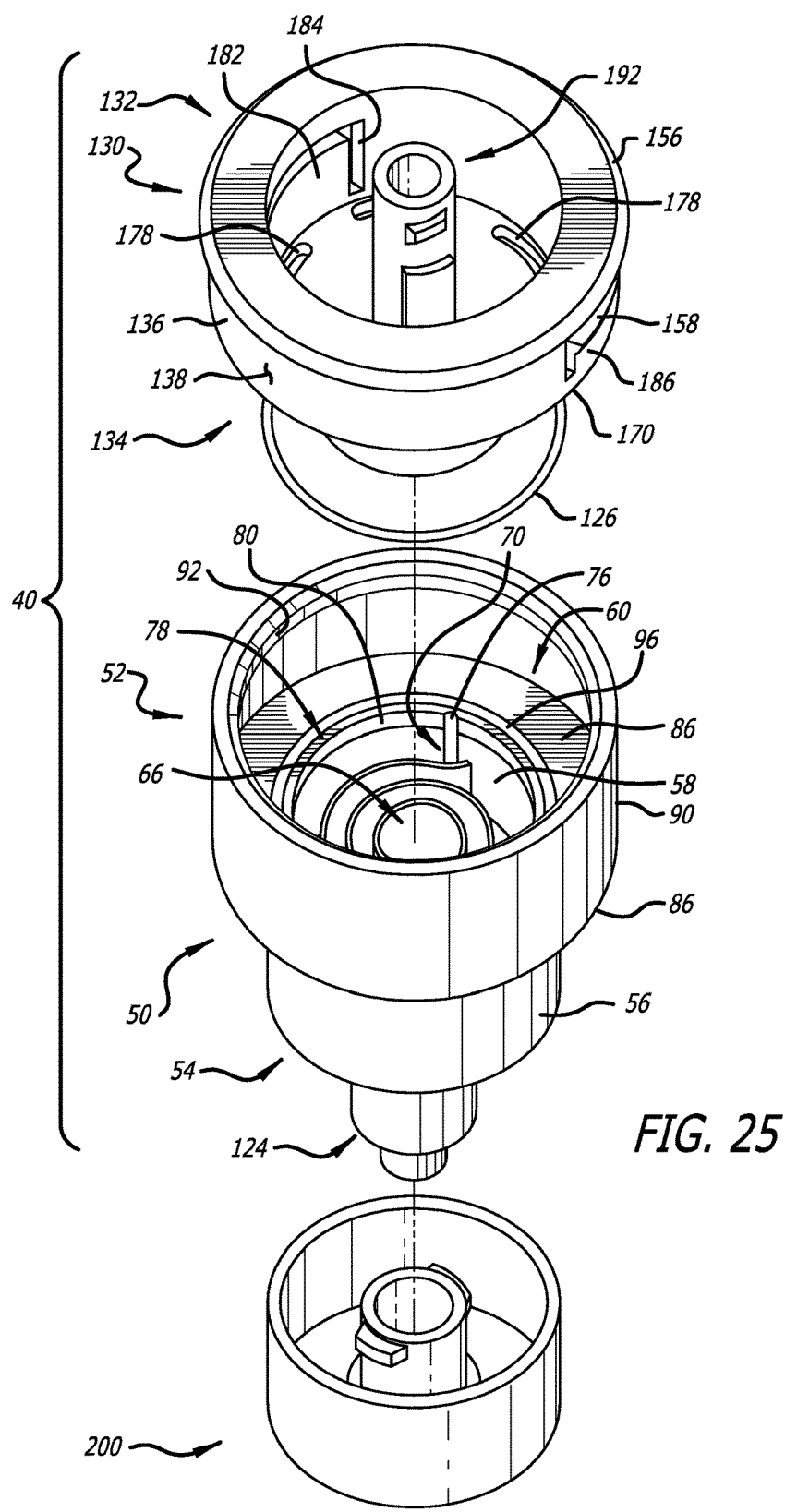
FIG. 25 illustrates an exploded perspective view of a further alternative exemplary drug delivery device according to aspects of the present invention.
Figure 26:
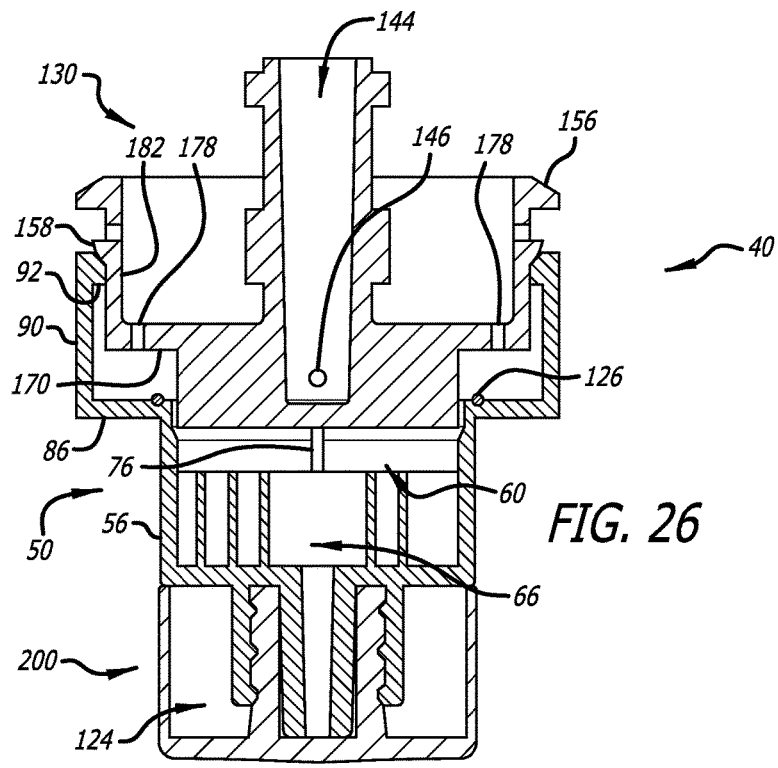
FIG. 26 illustrates an assembled side cross-sectional view thereof in a first mode of operation.
Figure 27:
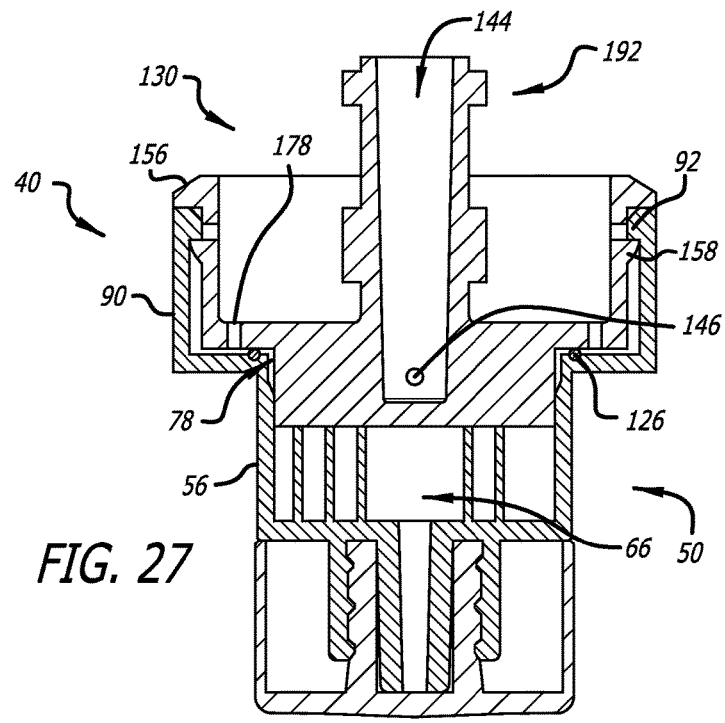
FIG. 27 illustrates an assembled side cross-sectional view thereof in a second mode of operation.

Referring now to FIGS. 25-27, there is shown a further alternative exemplary embodiment solution delivery device 40 according to aspects of the present invention. Essentially, here, the flexible legs 182 are formed on the plug component 130 rather than on the container component 50 as in other exemplary embodiments herein. As such, the legs 182 terminating proximally in the radially-outwardly extending retention lip 158 are formed in the side wall 136 of the plug component 130 as shown. Again, substantially lengthwise notches 184 define each leg 182 as a portion of the side wall 136. It will be appreciated that the proximal end of each leg 182 is also free of the side wall 136, such that the legs 182 are only connected to the side wall 136 along a lower or distal joint 186 that defines or functions as a living hinge, thereby enabling the legs 182 to flex in use. In the exemplary embodiment, the side wall 136 comprises two substantially offset flexible legs 182, though it will be appreciated that instead there may just as easily be three, four, or more such legs 182, or even only one. To retain the plug component 130 within the container component 50 during use, particularly in the second operational mode as shown in FIG. 27, a radially-inwardly projecting container engagement lip 92 is formed proximally on the container engagement wall 90 and configured to allow the plug retention lip 158 formed on the flexible legs 182 to seat thereunder when the plug component 130 is fully inserted. As shown, the engagement lip 92 is in this exemplary embodiment substantially continuous while the retention lip 158 is circumferentially associated only with each flexible leg 182 or is thereby discontinuous or discretely formed per leg 182. As elsewhere herein in connection with other exemplary embodiments, it will be appreciated that by here forming the engagement lip 92 of the container component 50 to be substantially continuous, no matter the orientation of the plug component 130 relative to the container component 50 the two components may be engaged and any fluid introduced into the plug component 130 through its inlet connector port 192 and the associated internal flow path 144 will be able to make its way into the mixing channel 66 of the container component 50 due to the plug outlet port 146 being in fluid communication with the interconnecting groove 76, and hence the mixing channel 66, through the substantially continuous distribution groove 78 formed as the step 80 in the inner surface 58 of the base wall 56 of the container component 50. The plug flange 156 is then also configured to extend radially outward of the side wall 136 so that when the components are assembled the plug flange 156 effectively caps and is flushed with the container wall 90, more about which is said below. It will be appreciated by those skilled in the art that a number of other such configurations for securing or tamper-proofing the assembly of the plug component 130 within the container component 50 are possible without departing from the spirit and scope of the invention. As can also be seen in FIG. 25, the plug component 130, rather than the container component 50 or neither component, is formed with at least one plug vent hole 178 within the distal end 134 of the plug component 130 radially outwardly of the base wall 56 of the container component 50, whereby in the first operational mode with the plug component 130 partially inserted within the container component 50 as shown in FIG. 26, there is fluid communication between the inner cavity 60 of the container component 50 and the surrounding atmosphere at least through the at least one plug vent hole 178. In an embodiment such as shown wherein a proximally-facing o-ring groove 96 is formed on the container flange 86, the at least one plug vent hole 178 is formed within the distal end 134 of the plug component 130 radially outwardly of the container o-ring groove 96, whereby in the first operational mode with the plug component 130 partially inserted within the container component 50 as shown in FIG. 26 there is again fluid communication between the internal cavity 60 of the container component 50 and the surrounding atmosphere at least through the at least one plug vent hole 178, and further whereby in the second operational mode with the plug component 130 fully assembled within the container component 50 as shown in FIG. 27, the o-ring 126 seated in the o-ring groove 96 seals between the shoulder 170 of the plug component 130 and the container flange 86 of the container component 50 so as to prevent fluid communication between the internal cavity 60 and the surrounding atmosphere. It will be appreciated that virtually any number of such plug vent holes 178 may be formed spaced about the plug's distal end 134. The container component 50 again generally comprises a lower base wall 56 and an upper engagement wall 90 forming its body. In the illustrated embodiment, the container component 50 once again further comprises an interconnecting groove 76 formed in the inner surface 58 of the base wall 56 so as to be in fluid communication with the input end 70 of the mixing channel 66. The interconnecting groove 76 is of sufficient length to be in fluid communication with the plug outlet port 146 (FIGS. 26 and 27) upon assembly of the plug component 130 within the container component 50 in the second operational mode, as shown in FIG. 27, whereby the mixing channel 66 provides an indirect flow path between the plug outlet port 146 and the ejection connector port 124. The container component 50 further generally comprises a distribution groove 78 formed as an upwardly-opening step 80 in the inner surface 58 of the base wall 56, such that the base wall 56 has a stepped inner bore, and being in fluid communication with the interconnecting groove 76. The base wall 56 of the container component 50 is further shown as again terminating proximally in a substantially radially-outwardly extending container flange 86 that terminates radially-outwardly in the proximally-extending engagement wall 90, which itself terminates proximally in the radially-inwardly projecting engagement lip 92. In the exemplary embodiment, the radially-inwardly projecting engagement lip 92 is again substantially continuous for indiscriminate engagement with the plug retention lip 158 as described further below.

Referring to FIG. 26, there is again shown the device 40 of FIG. 25 in its first operational mode, wherein the plug component 130 is partially inserted within the container component 50. Specifically, the radially-outwardly projecting retention lip 158 formed on the flexible legs 182 of the side wall 136 of the plug component 130 seats on the radially-inwardly projecting engagement lip 92 formed proximally on the engagement wall 90 of the container component 50. In this position, the plug component 130 is effectively suspended within the container component 50 with the shoulder 170 of the plug component 130 spaced above the container flange 86 of the container component 50, thereby providing clearance between the plug and container components so as to facilitate fluid communication between the internal cavity 60 of the container component 50, and particularly the elongated mixing channel 66, and the surrounding atmosphere through one or more plug vent holes 178. It will be appreciated that with the legs 182 and corresponding lips 158 in contact with the engagement lip 92 only comprising a portion of the engagement wall perimeter, there is actually clearance between the plug component 130 and the container component 50 for ventilation beyond the vent holes; but in cases where both the engagement lip 92 and the retention lip 158 are substantially continuous, it will be understood that the one or more plug vent holes 178 will provide effectively the only means of venting the internal cavity 60 of the container component 50 during the first operational mode of the device 40, as when, for example, a first constituent such as a liquid medication is filled in the cavity 60, and particularly the mixing channel 66, and is then to be subjected to a lyophilization procedure. In any event, it will thus again be appreciated by those skilled in the art that in such a first operational mode or position of the device 40 as shown in FIG. 26, the device may then be subjected to a lyophilization process whereby the interior of the container component 50 can vent or have a vacuum pulled on it or be subjected to any other process that requires fluid flow relative to the liquid to be processed. Then, as shown in FIG. 27, the plug component 130 is fully inserted within the container component 50 such that the plug's retention lips 158 engage the container's engagement lip 92 and the plug seats on or is otherwise substantially adjacent to the mixing channel 66. Again, when the plug component 130 is thus seated within the container component 50 so as to configure the device 40 in the second operational mode, the plug shoulder 170 (FIG. 26) is brought adjacent to the container flange 86 so as to squeeze and seal against the o-ring 126 and thereby seal off the plug vent holes 178 and form or completely bound the distribution groove 78, such that any second constituent entering the device 40 and making its way into the interior cavity 60, and particularly the distribution groove 78, of the container component 50 can only then flow into the mixing channel 66 and not back out of the device 40 through any other path, thus again forcing the reconstitution of the first constituent or the mixing of the first and second constituents within the mixing channel 66. Relatedly, if the distribution groove 78 is effectively sealed "above" by the o-ring 126, then it is once again effectively sealed "below" through the engagement between plug's outer surface and the container's inner surface as described herein. It will again be appreciated by those skilled in the art, with further reference to the numerous alternative embodiments presented herein, that a variety of other configurations and interoperability of the components of a solution delivery device according to aspects of the present invention are thus possible without departing from its spirit and scope. It is further noted once more in connection with putting the device 40 into the second operational mode shown in FIG. 27, or shifting the device 40 from the first operational mode as shown in FIG. 26 to the second operational mode as shown in FIG. 27, that the flexible legs 182 of the plug component 130 on which are formed the retention lips 158 allow the lips 158 to deflect or shift radially inwardly to pass within the engagement lip 92 of the container component 50 and then spring back out to seat beneath the engagement lip 92 to effectively lock the device 40 in the second operation mode as shown in FIG. 27. In the exemplary embodiment, each flexible leg 182 is again attached to or incorporated into the side wall 136 of the plug component 130 along a lower edge or joint 186 (FIG. 25) so as to function as a living hinge, such that the geometric or mechanical design along with the selection of an appropriate medical grade plastic with sufficient elasticity enables the requisite flexibility and functionality. Moreover, as can be seen and will be appreciated, the engaging or opposed surfaces of the respective engagement lip 92 and retention lip 158 are sloped so as to effectively provide a ramp along which the retention lip 158 travels as it shifts radially inwardly as the plug component 130 is advanced distally within or relative to the container component 50 until the retention lip 158 clears the engagement lip 92 distally and seats thereunder. As will also be appreciated particularly from FIG. 27, in the exemplary embodiment the plug flange 156 defines a plug perimeter that is substantially radially coterminous with the container engagement wall 90 for a substantially flush fit between the plug and container components when the device 40 is in its second operational mode as shown. Again, those skilled in the art will appreciate that a variety of other configurations beyond those shown and described are possible according to aspects of the present invention, such that the illustrated embodiments are to be understood as exemplary and non-limiting.

Figure 28:
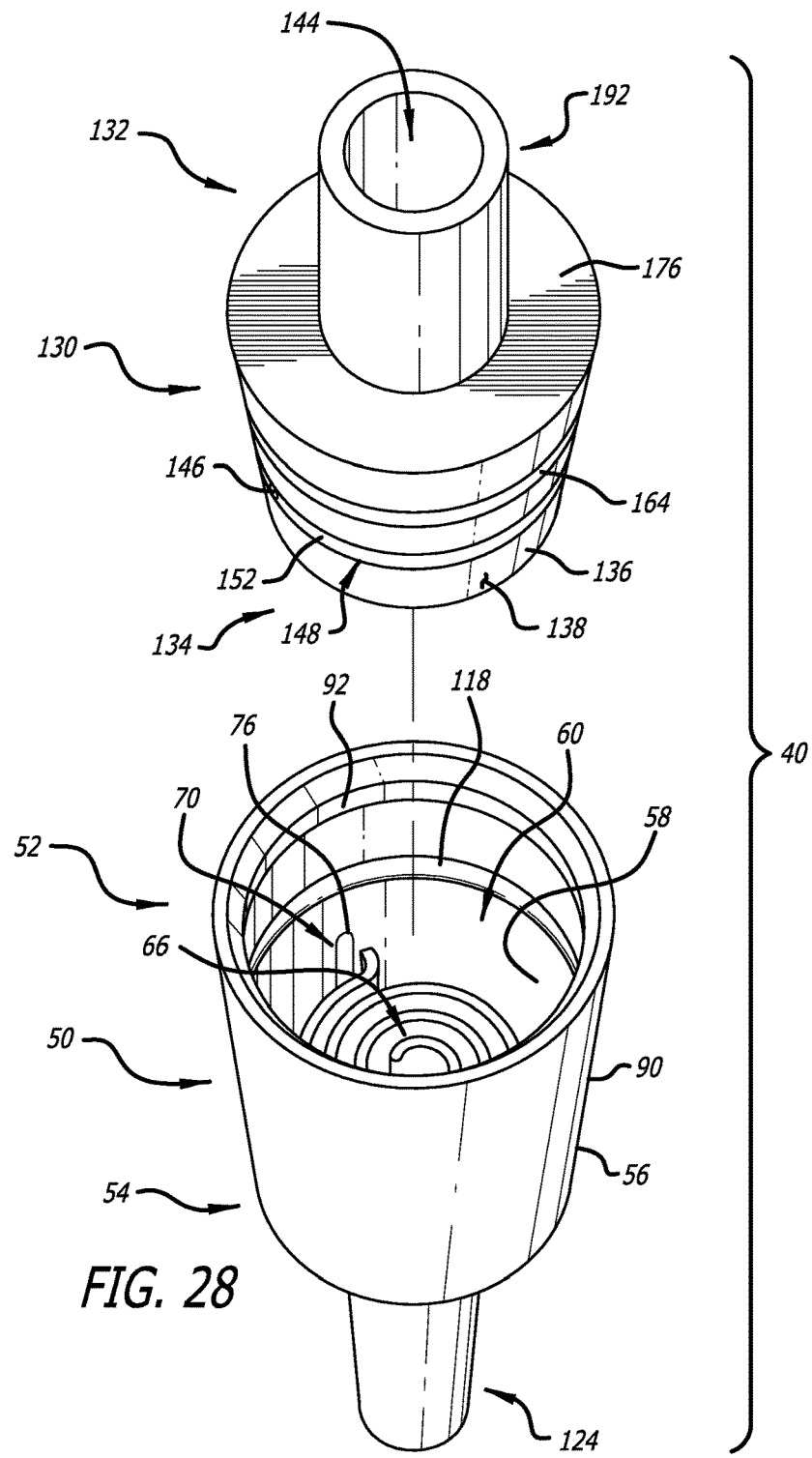
FIG. 28 illustrates an exploded perspective view of a further alternative exemplary drug delivery device according to aspects of the present invention.
Figure 29:
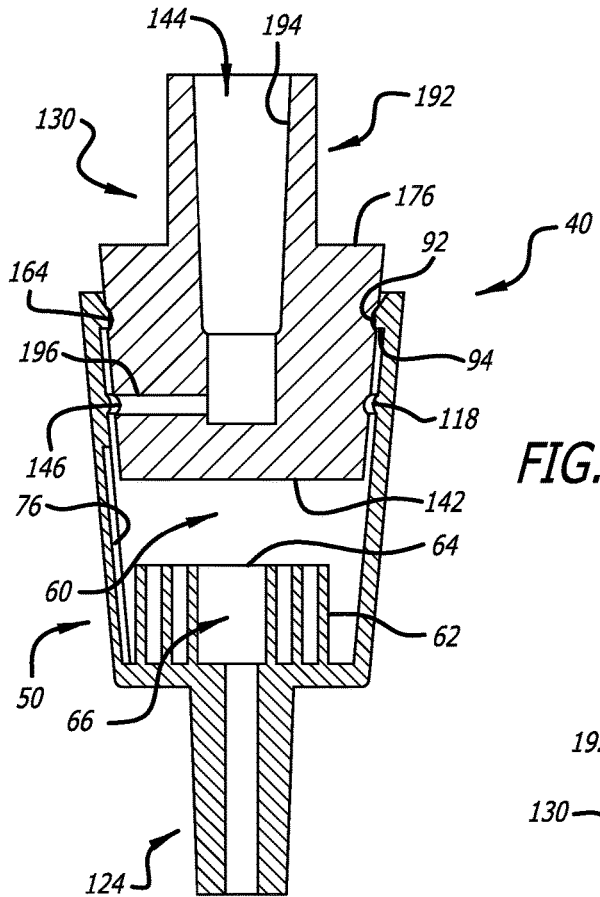
FIG. 29 illustrates a reduced scale assembled side cross-sectional view thereof in a first mode of operation.
Figure 30:
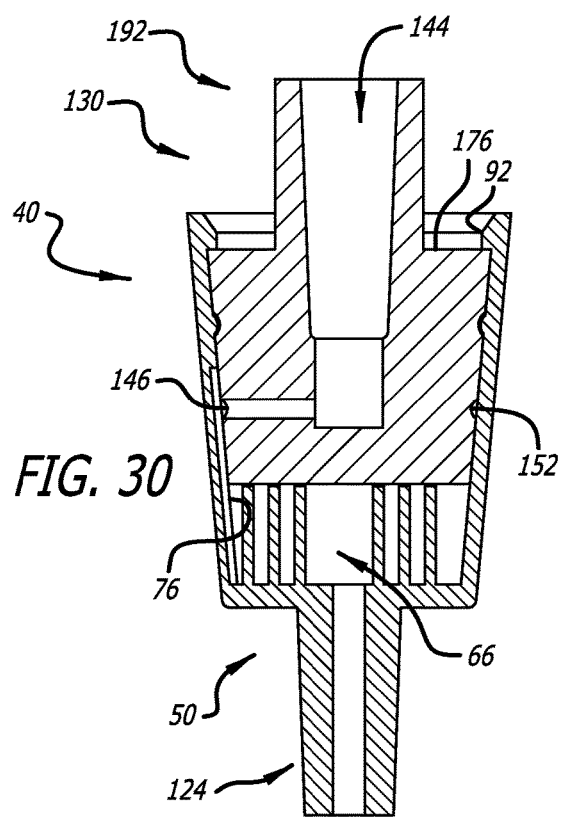
FIG. 30 illustrates a reduced scale assembled side cross-sectional view thereof in a second mode of operation.

Turning now to FIGS. 28-30, there is shown a further alternative exemplary embodiment of a solution delivery device 40 according to aspects of the present invention. As a threshold matter, it is noted that for convenience and clarity neither the container outlet cap 200 (FIGS. 1, 7, 13, 22 and 25) nor the plug inlet cap 220 (FIGS. 6 and 12) are shown, though it will be appreciated that both will be employed generally as described herein. With reference to the exploded perspective view of FIG. 28, it can be seen that the container component 50, as in the embodiments of FIGS. 13-21, does not have a shoulder but is instead substantially straight-walled. Here, in fact, the lower base wall 56 and the upper engagement wall 90 of the container component 50 are substantially contiguous or unitary. In the exemplary embodiment, the resulting container body is shown as being substantially uniform with a slight outward taper from the lower or distal end 54 to the open upper or proximal end 52. Once more, the container component 50 has an inner surface 58 defining an internal cavity 60 with a size selected to contain a predetermined quantity of a first constituent. Within the cavity 60 there is again formed the elongated mixing channel 66. An interconnecting groove 76 is also formed in the inner surface 58 of the base wall 56 so as to be in fluid communication between the distribution groove 148 formed as a radially-outwardly opening recess 152 in the plug component 130 and the mixing channel 66 of the container component 50 upon assembly of the plug component 130 within the container component 50 in the second operational mode, as shown in FIG. 30, whereby the mixing channel 66 provides an indirect flow path between the plug outlet port 146 and the ejection connector port 124. Here, the container component 50 does not include a separate distribution groove formed in the inner surface 58 of the base wall 56 as in other alternative embodiments, such that only the plug distribution groove 148 provides the function of fluidly connecting the plug outlet port 146 and the interconnecting groove 76. Regarding the plug component 130, the outer surface 138 of the side wall 136 is again formed having a radially-outwardly opening recess 152 defining the distribution groove 148, with the plug outlet port 146 located in the side wall 136 so as to intersect and be in fluid communication with the distribution groove 148 or plug recess 152. As in other embodiments, an outwardly-opening retention groove 164 is formed in the outer surface 138 of the side wall 136 of the plug component 130 proximal of the plug outlet port 146 and recess 152 so as to be selectively engaged by the engagement lip 92 of the container component 50 during operation of the device 40, particularly in the first operational mode shown in FIG. 29, more about which is said below. Like the mating container component 50, in the alternative embodiment, the plug component 130 is also substantially straight-walled, with a slight outward taper from the lower or distal end 134 to the upper or proximal end 132. A radially-inwardly projecting retention lip 118 is formed on the inner surface 58 of the container component 50 configured, or sized and positioned, for selective engagement with the plug retention groove 164 particularly when the plug component 130 is fully seated within the container component 50 as in the second operational mode of the device 40 as shown in FIG. 30.

Referring then to FIGS. 29 and 30 depicting the exemplary solution delivery device 40 of FIG. 28 in its first and second operational modes, in use again in the exemplary context of a liquid medication to be subjected to a lyophilization procedure, the device 40 may be placed in any suitable automated, semi-automated, or manual filling machine for the purpose of filling the cavity 60 or particularly the mixing channel 66 with the desired predetermined quantity of liquid first constituent. Before or after that step, though most often after, the plug component 130 is again then inserted partway into the container component 50 as shown here in FIG. 29 so as to put the device 40 in the first operational mode as when it is to be placed in a lyophilizer or otherwise be processed. Particularly, it is noted that the radially-inwardly projecting engagement lip 92 formed at the proximal open end 52 of the container component 50 temporarily engages or seats within the plug retention groove 164 on the outer surface 138 of the side wall 136 (FIG. 28) of the plug component 130 as by the rim of the container component or the lip 92 itself or both flexing radially outwardly as the plug component 130 is advanced distally within the container component 50 and thus the engagement lip 92 is shifted proximally relative to the plug component 130 until the lip 92 seats within the retention groove 164 as shown in FIG. 29. In this position, the plug component 130 is essentially suspended within the container component 50 such that the plug distal surface 142 is spaced from the mixing channel wall top surface 64, thereby providing clearance between the plug and container components so as to facilitate fluid communication between the internal cavity 60 of the container component 50, and particularly the elongated mixing channel 66, and the surrounding atmosphere, here particularly through the plug's internal flow path 144, which is again formed as shown by a substantially axial or lengthwise bore 194 intersected by a substantially transverse cross-bore 196 that defines the plug outlet port 146 where the cross-bore 196 intersects the plug surface 138 (FIG. 28). Accordingly, in this alternative embodiment it may be preferable to not install the plug inlet cap 220 (FIG. 6) until after any processing of the device 40 in its first operational mode is completed. It will be appreciated by those skilled in the art that in such a first operational mode or position of the device 40, the device may then be subjected to a lyophilization process as needed whereby the interior of the container component 50 can vent or have a vacuum pulled on it or be subjected to any other process that requires fluid flow relative to the first constituent liquid to be processed. Then, as shown in FIG. 30, when the illustrative lyophlization procedure or other such procedure is complete, the plug component 130 may be fully inserted within the container component 50, which may again be accomplished by an automated, semi-automated, or manual process. In the alternative exemplary embodiment, pushing the plug component 130 all the way into the container component 50 such that, here, the container's engagement lip 92 engages the proximal end 132 of the plug component 130 (FIG. 28), the plug distal surface 142 is thus brought into engagement or substantially abutting contact with or otherwise substantially adjacent to the top surface 64 of the wall 62 of the mixing channel 66 (FIG. 29), thereby effectively closing off the mixing channel 66 except for its input end in the vicinity of the interconnecting groove 76. Particularly, as shown, the proximal end 132 of the plug component 130 is formed having a proximally-facing plug proximal surface 176, and the engagement lip 92 is formed having a substantially distally-facing lip distal surface 94 (FIG. 29) configured to seat against the plug proximal surface 176 when the plug component 130 is fully seated within the container component 50 in the second operational mode of the device 40. Once again, more about the device 40 so configured in its second operational mode post-lyophilization in various exemplary contexts and clinical uses and hence various constituents within the device 40 are all discussed further below, particularly in connection with FIGS. 40-42, but here it is sufficient to note that flowing a second constituent into the device 40 as through the inlet connector port 192 and associated flow path 144 of the plug component 130 allows such second constituent to exit the plug outlet port 146, fill or flow into the plug distribution groove 148, and then find its way into the mixing channel 66 through the longitudinal interconnecting groove 76 so as to then reconstitute the previously lyophilized first constituent housed within the mixing channel 66, once again without any separate mixing, shaking, priming, or other reconstitution step. It will be appreciated that in the second operational mode with the plug component 130 fully inserted within the container component 50, the respective tapered surfaces of the container inner surface 58 and the plug outer surface 138 serve to engage and form an effective net-fit seal between the mating components, thereby again sealing off the internal cavity 60 and particularly the mixing channel 66 and the distribution groove 148 in communication therewith through the interconnecting groove 76. The engagement of the container retention lip 118 within the plug retention groove 164 further secures the components in place and cooperates to further seal off their surface-to-surface interface. Accordingly, any second constituent entering the device 40 and making its way into the interior cavity 60, and particularly the distribution groove 148, can only then flow into the mixing channel 66 through the interconnecting groove 76 and not back out of the device 40 through any other path or into the mixing channel 66 anywhere but substantially at its input end, thus again forcing the reconstitution of the first constituent or the mixing of the first and second constituents within the mixing channel 66 along its length. It will be appreciated by those skilled in the art, with further reference to the numerous alternative embodiments presented herein, that a variety of other configurations and interoperability of the components of a solution delivery device according to aspects of the present invention are thus possible without departing from its spirit and scope. For example, once more, the engagement surfaces between the container and plug components may also be substantially straight-walled or curve-walled. Once more, the geometric or mechanical design along with the selection of appropriate medical grade materials with sufficient elasticity enables the requisite functionality of the device 40.

Figure 31:
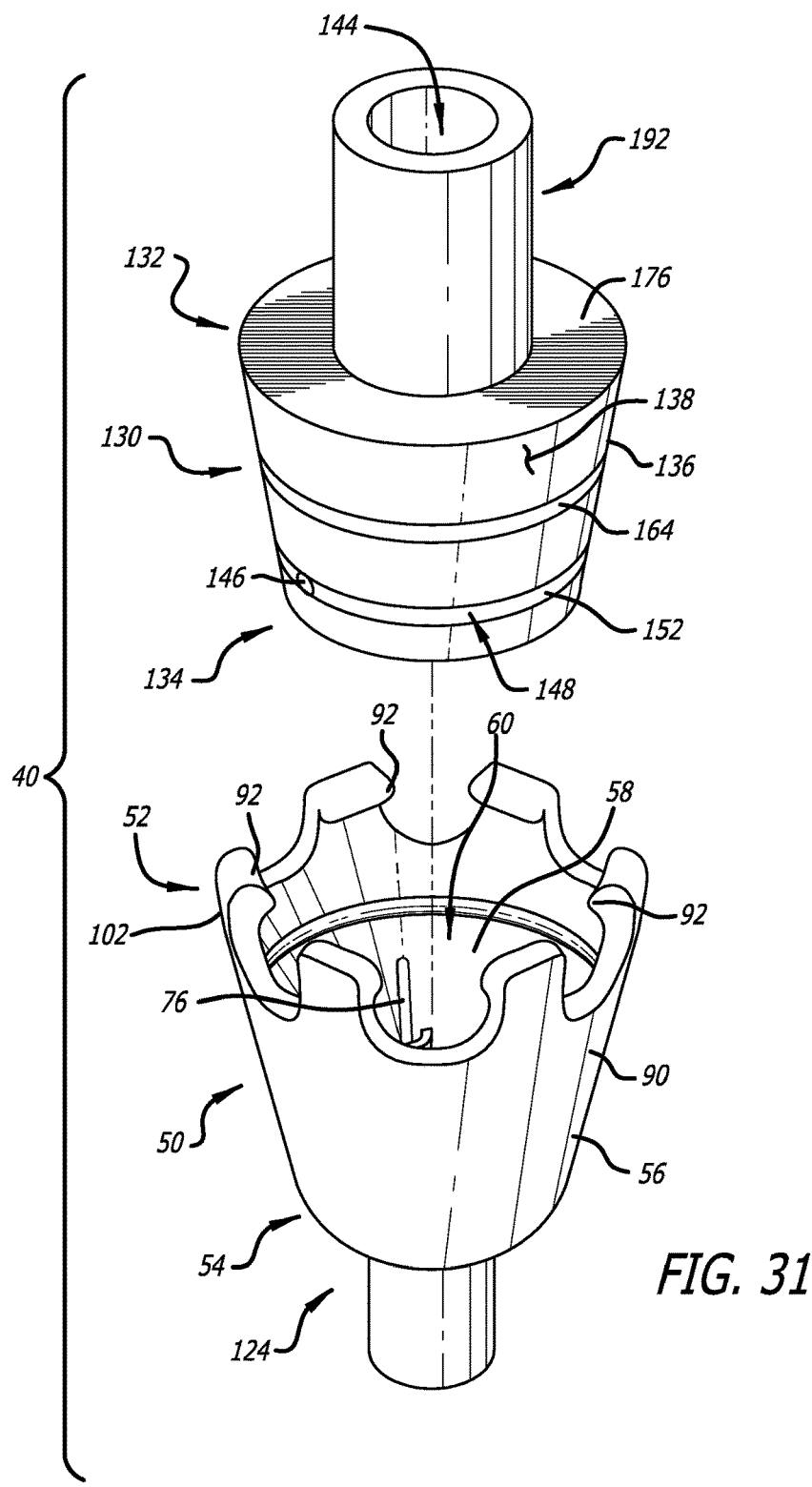
FIG. 31 illustrates an exploded perspective view of a further alternative exemplary drug delivery device according to aspects of the present invention.

Turning to FIGS. 31-33, there is shown a still further alternative exemplary embodiment of a solution delivery device 40 according to aspects of the present invention, here somewhat analogous to the embodiment of FIGS. 28-30. It is noted that for convenience and clarity neither the container outlet cap 200 (FIGS. 1, 7, 13, 22 and 25) nor the plug inlet cap 220 (FIGS. 6 and 12) are shown. Here, referring to the exploded perspective view of FIG. 31, it can again be seen that the container component 50 does not have a shoulder but is instead substantially straight-walled, with the lower base wall 56 and the upper engagement wall 90 of the container component 50 being substantially contiguous or unitary. In the exemplary embodiment, the resulting container body is shown as having a slight outward taper from the lower or distal end 54 to the open upper or proximal end 52, here with the proximal engagement wall 90 being undulated so as to form substantially proximally-extending legs 102 terminating proximally in the respective radially-inwardly extending engagement lips 92. Once more, the container component 50 has an inner surface 58 defining an internal cavity 60 with a size selected to contain a predetermined quantity of a first constituent. Within the cavity 60 there is again formed the elongated mixing channel 66 (FIGS. 32 and 33). A substantially lengthwise interconnecting groove 76 is again formed in the inner surface 58 of the base wall 56 so as to be in fluid communication between the distribution groove 148 formed as a radially-outwardly opening recess 152 in the plug component 130 and the mixing channel 66 (FIGS. 32 and 33) of the container component 50 upon assembly of the plug component 130 within the container component 50 in the second operational mode, as shown in FIG. 33, whereby the mixing channel 66 provides an indirect flow path between the plug outlet port 146 and the ejection connector port 124. Here, the container component 50 again does not include a separate distribution groove formed in the inner surface 58 of the base wall 56 as in other alternative embodiments, such that only the plug distribution groove 148 provides the function of fluidly connecting the plug outlet port 146 and the interconnecting groove 76. Regarding the plug component 130, the outer surface 138 of the side wall 136 is again formed having a radially-outwardly opening recess 152 defining the distribution groove 148, with the plug outlet port 146 located in the side wall 136 so as to intersect and be in fluid communication with the distribution groove 148 or plug recess 152. As in other embodiments, including that of FIGS. 28-30, an outwardly-opening retention groove 164 is formed in the outer surface 138 of the side wall 136 of the plug component 130 proximal of the plug outlet port 146 and recess 152 so as to be selectively engaged by the engagement lips 92 of the container component 50 during operation of the device 40, particularly in the first operational mode shown in FIG. 32, more about which is said below. Like the mating container component 50, in the alternative embodiment, the plug component 130 is also substantially straight-walled, with a slight outward taper from the lower or distal end 134 to the upper or proximal end 132. A radially-inwardly projecting retention lip 118 is again formed on the inner surface 58 of the container component 50 proximal of the mixing channel 66 and interconnecting groove 76 configured, or sized and positioned, for selective engagement with the plug retention groove 164 particularly when the plug component 130 is fully seated within the container component 50 as in the second operational mode of the device 40 as shown in FIG. 33.

Referring then to FIGS. 32 and 33 depicting the exemplary solution delivery device 40 of FIG. 31 in its first and second operational modes, in use again in the exemplary context of a liquid medication to be subjected to a lyophilization procedure, the device 40 may be placed in any suitable automated, semi-automated, or manual filling machine for the purpose of filling the cavity 60 or particularly the mixing channel 66 with the desired predetermined quantity of first constituent. Before or after that step, though most often after, the plug component 130 is again then inserted partway into the container component 50 as shown here in FIG. 32 so as to put the device 40 in the first operational mode as when it is to be placed in a lyophilizer or otherwise be processed. Particularly, it is noted that the radially-inwardly projecting engagement lips 92 formed at the proximal open end 52 of the container component 50, and particularly at the proximal ends of the upwardly-extending legs 102 (FIG. 31) temporarily engages or seats within the plug retention groove 164 on the outer surface 138 of the side wall 136 (FIG. 31) of the plug component 130 as by the legs 102 or the lips 92 or both flexing radially outwardly as the plug component 130 is advanced distally within the container component 50 and thus the engagement lip 92 is shifted proximally relative to the plug component 130 until the lips 92 seat within the retention groove 164 as shown in FIG. 32. In this position, the plug component 130 is essentially suspended within the container component 50 such that the plug distal surface 142 is spaced from the mixing channel wall top surface 64, thereby providing clearance between the plug and container components so as to facilitate fluid communication between the internal cavity 60 of the container component 50, and particularly the elongated mixing channel 66, and the surrounding atmosphere, here particularly through the plug's internal flow path 144. However, it will be appreciated that clearance and venting is provided between the components due to the undulated proximal end 52 of the container component 50, as between the legs 102. Accordingly, in this alternative embodiment, though it may be preferable to not install the plug inlet cap 220 (FIG. 6) until after any processing of the device 40 in its first operational mode is completed, that is not required due to the venting around the legs 102, or essentially in view of the engagement lip 92 being discontinuous rather than continuous. It will be appreciated by those skilled in the art that in such a first operational mode or position of the device 40, the device may then be subjected to a lyophilization process as needed whereby the interior of the container component 50 can vent or have a vacuum pulled on it or be subjected to any other process that requires fluid flow relative to the first constituent liquid to be processed. Then, as shown in FIG. 33, when the illustrative lyophlization procedure or other such procedure is complete, the plug component 130 may be fully inserted within the container component 50, which may again be accomplished by an automated, semi-automated, or manual process. In the alternative exemplary embodiment, pushing the plug component 130 all the way into the container component 50 such that, here, the container's engagement lips 92 engage the proximal end 132 of the plug component 130 (FIG. 31), the plug distal surface 142 is thus brought into engagement or substantially abutting contact with or otherwise substantially adjacent to the top surface 64 of the wall 62 of the mixing channel 66 (FIG. 32), thereby again effectively closing off the mixing channel 66 except for its input end in the vicinity of the interconnecting groove 76. Once again, flowing a second constituent into the device 40 as through the inlet connector port 192 and associated flow path 144 of the plug component 130 allows such second constituent to exit the plug outlet port 146, fill or flow into the plug distribution groove 148, and then find its way into the mixing channel 66 through the longitudinal interconnecting groove 76 so as to then reconstitute the previously lyophilized first constituent housed within the mixing channel 66 without any separate mixing, shaking, priming, or other reconstitution step. It will also be appreciated once more that in the second operational mode with the plug component 130 fully inserted within the container component 50, the respective tapered surfaces of the container inner surface 58 and the plug outer surface 138 serve to engage and form an effective net-fit seal between the mating components, thereby again sealing off the internal cavity 60 and particularly the mixing channel 66 and the distribution groove 148 in communication therewith through the interconnecting groove 76. The engagement of the container retention lip 118 within the plug retention groove 164, as in the embodiment of FIGS. 28-30, further secures the components in place and cooperates to further seal off their surface-to-surface interface. Accordingly, any second constituent entering the device 40 and making its way into the interior cavity 60, and particularly the distribution groove 148, can only then flow into the mixing channel 66 through the interconnecting groove 76 and not back out of the device 40 through any other path or into the mixing channel 66 anywhere but substantially at its input end, thus again forcing the reconstitution of the first constituent or the mixing of the first and second constituents within the mixing channel 66 along its length. It will again be appreciated by those skilled in the art, with further reference to the numerous alternative embodiments presented herein, that a variety of other configurations and interoperability of the components of a solution delivery device according to aspects of the present invention are thus possible without departing from its spirit and scope. Once more, the geometric or mechanical design along with the selection of appropriate medical grade materials with sufficient elasticity enables the requisite functionality of the device 40.

Referring next to FIGS. 34-39, there is shown yet another alternative exemplary embodiment of a solution delivery device 40 according to aspects of the present invention. As a threshold matter, once again, it is noted that for convenience and clarity neither the container outlet cap 200 (FIGS. 1, 7, 13, 22 and 25) nor the plug inlet cap 220 (FIGS. 6 and 12) are shown, though it will be appreciated that both will be employed generally as described herein. With reference first to the exploded perspective view of FIG. 34, it can be seen that the container component 50 again does not have a shoulder but is instead substantially straight-walled, with the lower base wall 56 and the upper engagement wall 90 of the container component 50 being substantially contiguous or unitary and having a slight outward taper from the bottom or distal end 54 to the open top or proximal end 52. Similarly, the plug component 130 is also again formed substantially straight-walled, with a slight outward taper from the lower or distal end 134 to the upper or proximal end 132 substantially corresponding to the mating container component 50. The container component 50 is also again formed with a radially-inwardly projecting engagement lip 92 at its proximal open end 52 configured particularly to engage or snap over the proximally-facing plug proximal surface 176 when the plug component 130 is fully seated within the container component 50 in the second operational mode of the device 40 as here shown in FIG. 39. But here, with particular reference now to the enlarged perspective views of the container component 50 and the plug component 130 of FIGS. 35 and 36, respectively, it can be seen that the container component is formed substantially along or adjacent to its inner surface 58 having a substantially proximally-facing ramped or sloped container indexing surface 120. A corresponding substantially distally-facing ramped or sloped plug indexing surface 190 is formed on or adjacent to the plug outer surface 138. It will be appreciated by those skilled in the art that the respective indexing surfaces 120, 190 serve to index or key the engagement of, and particularly the rotational or angular positions of, the respective components. As such, when the plug component 130 is fully inserted within the container component 50 as shown in FIG. 39, the engagement of the respective indexing surfaces 120, 190 act to orient the plug component 130 relative to the container component 50 in a desired or pre-selected position, thereby particularly positioning the plug outlet port 146 substantially adjacent to the input end 70 (FIG. 35) of the mixing channel 66 without the need for a distribution groove or interconnecting groove as in other embodiments. However, it will be further appreciated that depending on the height of the plug outlet port 146, such as it being located proximal of the plug distal end 134 rather than at the intersection of the plug outer surface 138 and the plug distal surface 142 as shown, an interconnecting groove may still be provided in either the inner surface 58 of the container component 50 or the outer surface 138 of the plug component 130 or both so as to conduct the second constituent introduced into the device 40 at the inlet connector port 192 through the internal flow path 144 from the plug outlet port 146 ultimately into the mixing channel 66, starting substantially at its input end 70. It will be appreciated more generally that a variety of other indexing surfaces or means, in construction and operation, may be employed according to aspects of the present invention without departing from its spirit and scope, such that the exemplary indexing surfaces 120, 190 are to be understood as illustrative and expressly non-limiting. By way of further non-limiting example, the indexing surfaces may be substantially helical, opposed inclined surfaces, threaded, or any other such mechanical coupling devices now known or later developed.

Figure 34:
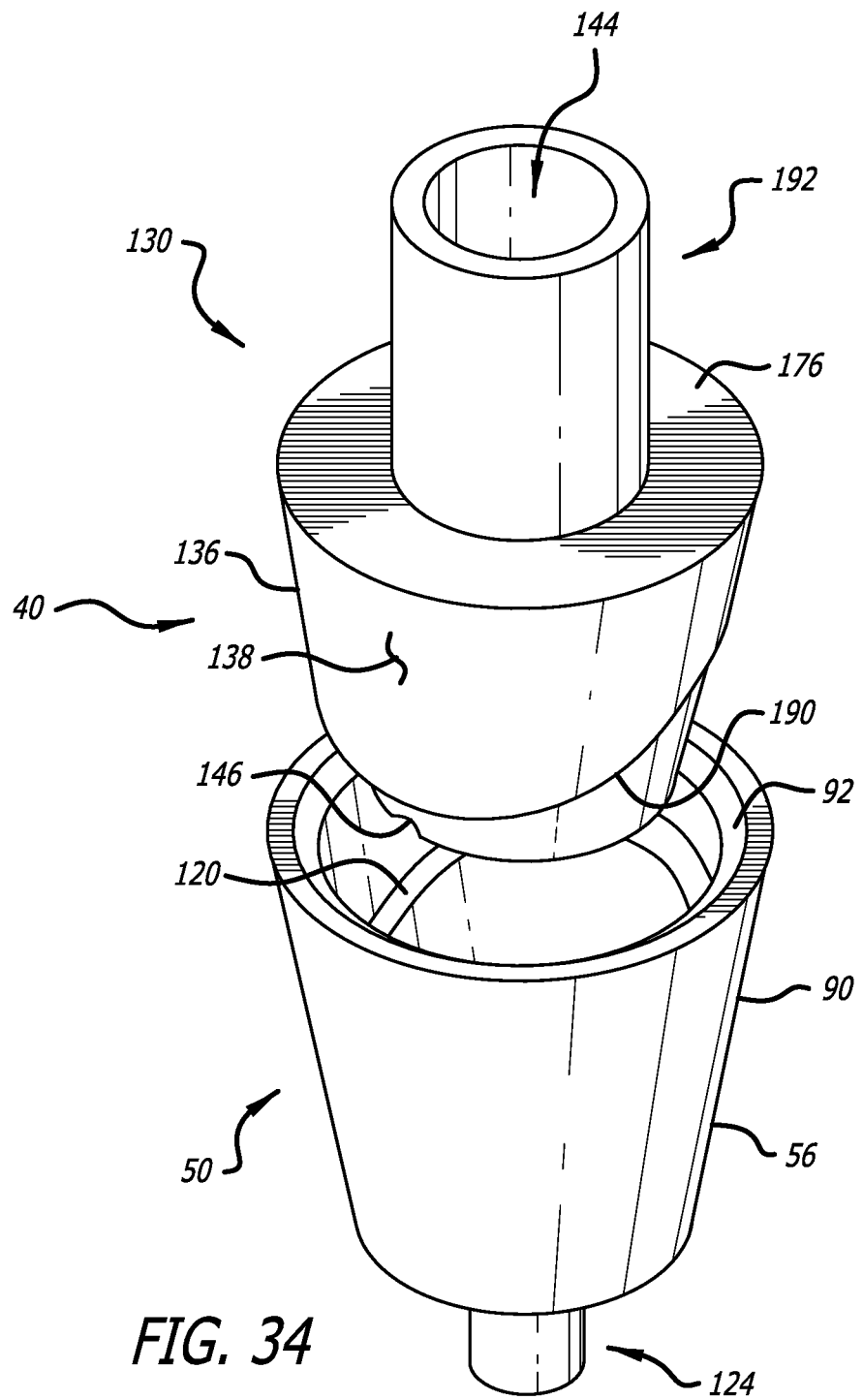
FIG. 34 illustrates an exploded perspective view of a further alternative exemplary drug delivery device according to aspects of the present invention.
Figure 35:
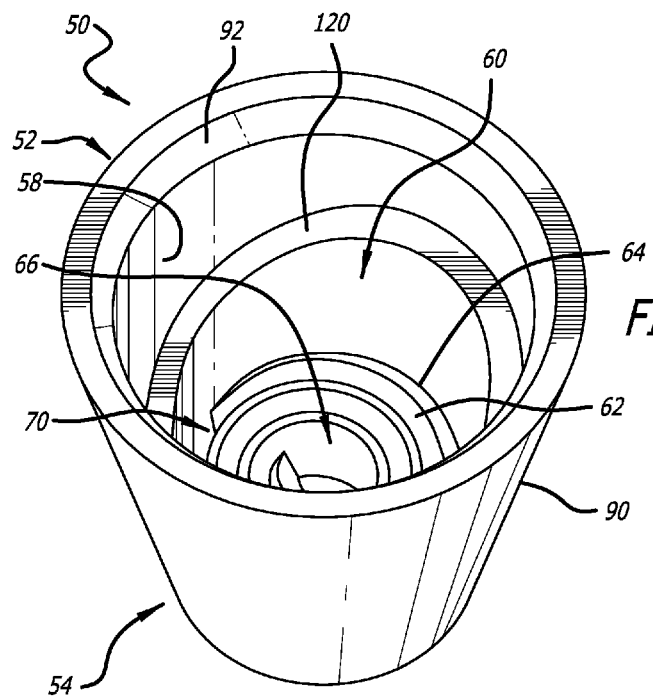
FIG. 35 illustrates an enlarged perspective view of an exemplary container component thereof.
Figure 36:
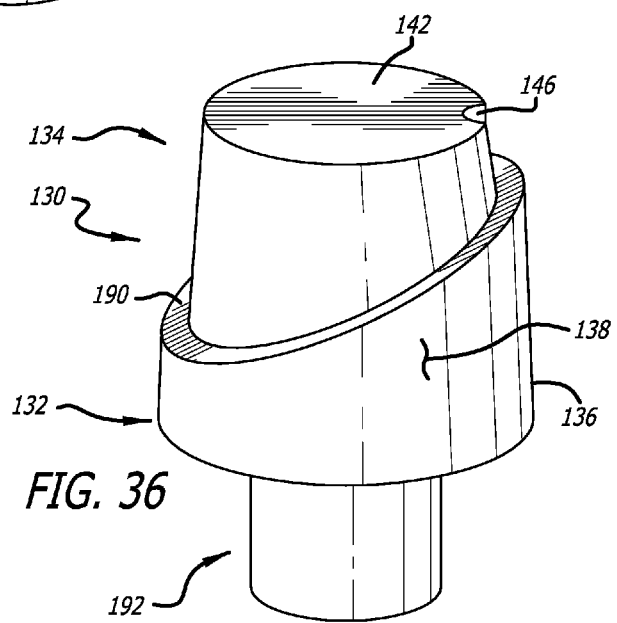
FIG. 36 illustrates an enlarged perspective view of an exemplary plug component thereof.
Figure 37:
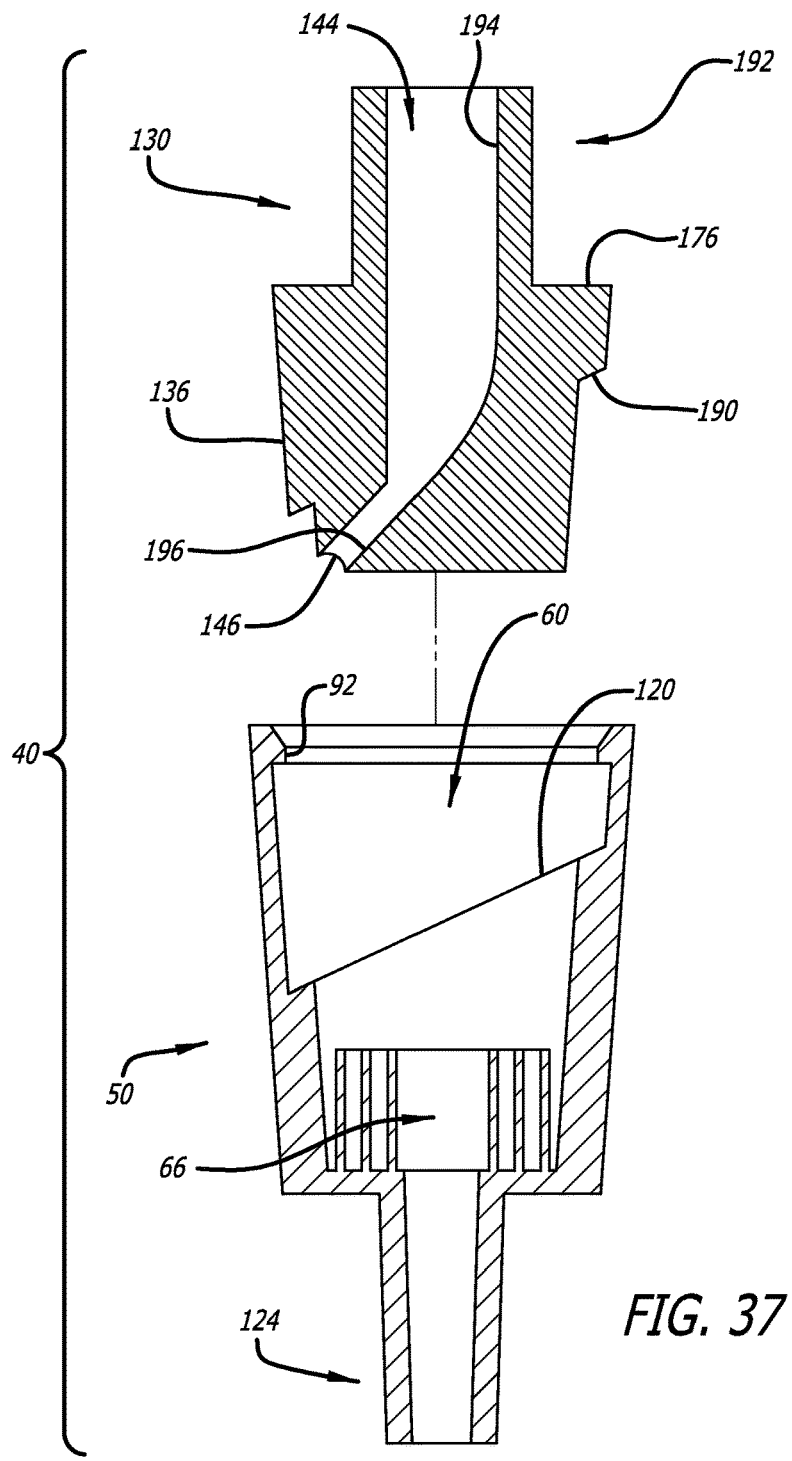
FIG. 37 illustrates an exploded side cross-sectional view thereof.

Turning now to particularly FIGS. 37-39, there are shown side cross-sectional views of the device 40 as in FIGS. 34-36 in various operational modes. First, in FIG. 37 there is provided an exploded view once again showing the container component 50 configured with a substantially proximally-facing ramped or sloped container indexing surface 120 and the plug component 130 configured with a corresponding substantially distally-facing ramped or sloped plug indexing surface 190. Once more, the container component 50 has an inner surface 58 (FIG. 35) defining an internal cavity 60 with a size selected to contain a predetermined quantity of a first constituent. Within the cavity 60 there is again formed the elongated mixing channel 66. Again, no interconnecting groove is formed in the inner surface 58 of the container component 50 and no distribution groove is formed in either the plug component 130 or the container component 50. Rather, upon assembly of the plug component 130 within the container component 50 in the second operational mode, as shown in FIG. 39, when the respective indexing surfaces 120, 190 are brought into substantially abutting relationship, the plug outlet port 146 is positioned substantially adjacent to the input end 70 (FIG. 35) of the mixing channel 66 so as to provide a direct flow path between the plug outlet port 146 and the ejection connector port 124. Further, in the exemplary embodiment, the plug outlet port 146 is positioned substantially adjacent the distal-most portion of the plug indexing surface 190. As shown, the internal flow path 144 through the plug component 130 from the inlet connector port 192 to the plug outlet port 146 is formed by an axial main bore 194 that then curves or transitions to a nominally transverse bore 196 that terminates in the plug outlet port 146. Again, a variety of other configurations of the flow path 144 through the plug component 130 and locations of the plug outlet port 146 are possible without departing from the spirit and scope of the invention.

Figure 41:
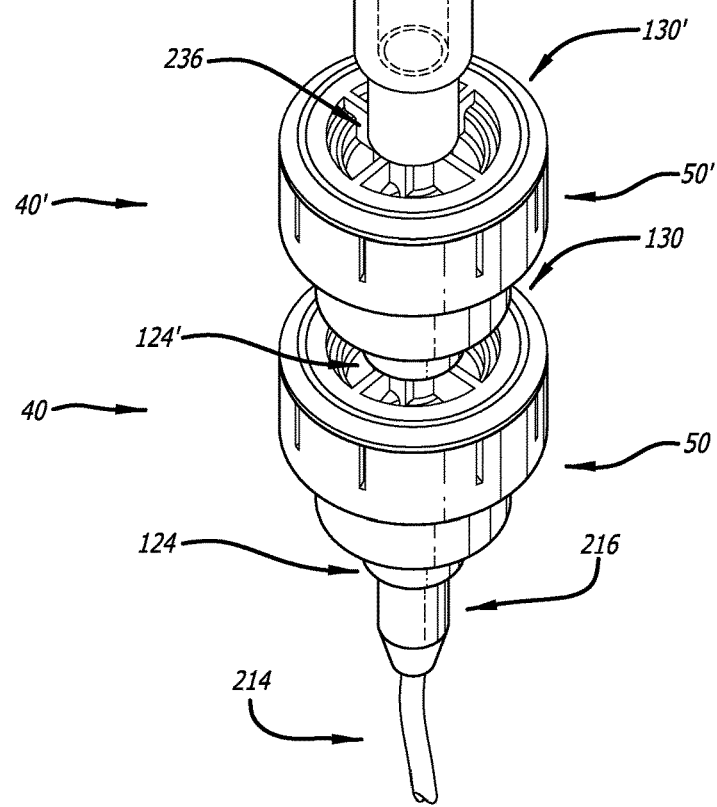
FIG. 41 illustrates a perspective view of two exemplary solution delivery devices according to aspects of the present invention as in FIGS. 1-6 shown connected in series.

Turning now to FIGS. 40 and 41 and a discussion of exemplary ones of the solution delivery device 40 according to aspects of the present invention in use, there is shown in FIG. 40 such a device 40 as seen in the exemplary embodiment of FIGS. 1-6 in one illustrative mode of use. Particularly, the outlet cap 200 (FIG. 6) has been removed so as to allow engagement of the external ejection connector port 124 with a cannula 210. In a manner known and used in the art, a cannula luer connector 212 is provided for removable engagement with a corresponding luer connector of the container connector port 124, such that the device 40 is thus configured for administration by injection of the first constituent housed within the device 40 as described herein. In an alternative embodiment, the cannula 210 may instead be formed integrally with the container component 50, and particularly the ejection connector port 124. Accordingly, the outlet cap 200 (FIG. 6) may be sized and configured, and particularly be of sufficient length, to house or contain the cannula 210 when not in use. In the exemplary context, once more, the first constituent is a lyophilized drug in the form of a powder contained particularly within the mixing channel 66 (FIG. 6) of the device 40. It is noted that the first constituent may start as a liquid and then be lyophilized in situ within the device as herein described, or it is possible that the drug already exists in powder form and is simply added to the container component 50 in that form ready for reconstitution. As such, the drug is to be reconstituted prior to injection or administration, which the device 40 according to aspects of the present invention conveniently and effectively enables without any separate mixing, shaking, reconstituting, or priming step. With continued reference to FIG. 40, any plug inlet cap 220 (FIG. 6) is removed from the plug inlet connector port 192 (FIG. 6) and a syringe 230 is connected thereto. Particularly, the syringe 230 may be formed at its distal end with a syringe luer connector 236 which is then removably engaged with the inlet connector port 192 configured as a corresponding luer connector so as to allow for fluid communication between the interior of the syringe barrel 232 and the interior of the device 40 as through the internal flow path 144 (FIG. 6) formed within the plug component 130 and in fluid communication with the inlet connector port 192 as well as the mixing channel 66 (FIG. 6) of the container component 50 as described herein. In an alternative exemplary embodiment, the syringe 230 or other such reservoir may be formed integrally with the plug component 130, and particularly the inlet connector port 192. Not shown, the syringe 230 would house a specified quantity of diluent, such that when the device 40 is connected to the syringe 230 as shown, advancing the plunger 234 distally within the syringe barrel 232 ejects the diluent or other fluid within the syringe 230 into the inlet connector port 192 (FIG. 6) of the solution delivery device 40 so as to flow through the plug component 130, enter the mixing channel 66 (FIG. 6) of the container component 50, and thus rapidly reconstitute the lyophilized drug that then exits the device 40 through the attached cannula 210. It will be appreciated by those skilled in the art that the mixing of the second constituent, here diluent, with the first constituent, here a lyophilized drug, from the input end to the output end of the elongated mixing channel allows for and in fact forces the mixing and reconstitution of the constituents over a gradient, whereby a delivery solution is formed having a medication concentration gradient as it flows out the external ejection connector port 124 with initial flow of delivery solution having a higher concentration of the medication than later flow of the delivery solution, whereby mixing and delivery occur in the same step and a separate reconstitution step is not necessary. In particular contexts it may be preferable to relatively rapidly advance the syringe plunger 234 so as to effectively force the diluent into the device 40 and thereby rapidly reconstitute the lyophilized drug. It will be further appreciated that the cannula 210 may itself be inserted within an injection site (not shown) for direct subcutaneous or intravenous delivery of the drug or inserted within an I.V. line connector or port (not shown) for other parenteral delivery. In either or any such case, the cannula 210 would be positioned as desired prior to advancing the syringe plunger 234 and commencing reconstitution and delivery of the drug. In one exemplary embodiment, the supplied volume of the second constituent, such as diluent delivered by the syringe 230, or the syringe or reservoir volume, is substantially equal to the predetermined quantity of the first constituent, here the liquid medication then lyophilized as a powder as contained within the mixing channel 66 (FIG. 6) of the container component 50. In an alternative embodiment, the supplied volume of the second constituent or syringe or reservoir volume is greater than the predetermined quantity of the first constituent, such as even double.

More particularly regarding the first and second constituents as may be reconstituted or mixed according to aspects of the present invention, again, in the illustrated embodiment the first constituent is substantially in powder form, as again being a lyophilized medication or an active lyophilized powder, for example, and the second constituent is substantially in liquid form, such as a diluent such as saline solution or sterile water for injection ("WFI") or an active diluent or constituent that is reactive with the first constituent, for example. Where the diluent is active, the first constituent may also be an inactive powder. In other embodiments and contexts, the first and second constituents are substantially in liquid form, or are both drugs, are a drug and a chemical, or are both chemicals, or a drug and a matrix, or are a drug and an albumin, or are a drug and an antibody fragment, or are a marker and an antibody fragment, or are a drug and a carrier, or are a drug and a targeting molecule, or are a diagnostic and a chemical, or any other combination thereof or employing any other such constituents in any manner or for any purpose now known or later developed. Where a chemical is employed as a constituent, in one embodiment the chemical extends the half-life of the delivery solution. In a further exemplary context, pre-mixing of the first and second constituents is undesirable, or forms a delivery solution having an unstable or undesirable pH, or forms a delivery solution having unstable storage beyond a particular shelf-life, including but not limited to five minutes, thirty minutes, one hour, or one day, or forms a delivery solution having unstable or undesirable formulation attributes, or causes increased aggregation, or causes increased crystallization, or is unstable at room temperature, or is unsupported by regulatory authorities, or causes an unwanted or premature chemical reaction, or any combination thereof or otherwise is not preferable. In other contexts, the use is further directed to drugs with limited solubility or with significant side effects having slow dissolving formulations selected as the first constituent contained within the internal cavity 60 of the container component 50. In still other exemplary contexts, the use is directed to non-injectable medical treatment, whereby the device 40 serves as more of a dispenser, such as for a topical application, nasal delivery, or inhalation, for example. While anticipated contexts for certain drugs and compositions such as epinephrine, antihistamine, antitoxin, antivenom, morphine, naloxone, glucose, aspirin, and adrenaline are expected to be emergency situations that might call for field use of an injector 240 such as disclosed and described further below in connection with FIGS. 42 and 43, it will be appreciated that such drugs or compositions and numerous others may also be administered more traditionally as by injection employing a set-up such as shown in FIG. 40 or any other such configuration. More generally, use of a device 40 according to aspects of the present invention, whether alone as in FIG. 40, in tandem as in FIG. 41, or as incorporated in an injector 240 as in FIGS. 42 and 43, may be directed to such situations, including but not limited to, as treatment of an allergic reaction, treatment of exposure to a toxin, treatment of exposure to a neurotoxin, treatment of a snake bite, pain management, treatment of opioid overdose, treatment of a heart attack, and treatment of any other such situation clinically called for according to then-current medical best practices. Furthermore, uses of a solution delivery device 40 according to aspects of the present invention may extend beyond clinical or medicinal, including but not limited to laboratory diagnostics, small volume lyophilized chemicals employed as reagents, and manufacturing processes. In any such context, other exemplary indications for use include, but are not limited to, removal of unwanted substances in one of a constituent, a delivery solution, or a sample by passage through the device 40 to capture the unwanted substances, wherein the unwanted substances are selected from the group consisting of unwanted chemicals, infectious substances, and impurities, and wherein the removal may be accomplished by chemical capture, chemical alteration, and/or mechanical means such as filtration. Accordingly, one exemplary aspect, the device 40 may be configured to operate as an affinity column or an affinity container, in one such exemplary embodiment the volume of the affinity container, or effectively of the internal cavity 60 of the container component 50, is in the range of 0.1 cc to 20.0 cc. In any such context, it will be appreciated that the use of the device 40 may further comprise parenteral administration of the delivery solution after the removal of unwanted substances.

More generally regarding use, and with reference to FIGS. 1-39, as will be appreciated from the present disclosure, a method is herein provided of employing a solution delivery device 40 according to aspects of the present invention including the following steps: (a) filling the predetermined quantity of the first constituent within the internal cavity 60 of the container component 50; (b) positioning the plug component 130 in the container component 50 in the first operational mode of the device 40 wherein the plug distal surface 142 is spaced from the first constituent; (c) acting on the first constituent with the device 40 in the first operational mode; (d) shifting the plug component 130 to the second operational mode of the device 40 wherein the plug component 130 is fully seated within the container component 50 and the plug distal surface 142 is substantially adjacent to the first constituent; and (e) flowing the second constituent through the internal flow path 144 formed within the plug component 130 and into the internal cavity 60 of the container component 50 so as to contact the first constituent, whereby the first and second constituents are sufficiently mixed in forming the delivery solution without the need for a separate mixing, shaking, reconstituting, or priming step. In one embodiment, step (a) is accomplished through a vial-fill assembly line process. Relatedly, a further step may entail removably installing a container outlet cap 200 on the external ejection connector port 192, the container outlet cap 200 serving to stand the container component 50 substantially upright during the filling step (a). Step (b) of positioning the plug component 130 in the container component 50 in the first operational mode allows for a vent gap whereby the internal cavity 60 of the container component is in fluid communication with the surrounding atmosphere. In the exemplary context, step (c) of acting on the first constituent with the device 40 in the first operational mode comprises subjecting the device 40 to a lyophilization process. It will be appreciated that any other such process, now known or later developed, may instead be employed, including but not limited to spray-drying, spray-freeze drying, bulk crystallization, vacuum drying, and foam drying, or any combination thereof. In the exemplary embodiment, step (d) of shifting the plug component 130 to the second operational mode comprises abutting the plug distal surface 142 on the wall top surface 64 of the elongated channel wall 62 installed within the internal cavity 60 of the container component 50 so as to form the mixing channel 66. It will be appreciated that such shifting and engaging step may entail snapping the plug component 130 within the container component 50, welding the plug component 130 within the container component 50, or bonding the plug component 130 within the container component 50, and may further comprise some form of tamper-proofing the device 40, such as by positioning the engagement surfaces of the components internally, or more particularly in one exemplary embodiment positioning a perimeter wall 114 about the engagement wall 90 of the container component 90 wherein are located the engagement surfaces. Step (e) regarding flowing the second constituent in the exemplary embodiment of FIG. 40 again comprises connecting a syringe 230 containing the second constituent to the external inlet connector port 192 of the plug component 130 and activating the syringe plunger 234 to force the second constituent through the internal flow path 144 and into the inner cavity 60 of the container component 50, which syringe 230 or reservoir may again be detachable from or integral with the plug component 130. In another embodiment, the second constituent may be supplied through an I.V. line connected to the external inlet connector port 192 of the plug component 130. Other uses may be directed to the substantially continuous infusion of drugs. As by increasing the physical size of the device 40 and/or by closely controlling the flow rate therethrough upstream or downstream of the device 40.

Referring now to FIG. 41, there is shown an alternative use or arrangement wherein two solution delivery devices 40, 40' according to aspects of the present invention are connected in series, as when two different drugs or other constituents are to be co-injected or otherwise injected substantially simultaneously, more about which is said below. As shown, essentially, the external ejection connector port 124' of a second device 40' is connected to the inlet connector port 192 (FIG. 6) of a first. As herein described, the "first" device 40 is considered the one directly connected here to an I.V. line 214 as through engagement of an I.V. luer connector 216 with the first device's ejection connector port 214; as such, the first device 40 contains the first constituent. The "second" device 40' is connected in series above or "upstream" of the first device 40 and so would effectively provide the second constituent, rather than such being sourced directly from the syringe 230. As such, the second device 40' is again connected to the first device 40 distally, and as shown, proximally the syringe 230 is connected to the second device 40' as again by luer connector engagement or other such technique now known or later developed in the art. It will be appreciated that such connection of one device 40 to another 40' may be facilitated, for example, by configuring each external inlet connector port 192 as a female luer connector and each external ejection connector port 124 as a male luer connector, wherein the male and female luer connectors are sized so as to be selectively engageable one with the other. Accordingly, in use configured as shown, activation of the plunger 234 of the syringe 230 serves to eject from the barrel 232 and into the second device 40' a diluent or other such fourth constituent so as to reconstitute or otherwise mix with a further third constituent located within the second device 40'. In this manner, the delivery solution form the second device 40', such as a reconstituted drug in substantially liquid form, then becomes the second constituent forced out the second device 40' and into the first device 40 so as to then reconstitute or otherwise mix with the first constituent contained therein and then eject from the ejection connector port 124 of the first device 40 a final delivery solution that is effectively a mixture in some form of a first drug or other constituent from the first device 40 and a second drug or other constituent from the second device 40'. In one exemplary embodiment, the first constituent is one of a lyophilized medicine, an active lyophilized powder, and an inactive powder and the second constituent is a reconstituted drug. It will be appreciated by those skilled in the art that a virtually infinite variety of mixtures or co-injections of first to fourth constituents are possible, including but not limited to a drug, a chemical, a matrix, an albumin, an antibody fragment, a marker, a carrier, a targeting molecule, a diagnostic, and a diluent or any combination thereof. It will be appreciated that any such combination is possible by selectively linking or connecting in series appropriate pre-filled solution delivery devices according to aspects of the present invention along with an upstream syringe or other such constituent source. Regardless, and similar to the usage depicted by FIG. 40, the step of connecting the I.V. line 214 to the external ejection connector port 124 of the first device 40 preferably is done prior to the step of flowing the second constituent from the second device 40'. It will further be appreciated that any number of devices 40 may be connected in series as shown, such that the two in series is to be understood as merely illustrative of aspects of the present invention and non-limiting. Moreover, there may be contexts where two or more solution delivery devices are instead connected in parallel rather in series and are configured to communicate distally with a common injection or infusion site and proximally with one or more second constituent sources, such as, for example, a common syringe or other reservoir or device for supplying a second constituent to the, in this example, two or more solution delivery devices connected in parallel. Such an alternative approach may be employed, for example, where using a reconstituted drug to then reconstitute a second drug has or might have adverse consequences, where more precise dosing of one or both drugs is required, or where any other unwanted or undesired effect of "in series" reconstitution and delivery renders an "in parallel" approach more preferable.

In use with multiple solution delivery devices 40 according to aspects of the present invention employing a configuration such as shown in FIG. 41, exemplary applications or contexts include, but are not limited to: (a) administration of a drug in combination with an anesthetic indicated for use in reducing side effects associated with the drug, wherein the side effects are one or more of pain, itching, and neurological symptoms associated with administration of the drug; (b) administration of a drug in combination with an anti-inflammatory indicated for use in reducing side effects associated with the drug, wherein the side effects are one or more of pain, fever, immune responses, and inflammation associated with administration of the drug; (c) administration of two drugs in combination having synergistic effects, wherein the drugs are two different pain medications and the synergistic effect is each drug having a different mechanism of action or wherein the drugs have different PK or PD profiles; (d) substantially simultaneous administration of fixed dose drug combinations; and (e) substantially simultaneous administration of weight-based dose drug combinations.

Figure 42A:
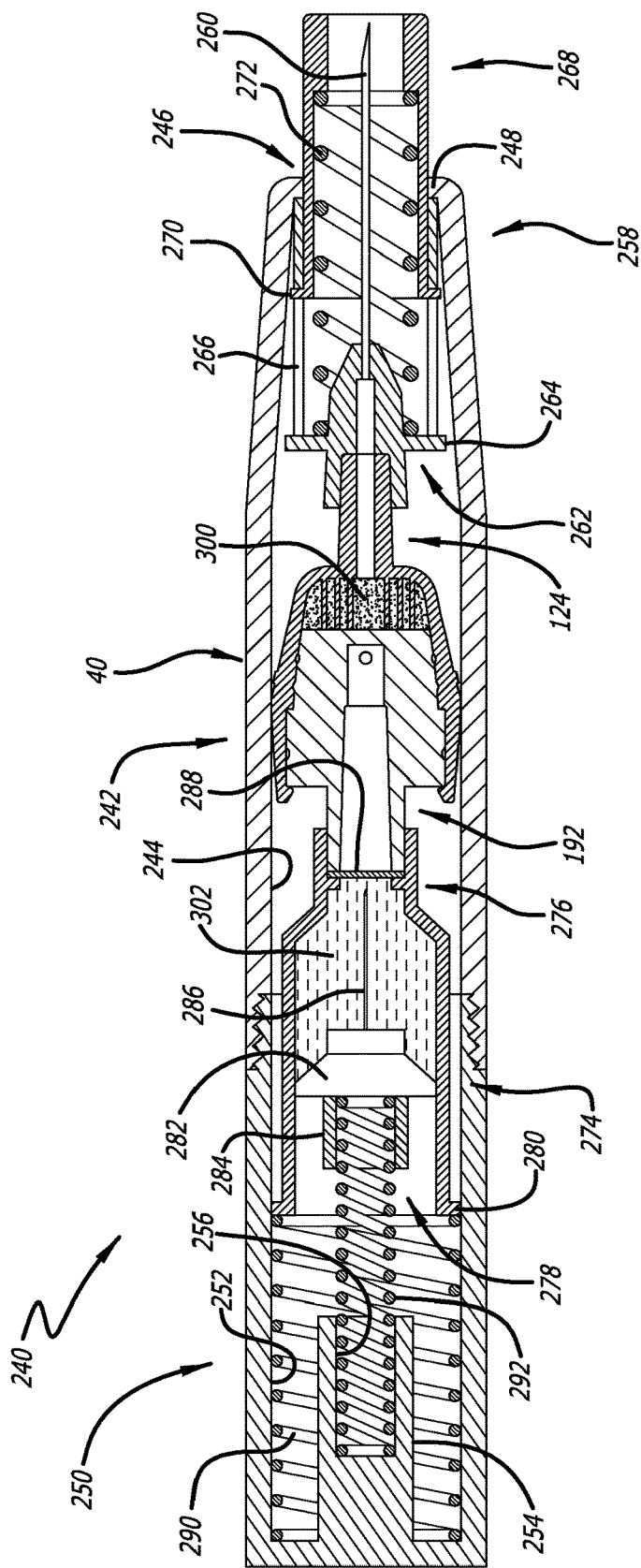
FIG. 42A illustrates a side schematic view, partially in section, of an exemplary solution delivery device according to aspects of the present invention as in FIGS. 13-18 shown operably installed within a medical injector in a first operational mode.
Figure 42B:
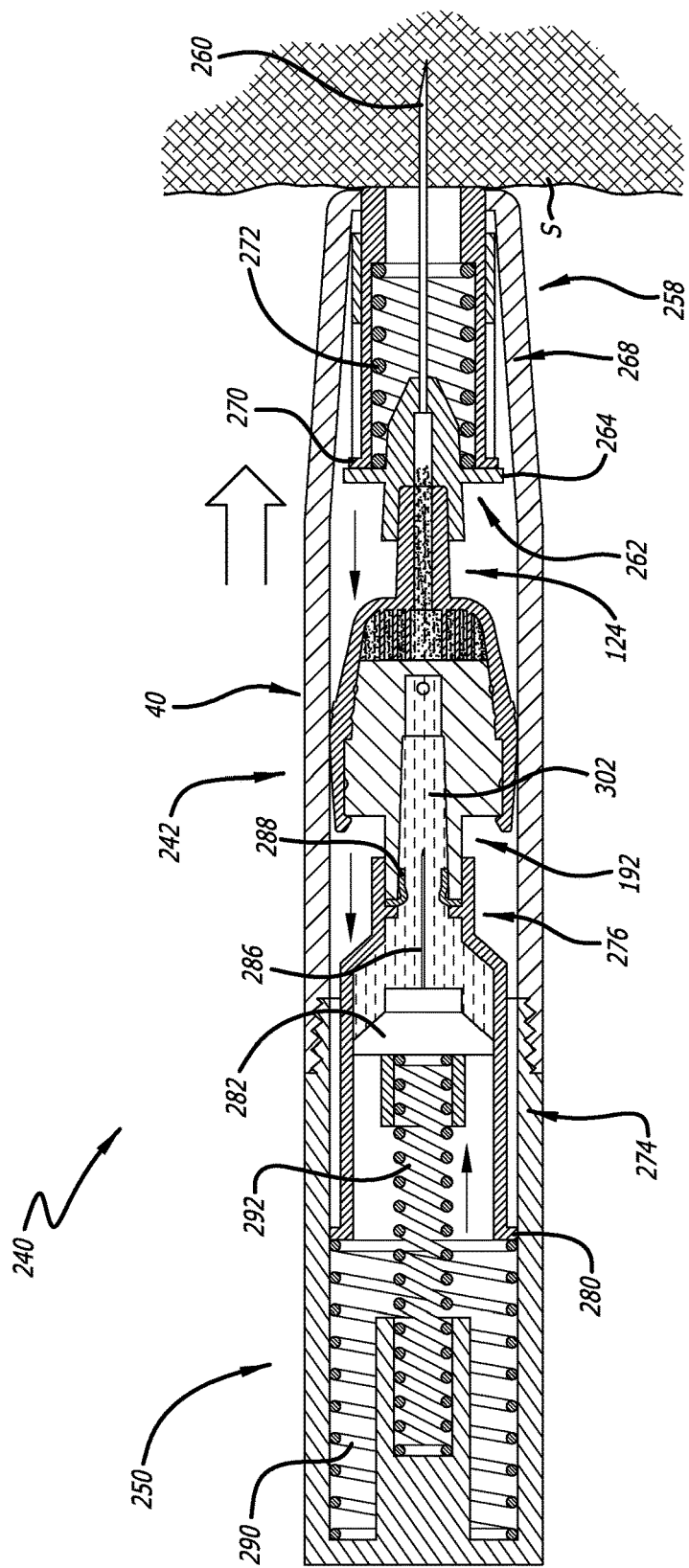
FIG. 42B illustrates a side schematic view, partially in section, of the exemplary solution delivery device shown operably installed within a medical injector as in FIG. 42A, now in a second operational mode.

Finally, turning now to FIGS. 42A and 42B, there is shown in sectional view in two operational modes an exemplary solution delivery device 40 according to aspects of the present invention as incorporated within an injector 240. First, with reference to FIG. 42A, in an "at rest" configuration of the device 240, there is shown internally a sub-assembly generally comprising the solution delivery device 40, here as per the exemplary embodiment shown in FIGS. 13-18, with a cannula assembly 258 connected to the device 40 distally and a reservoir 274 connected to the device 40 proximally, the three components then axially slidably installed effectively as a unit within the housing 242 of the injector 240, the housing having an inner bore generally denoted 244. An assembly spring 290 is installed at the proximal end of the injector 240 substantially between a housing proximal cap 250 and a proximal reservoir opening flange 280 so as to gently bias the sub-assembly distally within the housing 242. As shown, the cap 250 has an inner cap bore 252 that is substantially equivalent to the housing bore 244, though not necessarily so. In particular, distal travel of the sub-assembly is substantially prevented beyond the distal end of the housing 242 by engagement of the cannula body 266 with the housing opening flange 248 formed at the housing distal opening 246 through which a portion of the cannula assembly 258 extends. More particularly regarding the cannula assembly 258, as shown, there is provided a distally extending cannula 260 mounted proximally within a cannula connector 262 that is itself engaged with the external ejection connector port 124 of the solution delivery device 40. The cannula connector 262 is further formed with a radial connector flange 264 from which extends distally or to which is otherwise installed or on which is otherwise formed a cannula body 266. Operably and slidably installed within the cannula body 266 is a cannula shield 268 having a shield flange 270 configured for traveling or seating between a distal portion of the cannula body 266 and proximally against the connector flange 264. Notably, a cannula spring 272 is positioned within the cannula assembly 258 substantially between the cannula shield 268 and the connector flange 264 so as to gently bias the cannula shield 268 distally, which it will be appreciated serves to shield or substantially enclose the cannula 260 that extends beyond the distal end of the injector housing 242, thereby protecting against inadvertent needle sticks. Proximally, once more, a reservoir 274 is configured with a distal reservoir connector 276 for selective engagement with the proximal inlet connector port 192 of the solution delivery device 40. As shown, operable within the reservoir 274 as inserted via the proximal reservoir opening 278, and thereby effectively closing such opening, is a reservoir plunger 282. The plunger 282 is configured proximally with a boss 284 engaged by a plunger spring 292 substantially fixed at its opposite proximal end within a bore 256 of a cap post 254 extending distally from the housing proximal cap 250. It will be appreciated by those skilled in the art that the plunger spring 292 serves to distally bias the plunger 282 within the reservoir 274 against the liquid contained therein, here the second constituent 302. Notably, a membrane 288 is installed as a temporary fluid impermeable barrier between the reservoir 274 and the solution delivery device 40 so as to prevent unwanted or premature mixing of the second constituent 302 such as a diluent and the first constituent 300 such as a lyophilized drug contained within the device 40, which would be self-defeating. As shown in the exemplary embodiment, the membrane 288 is positioned substantially at the proximal end of the device's inlet connector port 192 so as to effectively cap the port 192 as the distal reservoir connector 276 is installed thereon. So positioned or trapped so as to span the opening to the inlet connector port 192, it will thus be appreciated that the membrane 288 thereby prevents the flow of any liquid first constituent 302 out of the reservoir 274. Those skilled in the art will appreciate that any and all such components may be formed integrally, such as the reservoir 274 or the cannula assembly 258 with the solution delivery device 40, or may be formed separately and installed as shown. It will be further appreciated that the membrane 288 must be selectively overcome or otherwise removed as a barrier to then allow flow of the second constituent 302 into the delivery device 40, more about which is said below in connection with FIG. 42B. Generally, the membrane 288 is sized and configured to withstand the pressure exerted on it in the "at rest" configuration of the injector 240 shown in FIG. 42A as by the column of fluid within the reservoir 274 under pressure from the plunger 282 as biased distally by the plunger spring 292 as described above. In other words, the injector 240, and particularly the plunger 282 and membrane 288, is "pre-loaded" by the plunger spring 292. In one approach, then, the membrane 288 design in terms of material and thickness and perhaps even perforations or the like is such that in the "at rest" configuration with the pressure exerted by the pre-loaded spring 292 and plunger 282 the membrane 288 will not fail or rupture but a selected increase in pressure over the "at rest" or "pre-load" pressure would then cause the membrane 288 to fail or rupture and thus allow the flow of the second constituent 302 from the reservoir 274 again under the influence of the plunger 282 as biased distally by the pre-loaded plunger spring 292. Instead of or in addition to such a pressure-balancing approach to the membrane 288, there is also shown in FIG. 42A, alternatively, a piercing tip 286 configured on the plunger 282 so as to extend distally therefrom substantially in the direction of and toward the membrane 288. It should be understood that on that basis any further appreciable distal movement of the plunger 282 may thus bring the piercing tip 286 into contact with the membrane 288 so as to cause or aid in its failure. In one exemplary embodiment, the distance from the piercing tip 286 to the membrane 288 is less than the range of proximal travel of the device sub-assembly within the housing 242 as dictated, at least in part, by the difference between the length of the cannula shield 268 exposed beyond the distal end of the housing 242 and the distance of proximal travel of the shield flange 270 back into abutment against the connector flange 264, at which point further proximal travel of the shield 268 translates to proximal travel of the entire cannula assembly 258, the solution delivery device 40, and the reservoir 274, thereby effectively shifting the plunger 282 distally within the reservoir 274 and the piercing tip 286 toward the membrane 288.

Referring to FIG. 42B now showing the injector 240 activated versus the "at rest" configuration of FIG. 42A, as when the injector 240 is to be used in subcutaneous injection of a drug, it will be appreciated that proximal, somewhat axial pressure or force on the cannula shield 268 pushes the shield 268 proximally so as to expose the cannula 260 and allow its insertion into the skin S. Continued force on the cannula shield 268 against the biasing effect of the cannula spring 272 shifts the cannula shield 268 proximally until the shield flange 270 is brought into contact with the cannula connector flange 264 as shown, at which point further proximal force on the cannula shield 268, though likely earlier, begins to shift the sub-assembly of the cannula assembly 258, the solution delivery device 40, and the reservoir 274 proximally within the injector housing 242 against the minimal resistance of the assembly spring 290. Accordingly, with particularly the reservoir 274 shifting proximally while the reservoir plunger 282 remains substantially in the same position spatially under the distal biasing and pre-loading of the plunger spring 292, it will be appreciated that the piercing tip 286 comes into contact with the membrane 288 such that, in cooperation with the building pressure exerted on the second constituent 302 by the plunger 282 again under the influence of the plunger spring 292, the membrane 288 thereby fails as shown, allowing the second constituent 302 to flow out of the reservoir 274 and through the inlet connector port 192 into the solution delivery device 40 where it encounters and reconstitutes or otherwise mixes with the first constituent contained therein as described, which delivery solution such as a reconstituted drug then exits the delivery device 40 through the ejection connector port 124 and makes its way into the cannula 260 for subcutaneous injection or other such administration. Those skilled in the art will appreciate that with the plunger spring 292 being pre-loaded and under increasing pressure during the injection or activation event of the injector 240, once the membrane 288 ruptures and there is no longer any appreciable constraint on or resistance to the distal travel of the plunger 282, the second constituent is expelled from the reservoir 274 substantially rapidly. In one embodiment, the rate of such expulsion under the influence of the plunger spring 292, or as a function of its spring rate and configuration, substantially approximates the rate of ejection and reconstitution typically achieved through a manual operation employing a syringe 230 as in the embodiments of FIGS. 40 and 41. It will be appreciated, however, that a variety of spring and ejection rates are possible based on a number of factors, such that the present invention is not so limited. Moreover, it will be further appreciated that a variety of configurations of the injector 240 and its various components are possible as well, whether now known or later developed, such that the injector 240 shown and described is to be understood as being merely illustrative of features and aspects of the present invention and expressly non-limiting. In one exemplary embodiment, the membrane 288 is made of a material including but not limited to silicone, polyester, or foil and has a thickness in the range of 1 to 1,000 microns. It will be appreciated that such an injector 240 is generally configured for single use and to thereby be disposable. However, it will be further appreciated that in certain contexts, particularly for example where the reservoir 274 and the cannula assembly 258 are integral with the solution delivery device 40, such a sub-assembly may be replaced in a cartridge fashion within an injector housing 242 that is not disposable or is reusable. By way of further illustration and as a non-limiting exemplary list of the kinds of drugs and other compositions that may be stored in and reconstituted and administered by an injector 240 according to aspects of the present invention particularly in conjunction with a solution delivery device 40 as is disclosed herein, such delivery solutions may include but are not limited to epinephrine, antihistamine, antitoxin, antivenom, morphine, naloxone, glucose, aspirin, and adrenaline. It will be appreciated that any such drugs or compositions may be administered to humans or animals in an emergency, wherein the fail-safe and substantially instantaneous administration of a reconstituted drug as by an injector 240 according to aspects of the present invention presents a number of significant and potentially life-saving advantages. Moreover, by storing the drug or other composition in a dry powder form such as a lyophilized medicine, the storage or shelf-life of the drug and hence the injector 240 is increased dramatically, an important consideration knowing that such injectors or auto-injectors may be kept on hand for months if not years "just in case" an emergency situation arises. It is or course desirable that the injector 240 still be operable and the lyophilized drug still be efficacious at the point of use, however long after original manufacture might be, notwithstanding the instructions and expiration warnings that of course may be contained on or packaged with the injector 240.

Figure 43A:
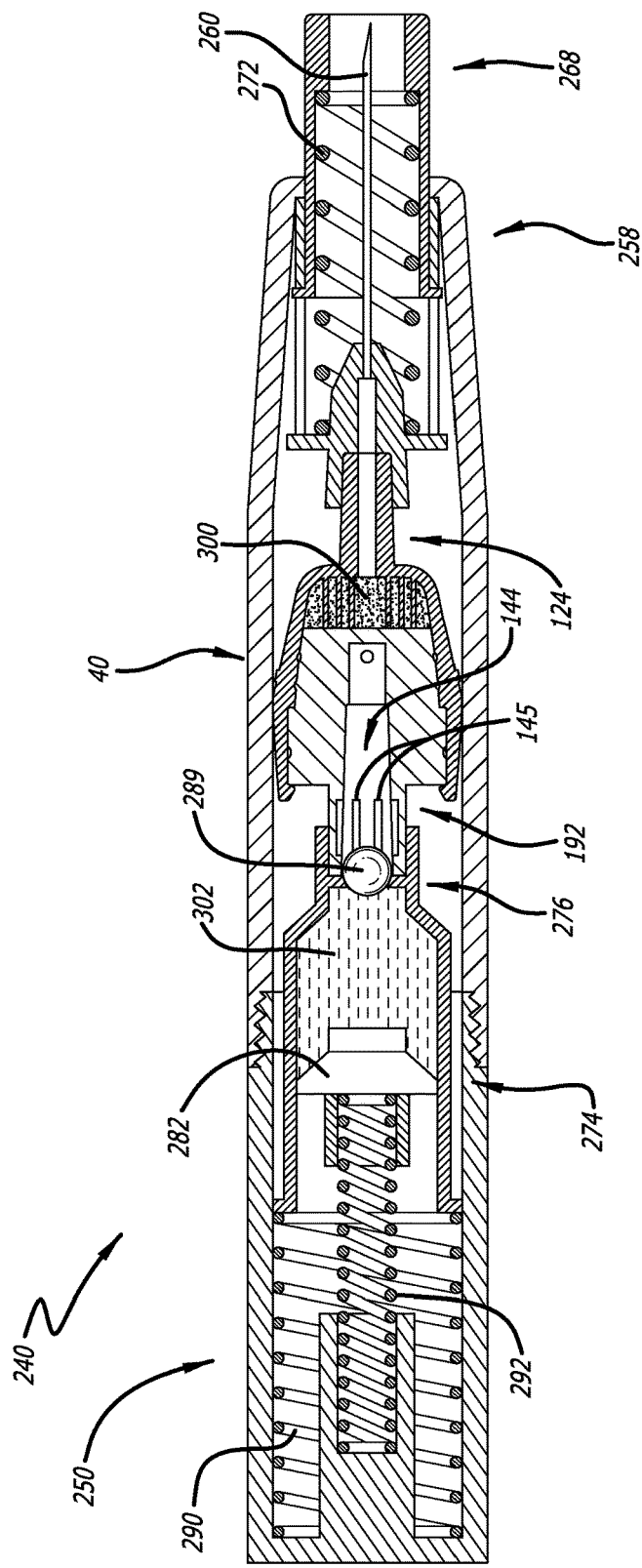
FIG. 43A illustrates a side schematic view, partially in section, of an alternative exemplary solution delivery device according to aspects of the present invention shown operably installed within a medical injector in a first operational mode.
Figure 43B:
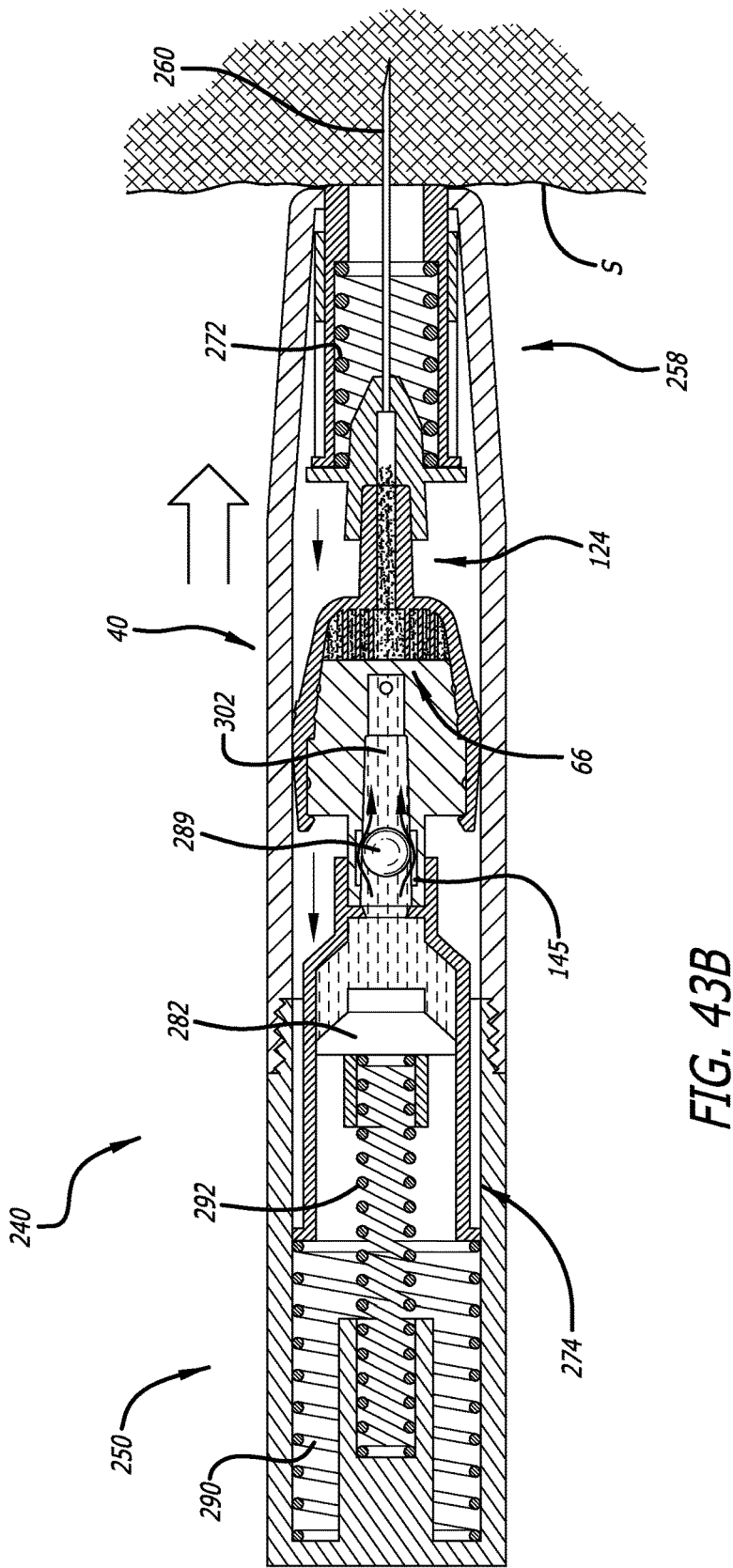
FIG. 43B illustrates a side schematic view, partially in section, of the alternative exemplary solution delivery device shown operably installed within a medical injector as in FIG. 43A, now in a second operational mode.

Similarly, referring to FIGS. 43A and 43B, there is shown in sectional view in two operational modes an alternative exemplary solution delivery device 40 according to aspects of the present invention as incorporated within an injector 240. Essentially, in comparison with the embodiment of FIGS. 42A and 42B, the membrane 288 positioned within the distal reservoir connector 276 has been replaced with a sealing plug 289 that is to be dislodged under pressure so as to allow flow rather than the membrane 288 rupturing, as assisted in the first exemplary embodiment by the piercing tip 286, which is not needed and so removed in the alternative embodiment of FIGS. 43A and 43B. In a bit more detail, first with reference to FIG. 42A, in an "at rest" configuration of the device 240, there is shown internally a sub-assembly generally comprising the solution delivery device 40, here as per the exemplary embodiment shown in FIGS. 13-18, with a cannula assembly 258 connected to the device 40 distally and a reservoir 274 connected to the device 40 proximally, the three components then axially slidably installed effectively as a unit within the housing 242 of the injector 240. An assembly spring 290 is installed at the proximal end of the injector 240 so as to gently bias the sub-assembly distally within the housing 242. The reservoir 274 is configured with a distal reservoir connector 276 for selective engagement with the proximal inlet connector port 192 of the solution delivery device 40. As shown, operable within the reservoir 274 is a reservoir plunger 282 engaged by a plunger spring 292 that serves to distally bias the plunger 282 within the reservoir 274 against the liquid contained therein, here the second constituent 302. Notably, once more, here a sealing plug 289 is frictionally installed within the distal reservoir connector 276 as a temporary fluid impermeable barrier between the reservoir 274 and the solution delivery device 40 so as to prevent unwanted or premature mixing of the second constituent 302 such as a diluent and the first constituent 300 such as a lyophilized drug contained within the device 40, which would be self-defeating. As shown in the exemplary embodiment, the plug 289 is positioned substantially at the proximal end of the device's inlet connector port 192 so as to effectively cap the port 192 as the distal reservoir connector 276 is installed thereon. So positioned or trapped so as to span the opening to the inlet connector port 192, it will thus be appreciated that the plug 289 thereby prevents the flow of any liquid first constituent 302 out of the reservoir 274. Those skilled in the art will appreciate that any and all such components may be formed integrally, such as the reservoir 274 or the cannula assembly 258 with the solution delivery device 40, or may be formed separately and installed as shown. It will be further appreciated that the frictional engagement of the plug 289 within the distal reservoir connector 276 must be selectively overcome or otherwise removed or shifted as a barrier to then allow flow of the second constituent 302 into the delivery device 40, more about which is said below in connection with FIG. 43B. Generally, the plug 289 is sized and configured to withstand, as by not being dislodged the pressure exerted on it in the "at rest" configuration of the injector 240 shown in FIG. 43A as by the column of fluid within the reservoir 274 under pressure from the plunger 282 as biased distally by the plunger spring 292 as described above. In other words, the injector 240, and particularly the plunger 282 and plug 289, is "pre-loaded" by the plunger spring 292. In one approach, then, the plug 289 design in terms of material (elasticity and surface friction) and size (diameter) is such that in the "at rest" configuration with the pressure exerted by the pre-loaded spring 292 and plunger 282 the plug 289 will not become dislodged or shift distally within the distal reservoir connector 276 toward or further down into the inlet connector port 192 of the delivery device 40, but a selected increase in pressure over the "at rest" or "pre-load" pressure would then cause the plug 289 to dislodge and thus allow the flow of the second constituent 302 from the reservoir 274 again under the influence of the plunger 282 as biased distally by the pre-loaded plunger spring 292. As shown, facilitating both the distal movement of the sealing plug 289 and the flow around it of the second constituent 302 when the plug 289 shifts distally within the reservoir connector 276 and the connector port 192, there is formed within the connector port 192 lengthwise flow path notches 145. It will be appreciated that while the plug 289 may be in contact with and even have a net or sealing engagement with the nominal inside diameter surface of the connector port 192 (axial bore 194 in FIG. 16), the notches 145 define undercuts or gaps between the plug 289 and the axial bore 194 of the connector port 192 for fluid flow around the plug 289 and here on through the flow path 144.

It will be appreciated by those skilled in the art that a wide variety of configurations of temporary seals for the reservoir 274 of the injector 240 including different kinds of plugs and different mechanisms for their selective engagement within and release from the distal reservoir connector 276 are possible according to aspects of the present invention. Moreover, as needed, various structures for selectively providing or allowing for a flow path through the inlet connector port 192 are also possible without departing from the spirit and scope of the invention.

It will be appreciated from the foregoing that in various contexts and anticipated or intended uses of the solution delivery device 40 according to aspects of the present invention such a device may be packaged with other related components and provided together as a kit. For example, in addition to the device 40 itself in whatever configuration, such a kit may also include a container outlet cap 200 removably installed on the external ejection connector port 124 of the container component 50 and a plug inlet cap 220 removably installed on the external inlet connector port 192 of the plug component 130. By way of further example, such a kit may instead or additionally include a cannula 210, an I.V. line 214 and/or a syringe 230. In the case of inclusion of a cannula 210, once more, the cannula 210 may be removably installed on the external ejection connector port 124 of the container component 50 or may be formed integrally with the ejection connector port 124. When any such cannula 210 is included in the kit, a container outlet cap 200 is preferably included as well and removably installed on the external ejection connector port 124 of the container component 50 substantially about the cannula 210 so as to help prevent inadvertent needle sticks. Further, the kit may also include a reservoir in a form other than a syringe or formed integrally with the plug component.130. The kit may instead or additionally include an injector 240, in which case preferably the solution delivery device 40 is pre-installed within the injector 240 and ready for use. Finally, any such kit will include instructional material at least providing instructions on how to use the device 40 or perform methods consistent with the present disclosure employing the device 40.

Aspects of the present specification may also be described as follows:

1. A solution delivery device comprising:
  a container component having a base wall with an inner surface and within which is formed an internal cavity with a size selected to contain a predetermined quantity of a first constituent, the container component further having a distal end with an external ejection connector port;
  a plug component configured for selective engagement with the container component in at least first and second operational modes, the plug component having a proximal end, a distal end, and a side wall having an outer surface disposed between the ends, the side wall and distal end together defining a plug periphery, the plug component further having an external inlet connector port substantially at the proximal end and an internal flow path from the inlet connector port to a plug outlet port intersecting the plug periphery, the plug component being formed on the distal end with a plug distal surface; and
  an elongated channel wall installed within the internal cavity of the container component to form an elongated mixing channel, the channel wall having a wall top surface and being located within the container component such that the mixing channel has a substantially closed bottom and an open top adjacent the wall top surface, the mixing channel having an input end in fluid communication with the plug outlet port and an output end in fluid communication with the ejection connector port;

wherein the wall top surface of the elongated channel wall is located within the container component facing the plug component so that when the plug component and the container component are fully assembled together in the second operational mode, the plug distal surface contacts the wall top surface and substantially closes the top of the elongated mixing channel so that the only access to the first constituent is provided by the input and output ends of the mixing channel; and wherein forcing a second constituent through the inlet connector port causes the second constituent to flow through the internal flow path of the plug component and out the plug outlet port and into the input end of the mixing channel so as to mix with the first constituent, whereby the first and second constituents are sufficiently mixed as together traversing the mixing channel from the inlet end to the outlet end and then out through the ejection connector port as a delivery solution without the need for a separate mixing, shaking, reconstituting, or priming step.

2. The device according to Embodiment 1, wherein the container component further comprises an interconnecting groove formed in the inner surface of the base wall so as to be in fluid communication with the input end of the mixing channel.

3. The device according to Embodiment 2, wherein the interconnecting groove is substantially lengthwise along the container component base wall.

4. The device according to Embodiment 2 or Embodiment 3, wherein the interconnecting groove is of sufficient length to be in fluid communication with the plug outlet port upon assembly of the plug component within the container component in the second operational mode, whereby the mixing channel provides an indirect flow path between the plug outlet port and the ejection connector port.

5. The device according to any of Embodiments 2-4, wherein the container component further comprises a distribution groove formed in the inner surface of the base wall so as to be in fluid communication with the interconnecting groove.

6. The device according to any of Embodiments 2-4, wherein the plug component further comprises a distribution groove formed in the outer surface of the side wall so as to be in fluid communication with the plug outlet port.

7. The device according to Embodiment 5 or Embodiment 6, wherein the distribution groove is annular.

8. The device according to any of Embodiments 5-7, wherein the distribution groove is continuous.

9. The device according to Embodiment 5, wherein the distribution groove is formed as an upwardly-opening step in the inner surface of the base wall, such that the base wall has a stepped inner bore.

10. The device according to Embodiment 9, wherein the step is angled so as to provide a countersink transition to the inner surface of the base wall beneath the step.

11. The device according to Embodiment 9 or Embodiment 10, wherein the step has a depth terminating along the inner surface of the base wall proximal of the channel wall top surface, thereby forming a container seating portion of the inner surface between the step and the mixing channel.

12. The device according to Embodiment 5, wherein the distribution groove is formed as an inwardly-opening circumferential recess in the inner surface of the base wall.

13. The device according to Embodiment 12, wherein the recess is positioned in the inner surface of the base wall proximal of the channel wall top surface, thereby forming a container seating portion of the inner surface between the recess and the mixing channel.

14. The device according to Embodiment 6, wherein the distribution groove is formed as an outwardly-opening circumferential recess in the outer surface of the side wall intersected by the plug outlet port.

15. The device according to Embodiment 14, wherein the recess is positioned in the outer surface of the side wall proximal of and spaced from the distal end of the plug component, thereby forming a plug seating portion of the outer surface between the recess and the distal end.

16. The device according to Embodiment 5 or Embodiment 6, wherein the plug outlet port is located in the side wall proximal of a plug seating portion, whereby upon assembly of the plug component within the container component in the second operational mode the plug outlet port is adjacent to and in fluid communication with the distribution groove.

17. The device according to any of Embodiments 1-16, wherein the outer surface of the side wall of the plug component is formed having a plug seating portion configured to seat against a container seating portion of the inner surface of the base wall of the container component upon assembly of the plug component within the container component in the second operational mode.

18. The device according to Embodiment 17, wherein the plug seating portion and the container seating portion are configured for a net-fit engagement.

19. The device according to Embodiment 17 or Embodiment 18, wherein the plug seating portion and the container seating portion are straight-walled.

20. The device according to Embodiment 17 or Embodiment 18, wherein the plug seating portion and the container seating portion are curve-walled.

21. The device according to Embodiment 17 or Embodiment 18, wherein the plug seating portion and the container seating portion are tapered.

22. The device according to any of Embodiments 1-21, wherein the base wall terminates proximally in a substantially radially-outwardly extending container flange having a proximally extending engagement wall.

23. The device according to Embodiment 22, wherein the engagement wall is substantially annular.

24. The device according to Embodiment 22 or Embodiment 23, wherein the engagement wall terminates proximally in a radially-inwardly projecting engagement lip.

25. The device according to Embodiment 24, wherein the engagement lip is configured to engage an outwardly-opening engagement groove formed in the outer surface of the side wall of the plug component.

26. The device according to Embodiment 25, wherein the engagement groove is formed between a proximal radially-outwardly extending plug flange and a distally offset radially-outwardly projecting retention lip.

27. The device according to any of Embodiments 24-26, wherein the engagement lip is substantially continuous.

28. The device according to Embodiment 24 or Embodiment 27, wherein a radially-outwardly projecting retention lip is formed on the outer surface of the side wall of the plug component and configured for selective engagement with the radially-inwardly projecting engagement lip of the container component.

29. The device according to Embodiment 28, wherein the retention lip defines a substantially proximally-facing engagement groove proximally engaged by the engagement lip upon assembly of the plug component within the container component in the second operational mode.

30. The device according to any of Embodiments 25-29, wherein:
the plug component is formed having a stepped side wall defined by a distally-facing shoulder separating a relatively larger diameter proximal plug engagement portion from a relatively smaller diameter distal plug seating portion; and
the distance from the engagement lip to the container flange of the container component is substantially equivalent to the distance from the engagement groove to the shoulder of the plug component, whereby engagement of the engagement lip within the engagement groove upon assembly of the plug component within the container component in the second operational mode substantially positions the shoulder of the plug component adjacent to the container flange of the container component.

31. The device according to Embodiment 30, wherein:
the container flange is formed with a proximally-opening o-ring groove radially offset from the base wall; and
an o-ring is seated in the o-ring groove so as to provide a seal between the shoulder of the plug component and the container flange of the container component upon assembly of the plug component within the container component in the second operational mode.

32. The device according to Embodiment 30 or Embodiment 31, wherein the distance from the container flange to the wall top surface of the elongated channel wall installed within the internal cavity of the container component is substantially equivalent to the distance from the shoulder to the distal end of the plug component, whereby assembly of the plug component within the container component in the second operational mode such that the engagement lip of the container component is engaged within the engagement groove of the plug component and the shoulder of the plug component is positioned adjacent to the container flange of the container component causes the plug distal surface of the plug component to substantially seat against the wall top surface of the elongated channel wall of the container component to substantially close the top of the elongated mixing channel and further causes a plug seating portion of the plug component to seat within a container seating portion of the container component to substantially seal the elongated mixing channel other than the input end in fluid communication with the plug outlet port.

33. The device according to any of Embodiments 22-32, wherein at least one container vent hole is formed within the container flange radially outwardly of the base wall, whereby in the first operational mode with the plug component partially inserted within the container component there is fluid communication between the inner cavity of the container component and the surrounding atmosphere at least through the at least one container vent hole.

34. The device according to Embodiment 31, wherein at least one container vent hole is formed within the container flange radially outwardly of the o-ring groove, whereby in the first operational mode with the plug component partially inserted within the container component there is fluid communication between the internal cavity of the container component and the surrounding atmosphere at least through the at least one container vent hole, and further whereby in the second operational mode with the plug component fully assembled within the container component, the o-ring seated in the o-ring groove seals between the shoulder of the plug component and the container flange of the container component so as to prevent fluid communication between the internal cavity and the surrounding atmosphere.

35. The device according to any of Embodiments 22-32, wherein at least one plug vent hole is formed within the distal end of the plug component radially outwardly of the base wall of the container component, whereby in the first operational mode with the plug component partially inserted within the container component there is fluid communication between the inner cavity of the container component and the surrounding atmosphere at least through the at least one plug vent hole.

36. The device according to Embodiment 31, wherein at least one plug vent hole is formed within the distal end of the plug component radially outwardly of the o-ring groove formed in the container flange of the container component, whereby in the first operational mode with the plug component partially inserted within the container component there is fluid communication between the internal cavity of the container component and the surrounding atmosphere at least through the at least one plug vent hole, and further whereby in the second operational mode with the plug component fully assembled within the container component, the o-ring seated in the o-ring groove seals between the shoulder of the plug component and the container flange of the container component so as to prevent fluid communication between the internal cavity and the surrounding atmosphere.

37. The device according to any of Embodiments 33-36, wherein in the first operational mode with the plug component partially inserted within the container component a radially-outwardly projecting retention lip formed on the outer surface of the side wall of the plug component seats on a radially-inwardly projecting engagement lip formed proximally on the engagement wall of the container component, whereby the shoulder of the plug component is suspended above the container flange of the container component and the plug seating portion of the plug component is at least partially suspended within the distribution groove formed as an upwardly-opening step in the inner surface of the base wall of the container component so as to facilitate the fluid communication between the internal cavity of the container component, and particularly the elongated mixing channel, and the surrounding atmosphere through at least one of the at least one container vent hole and the at least one plug vent hole.

38. The device according to Embodiment 37, wherein the radially-inwardly projecting engagement lip is flexible and shifting the device to the second operational mode with the plug component fully assembled within the container component involves shifting the radially-inwardly projecting engagement lip proximally relative to the radially-outwardly projecting retention lip so as to pass thereover and seat proximally thereof and adjacent thereto.

39. The device according to any of Embodiments 24-38, wherein the radially-inwardly projecting engagement lip is formed on a flexible leg defining a portion of the engagement wall of the container component.
40. The device according to Embodiment 39, wherein the engagement wall comprises two substantially offset flexible legs.
41. The device according to Embodiment 40, comprising two container vent holes.
42. The device according to Embodiment 40, comprising multiple plug vent holes.
43. The device according to Embodiment 40, comprising two, three, or four plug vent holes.
44. The device according to Embodiment 39, wherein the engagement wall comprises three spaced apart flexible legs.
45. The device according to Embodiment 44, comprising three container vent holes.
46. The device according to Embodiment 44, comprising multiple plug vent holes.
47. The device according to Embodiment 44, comprising two, three, or four plug vent holes.
48. The device according to Embodiment 39, wherein the engagement wall comprises four spaced apart flexible legs.
49. The device according to Embodiment 48, comprising four container vent holes.
50. The device according to Embodiment 48, comprising multiple plug vent holes.
51. The device according to Embodiment 48, comprising two, three, or four plug vent holes.
52. The device according to any of Embodiments 37-51, wherein the flexible leg is defined by a section of the engagement wall bounded by offset lengthwise notches so as to function as a living hinge.
53. The device according to any of Embodiments 37-52, wherein the position of the flexible leg as extending from the radially-outwardly extending container flange substantially corresponds to the position of the at least one container vent hole.
54. The device according to any of Embodiments 28-38, wherein the radially-outwardly projecting retention lip is formed on a flexible leg defining a portion of the side wall of the plug component.
55. The device according to Embodiment 54, wherein the side wall comprises two substantially offset flexible legs.
56. The device according to Embodiment 54, wherein the side wall comprises three spaced apart flexible legs.
57. The device according to Embodiment 54, wherein the side wall comprises four spaced apart flexible legs.
58. The device according to any of Embodiments 54-57, wherein the flexible leg is defined by a section of the side wall bounded by offset lengthwise notches.
59. The device according to Embodiment 58, wherein the flexible leg is attached to the side wall only at a lower leg joint along a single edge so as to function as a living hinge.
60. The device according to any of Embodiments 22-59, wherein the side wall of the plug component terminates proximally in a radially-outwardly extending plug flange.
61. The device according to Embodiment 60, wherein the plug flange defines a plug perimeter that is substantially radially coterminous with the engagement wall of the container component.
62. The device according to any of Embodiments 22-59, wherein the container flange extends radially-outwardly beyond the proximally extending engagement wall.
63. The device according to Embodiment 62, wherein a perimeter wall extends substantially proximally from the container flange radially outwardly of and spaced from the engagement wall.
64. The device according to Embodiment 63, wherein the perimeter wall and the engagement wall are substantially coterminous proximally.
65. The device according to Embodiment 63 or Embodiment 64, wherein the side wall of the plug component terminates proximally in a radially-outwardly extending plug flange defining a plug perimeter that is substantially radially coterminous with the perimeter wall of the container component.
66. The device according to any of Embodiments 1-21, wherein the base wall terminates proximally in a proximally extending engagement wall.
67. The device according to Embodiment 66, wherein the base wall and the engagement wall are substantially contiguous.
68. The device according to Embodiment 66 or Embodiment 67, wherein the engagement wall is substantially annular.
69. The device according to any of Embodiments 66-68, wherein the engagement wall terminates proximally in a radially-inwardly projecting engagement lip.
70. The device according to Embodiment 69, wherein the engagement lip is configured to engage the proximal end of the plug component.
71. The device according to Embodiment 70, wherein the proximal end of the plug component is formed having a proximally-facing plug proximal surface, and wherein the engagement lip is formed having a distally-facing lip distal surface configured to seat against the plug proximal surface when the plug component is fully seated within the container component in the second operational mode of the device.
72. The device according to any of Embodiments 69-71, wherein the engagement lip is substantially continuous.
73. The device according to any of Embodiments 69-72, wherein a radially-outwardly opening retention groove is formed on the outer surface of the side wall of the plug component and configured for engagement with the radially-inwardly projecting engagement lip of the container component in the first operational mode of the device and further configured for engagement with a radially-inwardly-projecting retention lip formed in the engagement wall of the container component distal of the engagement lip in the second operational mode of the device.
74. The device according to any of Embodiments 69-72, wherein a radially-outwardly projecting retention lip is formed on the outer surface of the side wall of the plug component and configured for engagement with the radially-inwardly projecting engagement lip of the container component in the first operational mode of the device and further configured for engagement with a radially-inwardly opening engagement groove of the container component in the second operational mode of the device.
75. The device according to any of Embodiments 66-74, wherein:
a radially-inwardly opening retention groove is formed on the inner surface of the base wall of the container component; and
a radially-outwardly extending retention lip is formed on the outer surface of the side wall of the plug component and configured for engagement with the radially-inwardly opening retention groove of the container component in the second operational mode of the device.

76. The device according to Embodiment 75, wherein both the retention groove and the retention lip are positioned proximal of the distribution groove.
77. The device according to any of Embodiments 66-76, wherein:
   a radially-outwardly opening o-ring groove is formed on the outer surface of the side wall of the plug component; and
   an o-ring is seated in the o-ring groove for sealing between the plug outer surface and the container inner surface.
78. The device according to any of Embodiments 66-77, wherein a radially-inwardly extending retention lip is formed on the inner surface of the base wall of the container component and configured for engagement with the radially-outwardly opening retention groove formed on the outer surface of the side wall of the plug component in the second operational mode of the device.
79. The device according to any of Embodiments 66-78, wherein:
   the plug component is formed having a stepped side wall defined by a distally-facing plug shoulder separating a relatively larger diameter proximal plug engagement portion from a relatively smaller diameter distal plug seating portion;
   the container component is formed having a stepped base wall defined by a proximally-facing container shoulder separating a relatively larger diameter proximal container engagement portion from a relatively smaller diameter distal container seating portion, the container engagement portion being configured for selective engagement with the plug engagement portion, and the container seating portion being configured for selective receipt of the plug seating portion.
80. The device according to Embodiment 79, wherein the distance from the engagement lip to the container shoulder is substantially equivalent to the distance from the engagement groove to the plug shoulder, whereby engagement of the engagement lip within the engagement groove upon assembly of the plug component within the container component in the second operational mode substantially positions the plug shoulder adjacent to the container shoulder.
81. The device according to Embodiment 79, wherein the distance from the lip distal surface to the container shoulder is substantially equivalent to the distance from the plug proximal surface to the plug shoulder, whereby engagement of the engagement lip with the plug proximal end upon assembly of the plug component within the container component in the second operational mode substantially positions the plug shoulder adjacent to the container shoulder.
82. The device according to Embodiment 80 or Embodiment 81, wherein:
   the container shoulder is formed with a proximally-opening o-ring groove radially offset from the base wall; and
   an o-ring is seated in the o-ring groove so as to provide a seal between the plug shoulder and the container shoulder upon assembly of the plug component within the container component in the second operational mode.
83. The device according to any of Embodiments 79-82, wherein the plug shoulder is formed on the side wall proximal of the distribution groove.
84. The device according to any of Embodiments 79-83, wherein the container shoulder is formed on the base wall proximal of the distribution groove.
85. The device according to any of Embodiments 79-84, wherein the container shoulder is formed on the base wall proximal of the retention groove.
86. The device according to any of Embodiments 79-85, wherein the distance from the container shoulder to the wall top surface of the elongated channel wall installed within the internal cavity of the container component is substantially equivalent to the distance from the plug shoulder to the distal end of the plug component, whereby assembly of the plug component within the container component in the second operational mode such that the engagement lip of the container component is engaged within the engagement groove of the plug component and the shoulder of the plug component is positioned adjacent to the container flange of the container component causes the plug distal surface of the plug component to substantially seat against the wall top surface of the elongated channel wall of the container component to substantially close the top of the elongated mixing channel and further causes a plug seating portion of the plug component to seat within a container seating portion of the container component to substantially seal the elongated mixing chamber other than the input end in fluid communication with the plug outlet port.
87. The device according to any of Embodiments 79-86, wherein in the first operational mode with the plug component partially inserted within the container component the radially-inwardly projecting engagement lip formed proximally on the engagement wall of the container component seats within the radially-outwardly opening retention groove formed on the outer surface of the side wall of the plug component, whereby the plug shoulder is suspended above the container shoulder and the plug seating portion of the plug component is at least partially suspended within the container seating portion so as to facilitate the fluid communication between the internal cavity of the container component, and particularly the elongated mixing channel, and the surrounding atmosphere substantially about the plug component.
88. The device according to any of Embodiments 73-86, wherein in the first operational mode with the plug component partially inserted within the container component the radially-inwardly projecting engagement lip formed proximally on the engagement wall of the container component seats within the radially-outwardly opening retention groove formed on the outer surface of the side wall of the plug component, whereby a plug seating portion of the plug component is at least partially suspended within a container seating portion of the container component so as to facilitate the fluid communication between the internal cavity of the container component, and particularly the elongated mixing channel, and the surrounding atmosphere substantially about the plug component.
89. The device according to any of Embodiments 74-86, wherein in the first operational mode with the plug component partially inserted within the container component the radially-inwardly projecting engagement lip formed proximally on the engagement wall of the container component seats on the radially-outwardly projecting retention lip formed on the outer surface of the side wall of the plug component, whereby a plug seating portion of the plug component is at least partially suspended within a container seating portion of the container component so as to facilitate the fluid communication between the internal cavity of the container component, and particularly the elongated mixing channel, and the surrounding atmosphere substantially about the plug component.
90. The device according to any of Embodiments 73-89, wherein at least one container vent hole is formed within the container engagement wall proximal of the retention lip, whereby in the first operational mode with the plug component partially inserted within the container component there is fluid communication between the inner cavity of the container component and the surrounding atmosphere at least through the at least one container vent hole.
91. The device according to any of Embodiments 88-90, wherein the radially-inwardly projecting engagement lip is flexible and shifting the device to the second operational mode with the plug component fully assembled within the container component involves shifting the radially-inwardly projecting engagement lip proximally relative to the radially-outwardly opening retention groove so as to pass thereover and seat proximally thereof.
92. The device according to any of Embodiments 69-91, wherein the radially-inwardly projecting engagement lip is formed on a flexible leg defining a portion of the engagement wall of the container component.
93. The device according to Embodiment 92, wherein the engagement wall comprises two substantially offset flexible legs.
94. The device according to Embodiment 93, comprising two container vent holes.
95. The device according to Embodiment 92, wherein the engagement wall comprises three spaced apart flexible legs.
96. The device according to Embodiment 95, comprising three container vent holes.
97. The device according to Embodiment 92, wherein the engagement wall comprises four spaced apart flexible legs.
98. The device according to Embodiment 97, comprising four container vent holes.
99. The device according to any of Embodiments 92-98, wherein the flexible leg is defined by a section of the engagement wall bounded by offset lengthwise notches so as to function as a living hinge.
100. The device according to any of Embodiments 92-102, wherein the position of the flexible leg as extending from the radially-outwardly extending container flange substantially corresponds to the position of the at least one container vent hole.
101. The device according to any of Embodiments 73-100, wherein the radially-outwardly projecting retention lip is formed on a flexible leg defining a portion of the side wall of the plug component.
102. The device according to Embodiment 101, wherein the side wall comprises two substantially offset flexible legs.
103. The device according to Embodiment 101, wherein the side wall comprises three spaced apart flexible legs.
104. The device according to Embodiment 101, wherein the side wall comprises four spaced apart flexible legs.
105. The device according to any of Embodiments 101-104, wherein the flexible leg is defined by a section of the side wall bounded by offset lengthwise notches.
106. The device according to Embodiment 105, wherein the flexible leg is attached to the side wall only at a lower leg joint along a single edge so as to function as a living hinge.
107. The device according to any of Embodiments 66-106, wherein the side wall of the plug component terminates proximally in a radially-outwardly extending plug flange.
108. The device according to Embodiment 107, wherein the plug flange defines a plug perimeter that is substantially radially coterminous with the engagement wall of the container component.
109. The device according to any of Embodiments 66-109, wherein:
the container component is formed with a container indexing surface; and
the plug component is formed with a plug indexing surface configured to selectively engage the container indexing surface as the plug component is seated within the container component, whereby in the second operational mode the plug outlet port is positioned substantially adjacent to the input end of the mixing channel.
110. The device according to Embodiment 109, wherein the container indexing surface and the plug indexing surface are substantially helical.
111. The device according to Embodiment 109, wherein the container indexing surface and the plug indexing surface are substantially opposed inclined surfaces.
112. The device according to Embodiment 109, wherein the container indexing surface and the plug indexing surface are substantially threaded.
113. The device according to any of Embodiments 109-112, wherein:
the container indexing surface is substantially proximally-facing; and
the plug indexing surface is substantially distally-facing.
114. The device according to any of Embodiments 109-113, wherein the plug outlet port is positioned substantially adjacent the distal-most portion of the plug indexing surface.
115. The device according to any of Embodiments 109-113, wherein the plug outlet port is positioned substantially at the interface of the plug side wall outer surface and the plug distal surface.
116. The device according to any of Embodiments 1-115, wherein the flow path comprises a substantially axial bore formed in the inlet connector port intersected by and in fluid communication with a substantially transverse bore defining the plug outlet port.
117. The device according to any of Embodiments 1-116, wherein a container outlet cap is configured for selective sealable engagement with the external ejection connector port.
118. The device according to Embodiment 117, wherein the container outlet cap has an outlet cap wall that is substantially coterminous with the container base wall.
119. The device according to Embodiment 117, wherein the container outlet cap has an outlet cap wall having an outlet cap diameter that is at least as large as the container base wall diameter.
120. The device according to Embodiment 117, wherein the container outlet cap has an outlet cap wall terminating distally in an outlet cap base defining an outlet cap base surface.
121. The device according to any of Embodiments 117-120, wherein the outlet cap base surface is substantially planar, whereby the device is capable of standing vertically on the container outlet cap.
122. The device according to any of Embodiments 118-121, wherein the outlet cap wall defines an outlet cap perimeter that is sufficient to permit the device to stand vertically on the container outlet cap.

123. The device according to Embodiment 122, wherein:
the outlet cap perimeter has an outlet cap cross-sectional area; and
the container base wall defines a container perimeter having a container cross-sectional area.
124. The device according to Embodiment 123, wherein the outlet cap cross-sectional area is at least 50% of the container cross-sectional area.
125. The device according to Embodiment 123, wherein the outlet cap cross-sectional area is at least 60% of the container cross-sectional area.
126. The device according to Embodiment 123, wherein the outlet cap cross-sectional area is at least 70% of the container cross-sectional area.
127. The device according to Embodiment 123, wherein the outlet cap cross-sectional area is at least 80% of the container cross-sectional area.
128. The device according to Embodiment 123, wherein the outlet cap cross-sectional area is at least 90% of the container cross-sectional area.
129. The device according to Embodiment 123, wherein the outlet cap cross-sectional area is at least 95% of the container cross-sectional area.
130. The device according to Embodiment 123, wherein the outlet cap cross-sectional area is at least 100% of the container cross-sectional area.
131. The device according to any of Embodiments 117-130, wherein the outlet cap and the external ejection connector port are configured having mating luer connection members.
132. The device according to any of Embodiments 117-131, wherein removal of the outlet cap allows for engagement of the external ejection connector port with a cannula.
133. The device according to Embodiment 132, wherein the engagement of the cannula with the external ejection connector port is by way of mating luer connection members.
134. The device according to any of Embodiments 1-133, wherein a plug inlet cap is configured for selective sealable engagement with the external inlet connector port.
135. The device according to Embodiment 134, wherein the inlet cap and the external inlet connector port are configured having mating luer connection members.
136. The device according to Embodiment 134 or Embodiment 135, wherein removal of the inlet cap allows for engagement of the external inlet connector port with a syringe.
137. The device according to Embodiment 136, wherein the engagement of the syringe with the external inlet connector port is by way of mating luer connection members.
138. The device according to any of Embodiments 1-116, wherein the predetermined quantity of the first constituent is nominally two tenths of a cubic centimeter (0.2 cc).
139. The device according to any of Embodiments 1-116, wherein the predetermined quantity of the first constituent is nominally one cubic centimeter (1.0 cc).
140. The device according to Embodiment 138 or Embodiment 139, wherein the internal cavity volume accounting for the elongated channel wall is substantially equivalent to the predetermined quantity of the first constituent.
141. The device according to any of Embodiments 1-140, wherein a supplied volume of the second constituent is substantially equal to the predetermined quantity of the first constituent.
142. The device according to any of Embodiments 1-140, wherein a supplied volume of the second constituent is greater than the predetermined quantity of the first constituent.
143. The device according to any of Embodiments 1-140, wherein a supplied volume of the second constituent is substantially double the predetermined quantity of the first constituent.
144. The device according to any of Embodiments 1-143, wherein:
the external inlet connector port is configured as a female luer connector; and
the external ejection connector port is configured as a male luer connector.
145. The device according to Embodiment 144, wherein the male luer connector and the female luer connector are sized so as to be selectively engageable.
146. The device according to any of Embodiments 1-116, wherein a reservoir is formed integrally with the plug component so as to be in selective fluid communication with the external inlet connector port.
147. The device according to Embodiment 146, wherein the reservoir contains the second constituent.
148. The device according to Embodiment 147, wherein the reservoir is configured as a syringe.
149. The device according to Embodiment 147 or Embodiment 148, further comprising a plunger operable within the reservoir.
150. The device according to any of Embodiments 146-149, wherein the reservoir volume is substantially equal to the predetermined quantity of the first constituent.
151. The device according to any of Embodiments 146-149, wherein the reservoir volume is greater than the predetermined quantity of the first constituent.
152. The device according to any of Embodiments 146-149, wherein the reservoir volume is substantially double the predetermined quantity of the first constituent.
153. The device according to any of Embodiments 1-116, wherein a cannula is formed integrally with the container component so as to be in fluid communication with the external outlet connector port.
154. The device according to Embodiment 153, wherein a container outlet cap is configured for selective sealable engagement with the external ejection connector port substantially about the cannula.
155. The device according to any of Embodiments 1-154, wherein:
the first constituent is substantially in powder form; and
the second constituent is substantially in liquid form.
156. The device according to Embodiment 155, wherein:
the first constituent is a lyophilized medicine; and
the second constituent is a diluent.
157. The device according to Embodiment 156, wherein the first constituent is introduced into the internal cavity of the container component substantially in liquid form initially, whereafter the device in the first operational mode is subjected to a lyophilization process to yield the lyophilized medicine.
158. The device according to Embodiment 156 or Embodiment 157, wherein the diluent is housed initially in a syringe, whereafter the syringe is connected to the external inlet connector port of the plug component and the diluent forced through the plug component and into the internal cavity so as to contact the lyophilized medicine, reconstituting the powder to form a delivery solution having a medication concentration gradient as it flows out the external ejection connector port with initial flow of delivery solution having a higher concentration of the medication than later flow of the delivery solution, whereby mixing and delivery occur in the same step and a separate reconstitution step is not necessary.

159. The device according to Embodiment 155, wherein:
the first constituent is an active lyophilized powder; and
the second constituent is an active diluent.

160. The device according to Embodiment 159, wherein the first constituent is introduced into the internal cavity of the container component substantially in liquid form initially, whereafter the device in the first operational mode is subjected to a lyophilization process to yield the lyophilized powder.

161. The device according to Embodiment 159 or Embodiment 160, wherein the diluent is housed initially in a syringe, whereafter the syringe is connected to the external inlet connector port of the plug component and the diluent forced through the plug component and into the internal cavity so as to contact the lyophilized powder, reconstituting the powder to form a delivery solution having an active ingredient concentration gradient as it flows out the external ejection connector port with initial flow of delivery solution having a higher concentration of the active ingredient than later flow of the delivery solution, whereby mixing and delivery occur in the same step and a separate reconstitution step is not necessary.

162. The device according to Embodiment 155, wherein:
the first constituent is an inactive powder; and
the second constituent is active diluent.

163. The device according to Embodiment 162, wherein the diluent is housed initially in a syringe, whereafter the syringe is connected to the external inlet connector port of the plug component and the diluent forced through the plug component and into the internal cavity so as to contact the powder, activating the powder to form a delivery solution having an active ingredient concentration gradient as it flows out the external ejection connector port with initial flow of delivery solution having a higher concentration of the active ingredient than later flow of the delivery solution, whereby mixing and delivery occur in the same step and a separate activation step is not necessary.

164. The device according to Embodiment 155, wherein:
the first constituent is one of a lyophilized medicine, an active lyophilized powder, and an inactive powder; and
the second constituent is a reconstituted drug.

165. The device according to Embodiment 164, wherein the reconstituted drug is sourced from a device according to Embodiments 156-163.

166. The device according to any of Embodiments 1-154, wherein the first and second constituents are substantially in liquid form.

167. The device according to any of Embodiments 1-166, wherein the first and second constituents are both drugs.

168. The device according to any of Embodiments 1-166, wherein the first and second constituents are a drug and a chemical.

169. The device according to any of Embodiments 1-166, wherein the first and second constituents are both chemicals.

170. The device according to any of Embodiments 1-166, wherein the first and second constituents are a drug and a matrix.

171. The device according to any of Embodiments 1-166, wherein the first and second constituents are a drug and an albumin.

172. The device according to any of Embodiments 1-166, wherein the first and second constituents are a drug and an antibody fragment.

173. The device according to any of Embodiments 1-166, wherein the first and second constituents are a marker and an antibody fragment.

174. The device according to any of Embodiments 1-166, wherein the first and second constituents are a drug and a carrier.

175. The device according to any of Embodiments 1-166, wherein the first and second constituents are a drug and a targeting molecule.

176. The device according to any of Embodiments 1-166, wherein the first and second constituents are a diagnostic and a chemical.

177. The device according to any of Embodiments 1-166, wherein the first and second constituents are selected from the group consisting of a drug, a chemical, a matrix, an albumin, an antibody fragment, a marker, a carrier, a targeting molecule, a diagnostic, and a diluent or any combination thereof.

178. The device according to Embodiment 177, wherein the chemical extends the half-life of the delivery solution.

179. The device according to any of Embodiments 1-178, wherein pre-mixing of the first and second constituents is undesirable.

180. The device according to Embodiment 179, wherein pre-mixing of the first and second constituents forms a delivery solution having an unstable pH.

181. The device according to Embodiment 179, wherein pre-mixing of the first and second constituents forms a delivery solution having an undesirable pH.

182. The device according to Embodiment 179, wherein pre-mixing of the first and second constituents forms a delivery solution having unstable storage beyond a particular shelf-life.

183. The device according to Embodiment 179, wherein pre-mixing of the first and second constituents forms a delivery solution having undesirable storage beyond a particular shelf-life.

184. The device according to Embodiment 182 or Embodiment 183, wherein the shelf-life is five minutes.

185. The device according to Embodiment 182 or Embodiment 183, wherein the shelf-life is thirty minutes.

186. The device according to Embodiment 182 or Embodiment 183, wherein the shelf-life is one hour.

187. The device according to Embodiment 182 or Embodiment 183, wherein the shelf-life is one day.

188. The device according to Embodiment 179, wherein pre-mixing of the first and second constituents forms a delivery solution having unstable formulation attributes.

189. The device according to Embodiment 179, wherein pre-mixing of the first and second constituents forms a delivery solution having undesirable formulation attributes.

190. The device according to Embodiment 179, wherein pre-mixing of the first and second constituents causes increased aggregation.

191. The device according to Embodiment 179, wherein pre-mixing of the first and second constituents causes increased crystallization.

192. The device according to Embodiment 179, wherein pre-mixing of the first and second constituents is 193. The device according to Embodiment 179, wherein pre-mixing of the first and second constituents is unsupported by regulatory authorities.

194. The device according to Embodiment 179, wherein pre-mixing of the first and second constituents causes an unwanted chemical reaction.

195. The device according to Embodiment 179, wherein pre-mixing of the first and second constituents causes a premature chemical reaction.

196. A method of employing a solution delivery device as defined in any one of Embodiments 1-195, the method comprising the steps of:
a) filling the predetermined quantity of the first constituent within the internal cavity of the container component;
b) positioning the plug component in the container component in the first operational mode of the device wherein the plug distal surface is spaced from the first constituent;
c) acting on the first constituent with the device in the first operational mode;
d) shifting the plug component to the second operational mode of the device wherein the plug component is fully seated within the container component and the plug distal surface is substantially adjacent to the first constituent; and
e) flowing the second constituent through an internal flow path formed within the plug component and into the internal cavity of the container component so as to contact the first constituent;
whereby the first and second constituents are sufficiently mixed in forming the delivery solution without the need for a separate mixing, shaking, reconstituting, or priming step.

197. The method according to Embodiment 196, wherein the step of filling the predetermined quantity of the first constituent is accomplished through a vial-fill assembly line process.

198. The method according to Embodiment 196 or Embodiment 197, comprising the further step of removably installing a container outlet cap on the external ejection connector port, the container outlet cap serving to stand the container component substantially upright during the filling step.

199. The method according to Embodiment 196, wherein the step of positioning the plug component in the container component in the first operational mode allows for a vent gap whereby the internal cavity of the container component is in fluid communication with the surrounding atmosphere.

200. The method according to any of Embodiments 196-199, wherein the step of acting on the first constituent with the device in the first operational mode comprises subjecting the device to a lyophilization process.

201. The method according to any of Embodiments 196-199, wherein the step of acting on the first constituent with the device in the first operational mode comprises subjecting the device to a spray-drying process.

202. The method according to any of Embodiments 196-199, wherein the step of acting on the first constituent with the device in the first operational mode comprises subjecting the device to a spray-freeze drying process.

203. The method according to any of Embodiments 196-199, wherein the step of acting on the first constituent with the device in the first operational mode comprises subjecting the device to a bulk crystallization process.

204. The method according to any of Embodiments 196-199, wherein the step of acting on the first constituent with the device in the first operational mode comprises subjecting the device to a vacuum drying process.

205. The method according to any of Embodiments 196-199, wherein the step of acting on the first constituent with the device in the first operational mode comprises subjecting the device to a foam drying process.

206. The method according to any of Embodiments 196-205, wherein the step of shifting the plug component to the second operational mode comprises abutting the plug distal surface on the wall top surface of the elongated channel wall installed within the internal cavity of the container component.

207. The method according to any of Embodiments 196-206, wherein the step of shifting the plug component to the second operational mode comprises snapping the plug component within the container component.

208. The method according to any of Embodiments 196-206, wherein the step of shifting the plug component to the second operational mode comprises welding the plug component within the container component.

209. The method according to any of Embodiments 196-206, wherein the step of shifting the plug component to the second operational mode comprises bonding the plug component within the container component.

210. The method according to any of Embodiments 207-209, further comprising tamper-proofing the device.

211. The method according to Embodiment 210, wherein the step of tamper-proofing the device comprises positioning the engagement surfaces internally.

212. The method according to Embodiment 210, wherein the step of tamper-proofing the device comprises positioning a perimeter wall about the engagement wall of the container component wherein are located the engagement surfaces.

213. The method according to any of Embodiments 196-212, wherein the step of flowing the second constituent comprises connecting a syringe containing the second constituent to the external inlet connector port of the plug component and activating a plunger of the syringe to force the second constituent through the internal flow path and into the inner cavity of the container component.

214. The method according to any of Embodiments 196-212, wherein the step of flowing the second constituent comprises activating a plunger operably positioned within a reservoir formed integrally with the plug component so as to be in selective fluid communication with the external inlet connector port.

215. The method according to Embodiment 213 or Embodiment 214, wherein the step of flowing the second constituent further comprises activating an injector wherein the device is operably installed.

216. The method according to Embodiment 215, wherein the step of activating the injector comprises applying force proximally to a distal end of the injector.

217. The method according to Embodiment 216, wherein the step of applying force to the injector distal end operates to shift the plunger distally under the bias of a plunger spring.

218. The method according to Embodiment 217, wherein the spring force of the plunger spring as compressed when the injector is activated is sufficient to overcome a membrane temporarily sealing the external inlet connector port and to thereby allow the flow of the second constituent into the plug component.

219. The method according to Embodiment 218, wherein the membrane is overcome by pressure so as to rupture the membrane.

220. The method according to any of Embodiments 217-219, wherein the membrane is overcome by a piercing tip affixed to the plunger and shifted into contact with the membrane under the bias of the plunger spring acting on the plunger.

221. The method according to any of Embodiments 196-212, wherein the step of flowing the second constituent comprises connecting a second solution delivery device in series upstream of a first solution delivery device and directing the second constituent defined by the delivery solution of the second solution delivery device from the second solution delivery device into the external inlet connector port of the first solution delivery device.

222. The method according to Embodiment 221, further comprising the step of connecting a syringe containing a fourth constituent to the external inlet connector port of the plug component of the second device and activating a plunger of the syringe to force the fourth constituent through the internal flow path and into the inner cavity of the container component of the second device so as to mix with a third constituent contained therein and thereby form the second device delivery solution defining the second constituent.

223. The method according to Embodiment 222, wherein:
the first constituent is one of a lyophilized medicine, an active lyophilized powder, and an inactive powder; and
the second constituent is a diluent.

224. The method according to Embodiment 222, wherein the third and fourth constituents are selected from the group consisting of a drug, a chemical, a matrix, an albumin, an antibody fragment, a marker, a carrier, a targeting molecule, a diagnostic, and a diluent or any combination thereof.

225. The method according to any of Embodiments 196-224, wherein pre-mixing of the first and second constituents is undesirable.

226. The method according to Embodiment 225, wherein pre-mixing of the first and second constituents forms a delivery solution having an unstable pH.

227. The method according to Embodiment 225, wherein pre-mixing of the first and second constituents forms a delivery solution having an undesirable pH.

228. The method according to Embodiment 225, wherein pre-mixing of the first and second constituents forms a delivery solution having unstable storage beyond a particular shelf-life.

229. The method according to Embodiment 225, wherein pre-mixing of the first and second constituents forms a delivery solution having undesirable storage beyond a particular shelf-life.

230. The method according to Embodiment 228 or Embodiment 229, wherein the shelf-life is five minutes.

231. The method according to Embodiment 228 or Embodiment 229, wherein the shelf-life is thirty minutes.

232. The method according to Embodiment 228 or Embodiment 229, wherein the shelf-life is one hour.

233. The method according to Embodiment 228 or Embodiment 229, wherein the shelf-life is one day.

234. The method according to Embodiment 225, wherein pre-mixing of the first and second constituents forms a delivery solution having unstable formulation attributes.

235. The method according to Embodiment 225, wherein pre-mixing of the first and second constituents forms a delivery solution having undesirable formulation attributes.

236. The method according to Embodiment 225, wherein pre-mixing of the first and second constituents causes increased aggregation.

237. The method according to Embodiment 225, wherein pre-mixing of the first and second constituents causes increased crystallization.

238. The method according to Embodiment 225, wherein pre-mixing of the first and second constituents is unstable at room temperature.

239. The method according to Embodiment 225, wherein pre-mixing of the first and second constituents is unsupported by regulatory authorities.

240. The method according to Embodiment 225, wherein pre-mixing of the first and second constituents causes an unwanted chemical reaction.

241. The method according to Embodiment 225, wherein pre-mixing of the first and second constituents causes a premature chemical reaction.

242. The method according to any of Embodiments 196-241, wherein the step of filling the predetermined quantity of the first constituent within the internal cavity of the container component occurs prior to the step of positioning the plug component in the container component in the first operational mode.

243. The method according to any of Embodiments 196-242, wherein a further step of removably installing a container outlet cap on the external ejection connector port occurs prior to the step of filling the predetermined quantity of the first constituent within the internal cavity of the container component, the container outlet cap serving to stand the container component substantially upright during the filling step and to temporarily seal the external ejection connector port.

244. The method according to Embodiment 243, wherein the container outlet cap remains engaged with the external ejection connector port during the step of acting on the first constituent with the device in the first operational mode, the container outlet cap serving to stand the device substantially upright during the acting step.

245. The method according to Embodiment 243 or Embodiment 244, wherein the container outlet cap remains engaged with the external ejection connector port during the step of shifting the plug component to the second operational mode of the device, the container outlet cap serving to stand the device substantially upright during the shifting step.

246. The method according to any of Embodiments 243-245, further comprising the step of removing the container outlet cap prior to the step of flowing the second constituent.

247. The method according to any of Embodiments 196-242, wherein a further step of removably installing a plug inlet cap on the external inlet connector port of the plug component occurs prior to the step of positioning the plug component in the container component in the first operational mode.

248. The method according to any of Embodiments 196-242, wherein a further step of removably installing a plug inlet cap on the external inlet connector port of the plug component occurs after the step of positioning the plug component in the container component in the first operational mode.

249. The method according to any of Embodiments 196-242, wherein a further step of removably installing a plug inlet cap on the external inlet connector port of the plug component occurs after the step of acting on the first constituent with the device in the first operational mode.

250. The method according to any of Embodiments 196-242, wherein a further step of removably installing a plug inlet cap on the external inlet connector port of the plug component occurs after the step of shifting the plug component to the second operational mode of the device.
251. The method according to any of Embodiments 247-250, further comprising the step of removing the plug inlet cap prior to the step of flowing the second constituent.
252. The method according to any of Embodiments 196-242, further comprising the step of engaging a cannula with the external ejection connector port prior to the step of flowing the second constituent.
253. The method according to Embodiment 252, further comprising the step of subcutaneous insertion of the cannula prior to the step of flowing the second constituent.
254. The method according to any of Embodiments 196-242, further comprising the step of connecting an I.V. line to the external ejection connector port prior to the step of flowing the second constituent.
255. A kit comprising a solution delivery device as defined in any of Embodiments 1-195.
256. The kit according to Embodiment 255, further comprising a container outlet cap removably installed on the external ejection connector port of the container component.
257. The kit according to Embodiment 255 or Embodiment 256, further comprising a plug inlet cap removably installed on the external inlet connector port of the plug component.
258. The kit according to any of Embodiments 255-257, further comprising a cannula.
259. The kit according to Embodiment 258, wherein the cannula is removably installed on the external ejection connector port of the container component.
260. The kit according to Embodiment 258, wherein the cannula is formed integrally with the external ejection connector port of the container component.
261. The kit according to Embodiment 259 or Embodiment 260, wherein a container outlet cap is removably installed on the external ejection connector port of the container component substantially about the cannula.
262. The kit according to any of Embodiments 255-261, further comprising a reservoir.
263. The kit according to Embodiment 262, wherein the reservoir is formed integrally with the plug component.
264. The kit according to Embodiment 262, wherein the reservoir is defined by a syringe.
265. The kit according to any of Embodiments 255-264, further comprising an injector.
266. The kit according to any of Embodiments 255-265, further comprising an I.V. line.
267. The kit according to any of Embodiments 255-266, further comprising instructional material.
268. The kit according to Embodiment 267, wherein the instructional material provides instructions on how to perform a method as defined in any one of Embodiments 196-254.
269. A solution delivery device according to any of Embodiments 1-195 in combination with an injector.
270. The combination according to Embodiment 269, wherein the device is slidably installed within a housing of the injector.
271. The combination according to Embodiment 269 or Embodiment 270, wherein a shielded cannula assembly is installed on the external outlet connector port of the container component of the device, the shielded cannula assembly comprising a cannula.
272. The combination according to any of Embodiments 269-271, further comprising a membrane temporarily sealing the external inlet connector port.
273. The combination according to Embodiment 272, wherein a reservoir is engaged with the external inlet connector port of the plug component, the reservoir containing the second constituent.
274. The combination according to Embodiment 273, wherein the reservoir is formed integrally with the plug component.
275. The combination according to Embodiment 273, wherein the reservoir is defined by a syringe.
276. The combination according to any of Embodiments 273-275, wherein a membrane is positioned substantially between the reservoir and the plug component so as to temporarily seal the external inlet connector port.
277. The combination according to Embodiment 276, wherein a plunger is operable within the reservoir to act on the second constituent.
278. The combination according to Embodiment 277, wherein the plunger is biased distally by a plunger spring.
279. The combination according to Embodiment 278, wherein the plunger spring is fixed axially between the plunger and a proximal housing cap engaged with the housing.
280. The combination according to any of Embodiments 273-279, wherein the device, the reservoir, the membrane, and the shielded cannula assembly together comprise an injector sub-assembly.
281. The combination according to Embodiment 280, wherein the injector sub-assembly is slidably installed within the housing.
282. The combination according to Embodiment 281, wherein the injector sub-assembly is biased distally by an assembly spring anchored against a proximal housing cap engaged with the housing, whereby axial movement of the injector sub-assembly against the assembly spring as when the injector is to be activated by pushing proximally on the shielded cannula assembly compresses the plunger spring and shifts the plunger distally relative to the injector sub-assembly and particularly the reservoir.
283. The combination according to any of Embodiments 276-282, wherein the membrane is configured to fail upon proximal movement of the injector sub-assembly and distal movement of the plunger under the increased force of the plunger spring, whereby the second constituent stored in the reservoir is freed and forced to flow out of the reservoir and through the external inlet connector port of the plug component into the container component and there mix with the first constituent housed within the internal cavity of the container component to form the delivery solution then expelled through the cannula.
284. The combination according to Embodiment 283, wherein the membrane is silicone.
285. The combination according to Embodiment 283, wherein the membrane is polyester.
286. The combination according to Embodiment 283, wherein the membrane is foil.
287. The combination according to any of Embodiments 283-286, wherein the membrane is perforated.
288. The combination according to any of Embodiments 283-286, wherein the membrane has a thickness in the range of 1 to 1,000 microns.
289. The combination according to any of Embodiments 283-288, wherein the membrane is overcome by pressure so as to rupture the membrane.

290. The combination according to any of Embodiments 283-289, wherein the membrane is overcome by perforation through a piercing tip affixed to the plunger and shifted into contact with the membrane under the bias of the plunger spring acting on the plunger.
291. The combination according to any of Embodiments 269-290, wherein the assembly of the device within the injector is unitary.
292. The combination according to any of Embodiments 269-291, wherein the assembly of the device within the injector is single use.
293. The combination according to any of Embodiments 269-292, wherein the assembly of the device within the injector is disposable.
294. The combination according to any of Embodiments 269-293, wherein the delivery solution comprises epinephrine.
295. The combination according to any of Embodiments 269-293, wherein the delivery solution comprises antihistamine.
296. The combination according to any of Embodiments 269-293, wherein the delivery solution comprises antitoxin.
297. The combination according to any of Embodiments 269-293, wherein the delivery solution comprises antivenom.
298. The combination according to any of Embodiments 269-293, wherein the delivery solution comprises morphine.
299. The combination according to any of Embodiments 269-293, wherein the delivery solution comprises naloxone.
300. The combination according to any of Embodiments 269-293, wherein the delivery solution comprises glucose.
301. The combination according to any of Embodiments 269-293, wherein the delivery solution comprises aspirin.
302. The combination according to any of Embodiments 269-293, wherein the delivery solution comprises adrenaline.
303. Use of a solution delivery device as defined in any of Embodiments 1-195 to deliver a delivery solution without the need for a separate mixing, shaking, reconstituting, or priming step.
304. The use according to Embodiment 303, wherein the use is directed to avoiding unwanted pre-mixing of the first and second constituents prior to forming the delivery solution.
305. The use according to Embodiment 303 or Embodiment 304, wherein the use is directed to mixing and delivery of one or more of a drug, a chemical, a matrix, an albumin, an antibody fragment, a marker, a carrier, a targeting molecule, a diagnostic, and a diluent or any combination thereof.
306. The use according to any of Embodiments 303-305, wherein the use is directed to parenteral administration of one or more of epinephrine, antihistamine, antitoxin, antivenom, morphine, naloxone, glucose, aspirin, and adrenaline.
307. The use according to any of Embodiments 303-306, wherein the use is directed to medical emergency.
308. The use according to any of Embodiments 303-307, wherein the use is directed to humans.
309. The use according to any of Embodiments 303-307, wherein the use is directed to animals.
310. The use according to any of Embodiments 303-311, wherein the use is directed to removal of unwanted substances in one of a constituent, a delivery solution, or a sample by passage through the device to capture the unwanted substances.
311. The use according to Embodiment 310, wherein the unwanted substances are selected from the group consisting of unwanted chemicals, infectious substances, and impurities.
312. The use according to Embodiment 310 or Embodiment 311, wherein the use is analogous to an affinity column.
313. The use according to any of Embodiments 310-312, wherein the device functions as an affinity container.
314. The use according to Embodiment 313, wherein the volume of the affinity container is in the range of 0.1 cc to 20.0 cc.
315. The use according to any of Embodiments 310-314, wherein the removal is accomplished by chemical capture.
316. The use according to any of Embodiments 310-314, wherein the removal is accomplished by chemical alteration.
317. The use according to any of Embodiments 310-314, wherein the removal is accomplished by mechanical means.
318. The use according to any of Embodiments 310-317, wherein the use is further directed to parenteral administration of the delivery solution after the removal of unwanted substances.
319. The use according to any of Embodiments 303-318, wherein the use is further directed to continuous infusion of drugs.
320. The use according to Embodiment 319, wherein the use is further directed to drugs with limited solubility selected as the first constituent contained within the internal cavity of the container component.
321. The use according to Embodiment 319, wherein the use is further directed to drugs with significant side effects having slow dissolving formulations selected as the first constituent contained within the internal cavity of the container component.
322. The use according to Embodiment 320 or Embodiment 321, wherein the second constituent is supplied through an I.V. line connected to the external inlet connector port of the plug component.
323. The use according to any of Embodiments 303-322, wherein the use is further directed to substantially simultaneous delivery of mixed multiple treatments.
324. The use according to Embodiment 323, wherein the use is directed to first and second solution delivery devices connected in series.
325. The use according to Embodiment 323 or Embodiment 324, wherein the use is further directed to administration of a drug in combination with an anesthetic indicated for use in reducing side effects associated with the drug.
326. The use according to Embodiment 325, wherein the side effects are one or more of pain, itching, and neurological symptoms associated with administration of the drug.
327. The use according to Embodiment 323 or Embodiment 324, wherein the use is further directed to administration of a drug in combination with an anti-inflammatory indicated for use in reducing side effects associated with the drug.
328. The use according to Embodiment 327, wherein the side effects are one or more of pain, fever, immune responses, and inflammation associated with administration of the drug.

329. The use according to Embodiment 323 or Embodiment 324, wherein the use is further directed to administration of two drugs in combination having synergistic effects.
330. The use according to Embodiment 329, wherein the drugs are two different pain medications and the synergistic effect is each drug having a different mechanism of action.
331. The use according to Embodiment 329, wherein the drugs have different PK or PD profiles.
332. The use according to any of Embodiments 303-331, wherein the use is further directed to substantially simultaneous administration of fixed dose drug combinations.
333. The use according to any of Embodiments 303-331, wherein the use is further directed to substantially simultaneous administration of weight-based dose drug combinations.
334. The use according to any of Embodiments 303-305, wherein the use is directed to non-injectable medical treatment.
335. The use according to Embodiment 334, wherein the use is directed to topical application.
336. The use according to Embodiment 335, wherein the use is directed to nasal delivery.
337. The use according to Embodiment 336, wherein the use is directed to inhalation.
338. The use according to any of Embodiments 303-337, wherein the use is further directed to treatment of an allergic reaction.
339. The use according to any of Embodiments 303-337, wherein the use is further directed to treatment of exposure to a toxin.
340. The use according to any of Embodiments 303-337, wherein the use is further directed to treatment of exposure to a neurotoxin.
341. The use according to any of Embodiments 303-337, wherein the use is further directed to treatment of a snake bite.
342. The use according to any of Embodiments 303-337, wherein the use is further directed to pain management.
343. The use according to any of Embodiments 303-337, wherein the use is further directed to treatment of opioid overdose.
344. The use according to any of Embodiments 303-337, wherein the use is further directed to treatment of a heart attack.
345. The use according to any of Embodiments 303-305, wherein the use is directed to laboratory diagnostics.
346. The use according to Embodiment 345, wherein the use is directed to small volume lyophilized chemicals employed as reagents.
347. The use according to any of Embodiments 303-305, wherein the use is directed to a manufacturing process.
348. The use according to any of Embodiments 303-347, wherein the use comprises a method as defined in any of Embodiments 196-254.

Aspects of the present specification may be further described as follows:

1. A solution delivery device comprising:
   a container component having a proximally-extending engagement wall and an internal cavity with a size selected to contain a predetermined quantity of a first constituent, wherein the engagement wall terminates proximally in a radially-inwardly projecting engagement lip, the container component further having a distal end with an external ejection connector port;
   a plug component configured for selective engagement with the container component in at least first and second operational modes, the plug component having a proximal end, a distal end, and a side wall having an outer surface disposed between the ends and formed with an outwardly-opening engagement groove, the side wall and distal end together defining a plug periphery, the plug component further having an external inlet connector port substantially at the proximal end and an internal flow path from the inlet connector port to a plug outlet port intersecting the plug periphery, the plug component being formed on the distal end with a plug distal surface; and
   an elongated channel wall installed within the internal cavity of the container component to form an elongated mixing channel, the channel wall having a wall top surface and being located within the container component such that the mixing channel has a substantially closed bottom and an open top adjacent the wall top surface, the mixing channel having an input end in fluid communication with the plug outlet port and an output end in fluid communication with the ejection connector port;
   wherein in the first operational mode the plug component is partially inserted within the container component such that the plug distal surface is spaced from the wall top surface so as to facilitate the fluid communication between the internal cavity of the container component, and particularly the mixing channel, and the surrounding atmosphere;
   wherein the wall top surface of the elongated channel wall is located within the container component facing the plug component so that when the plug component and the container component are fully assembled together in the second operational mode as by the engagement lip of the container component engaging the engagement groove of the plug component, the plug distal surface contacts the wall top surface and substantially closes the top of the elongated mixing channel so that the only access to the first constituent is provided by the input and output ends of the mixing channel; and
   wherein forcing a second constituent through the inlet connector port with the device in the second operational mode causes the second constituent to flow through the internal flow path of the plug component and out the plug outlet port and into the input end of the mixing channel so as to mix with the first constituent, whereby the first and second constituents are sufficiently mixed as together traversing the mixing channel from the inlet end to the outlet end and then out through the ejection connector port as a delivery solution without the need for a separate mixing, shaking, reconstituting, or priming step.

2. The device according to Embodiment 1, wherein the plug component further comprises a radially-outwardly projecting retention lip distal of the engagement groove, wherein in the first operational mode with the plug component partially inserted within the container component the retention lip seats on the engagement lip of the container component, whereby the plug component is suspended within the container component.

3. The device according to Embodiment 2, wherein the engagement groove is formed between a proximal radially-outwardly extending plug flange and the distally offset retention lip.

4. The device according to any of Embodiments 1-3, wherein the container component further comprises a base wall with an inner surface and an interconnecting groove formed in the inner surface of the base wall so as to be in fluid communication with the input end of the mixing channel.
5. The device according to Embodiment 4, wherein the interconnecting groove is substantially lengthwise along the container component base wall and of sufficient length to be in fluid communication with the plug outlet port upon assembly of the plug component within the container component in the second operational mode, whereby the mixing channel provides an indirect flow path between the plug outlet port and the ejection connector port.
6. The device according to any of Embodiments 1-5, wherein the container component further comprises a distribution groove formed in one of the inner surface of the base wall or the outer surface of the side wall so as to be in selective fluid communication with the interconnecting groove.
7. The device according to Embodiment 6, wherein the distribution groove is formed as an upwardly-opening step in the inner surface of the base wall, such that the base wall has a stepped inner bore.
8. The device according to any of Embodiments 1-7, wherein the outer surface of the side wall of the plug component is formed having a plug seating portion configured to seat against a container seating portion of an inner surface of a base wall of the container component distal of the engagement wall upon assembly of the plug component within the container component in the second operational mode.
9. The device according to Embodiment 8, wherein the plug seating portion and the container seating portion are configured for a net-fit engagement.
10. The device according to any of Embodiments 1-9, wherein a base wall of the container component terminates proximally in a substantially radially-outwardly extending container flange having the proximally-extending engagement wall.
11. The device according to any of Embodiments 1-10, wherein:
the plug component is formed having a stepped side wall defined by a distally-facing shoulder separating a relatively larger diameter proximal plug engagement portion from a relatively smaller diameter distal plug seating portion; and
the distance from the engagement lip to the container flange of the container component is substantially equivalent to the distance from the engagement groove to the shoulder of the plug component, whereby engagement of the engagement lip within the engagement groove upon assembly of the plug component within the container component in the second operational mode substantially positions the shoulder of the plug component adjacent to the container flange of the container component.
12. The device according to Embodiment 10 or Embodiment 11, wherein the distance from the container flange to the wall top surface of the elongated channel wall installed within the internal cavity of the container component is substantially equivalent to the distance from the shoulder to the distal end of the plug component, whereby assembly of the plug component within the container component in the second operational mode such that the engagement lip of the container component is engaged within the engagement groove of the plug component and the shoulder of the plug component is positioned adjacent to the container flange of the container component causes the plug distal surface of the plug component to substantially seat against the wall top surface of the elongated channel wall of the container component to substantially close the top of the mixing channel and further causes a plug seating portion of the plug component to seat within a container seating portion of the container component to substantially seal the mixing channel other than the input end in fluid communication with the plug outlet port.
13. The device according to any of Embodiments 10-12, wherein at least one container vent hole is formed within the container flange radially outwardly of the base wall, whereby in the first operational mode with the plug component partially inserted within the container component there is fluid communication between the inner cavity of the container component and the surrounding atmosphere at least through the at least one container vent hole.
14. The device according to any of Embodiments 1-13, wherein the radially-inwardly projecting engagement lip is flexible and shifting the device to the second operational mode with the plug component fully assembled within the container component involves shifting the radially-inwardly projecting engagement lip proximally relative to the radially-outwardly projecting retention lip so as to pass thereover and seat proximally thereof and adjacent thereto.
15. The device according to any of Embodiments 1-14, wherein the radially-inwardly projecting engagement lip is formed on a flexible leg defining a portion of the engagement wall of the container component.
16. The device according to Embodiment 15, wherein the flexible leg is defined by a section of the engagement wall bounded by offset lengthwise notches so as to function as a living hinge.
17. The device according to any of Embodiments 1-16, wherein:
the plug component is formed at the plug distal end with a distally-opening insert receiving cavity in fluid communication with the internal flow path; and
a plug insert is received within the insert receiving cavity, the plug insert formed on a top surface with at least one horizontal groove so as to be in fluid communication with the flow path and on an outer surface with at least one vertical groove intersecting and in fluid communication with the horizontal groove, the vertical groove further intersecting a distally-facing bottom surface of the plug insert, the vertical groove defining the plug outlet port and the lower surface defining the plug distal surface.
18. The device according to any of Embodiments 1-17, wherein:
the container component is formed with a container indexing surface; and
the plug component is formed with a plug indexing surface configured to selectively engage the container indexing surface as the plug component is seated within the container component, whereby in the second operational mode the plug outlet port is positioned substantially adjacent to the input end of the mixing channel.
19. The device according to any of Embodiments 1-18, wherein a container outlet cap is configured for selective sealable engagement with the external ejection connector port, the container outlet cap having an outlet cap wall terminating distally in an outlet cap base defining an outlet cap base surface, the outlet cap base surface being substantially planar and the outlet cap wall defining an outlet cap perimeter such that the device is capable of standing vertically on the container outlet cap.
20. The device according to any of Embodiments 1-19, wherein:
  the first constituent is substantially in one of powder form or liquid form; and
  the second constituent is substantially in liquid form.
21. A method of employing a solution delivery device as defined in any of Embodiments 1-20, the method comprising the steps of:
  a. filling the predetermined quantity of the first constituent within the internal cavity of the container component;
  b. positioning the plug component in the container component in the first operational mode of the device wherein the plug distal surface is spaced from the first constituent;
  c. acting on the first constituent with the device in the first operational mode;
  d. shifting the plug component to the second operational mode of the device wherein the plug component is fully seated within the container component and the plug distal surface is substantially adjacent to the first constituent; and
  e. flowing the second constituent through an internal flow path formed within the plug component and into the internal cavity of the container component so as to contact the first constituent;
  whereby the first and second constituents are sufficiently mixed in forming the delivery solution without the need for a separate mixing, shaking, reconstituting, or priming step.
22. The method according to Embodiment 21, wherein the step of shifting the plug component to the second operational mode comprises snapping the plug component within the container component.
23. The method according to Embodiment 21 or Embodiment 22, wherein the step of flowing the second constituent further comprises activating an injector wherein the device is operably installed.
24. A solution delivery device according to any of Embodiments 1-20 in combination with an injector.
25. The combination according to Embodiment 24, wherein the device is slidably installed within a housing of the injector.
26. The combination according to Embodiment 24 or Embodiment 25, further comprising one of a membrane or a plug temporarily sealing the external inlet connector port of the device.
27. The combination according to any one of Embodiments 24-26, wherein a reservoir is engaged with the external inlet connector port of the plug component, the reservoir containing the second constituent.
28. The combination according to Embodiment 27, wherein a plunger is operable within the reservoir to act on the second constituent, the plunger being biased distally by a plunger spring.
29. The combination according to Embodiment 27 or Embodiment 28, wherein the device, the reservoir, the membrane or the plug, and a shielded cannula assembly together comprise an injector sub-assembly slidably installed within the housing, the injector sub-assembly being biased distally by an assembly spring anchored against a proximal housing cap engaged with the housing, whereby axial movement of the injector sub-assembly against the assembly spring as when the injector is to be activated by pushing proximally on the shielded cannula assembly compresses the plunger spring and shifts the plunger distally relative to the injector sub-assembly and particularly the reservoir, the membrane or plug being configured to fail upon proximal movement of the injector sub-assembly and distal movement of the plunger under the increased force of the plunger spring, whereby the second constituent stored in the reservoir is freed and forced to flow out of the reservoir and through the external inlet connector port of the plug component into the container component and there mix with the first constituent housed within the internal cavity of the container component to form the delivery solution then expelled through a cannula of the shielded cannula assembly.
30. The device, method, or combination according to any of Embodiments 1-29 immediately above in further combination with one or more features or aspects according to any of Embodiments 1-348 set forth further above.

EXAMPLES

The following non-limiting examples are provided for illustrative purposes only in order to facilitate a more complete understanding of the disclosed subject matter. These examples should not be construed to limit any of the embodiments described in the present specification, including those pertaining to a solution delivery device, kits comprising a solution delivery device, and/or methods and uses for forming or using a solution delivery device according to aspects of the present invention.

Example 1

Arthritis Drug Self-Injection

This example demonstrates the use of a solution delivery device according to aspects of the present invention in the treatment of symptoms associated with rheumatoid arthritis.

A 56-year-old female suffers chronically from joint pain and other symptoms associated with the onset of rheumatoid arthritis. The prescribed treatment is weekly 50 mg or 1 ml (50 mg/ml) self-injection of the TNF-blocker etanercept sold under the trademark Enbrel®. The patient has an auto-refill prescription of the drug from her rheumatologist, such that a shipment of twelve doses arrives at her house on a roughly quarterly basis. Each of the twelve doses comprises a pre-filled solution delivery device containing the required dosage of etanercept in powder form, the device having a pre-installed, covered cannula at one end. A pre-filled syringe also included for each of the twelve doses contains the required amount of diluent to reconstitute the lyophilized etanercept. To self-administer the arthritis drug, the patient simply connects the pre-filled syringe to the delivery device, removes the cap from the injection end to expose the cannula, inserts the cannula into the skin, typically in the abdomen or thigh, and administers the subcutaneous drug injection by fully advancing the syringe plunger, which results in rapid reconstitution and delivery of the etanercept dose. The cannula is then withdrawn from the injection site and the entire device is disposed of in a sharps or other such biohazard container.

Example 2

Co-Administration of Cancer Drugs

This example demonstrates the use of three solution delivery devices in series according to aspects of the present invention in the co-administration of multiple anti-cancer drugs in treatment.

A 69-year-old male suffering from pancreatic cancer is undergoing a bi-weekly chemotherapy regimen of multiple anti-cancer drugs. The patient has a port installed, such that the drugs are co-administered through a connected I.V. line at a nominal rate of 100 mg/ml/day continuous infusion. A tumor-penetrating peptide, iRGD (CRGDK/RGPD/EC), is co-administered to increase vascular and tissue permeability in a tumor-specific and neuropilin-1-dependent manner, allowing the co-administered drugs to penetrate into extravascular tumor tissue more readily. Importantly, this effect did not require the anti-cancer drugs to be chemically conjugated to the peptide. Systemic injection with iRGD thus improving the therapeutic index of anti-cancer drugs of various compositions including a small molecule (doxorubicin), nanoparticles (nab-paclitaxel and doxorubicin liposomes), and a monoclonal antibody (trastuzumab), co-administration of iRGD enhances the efficacy of the anti-cancer drugs while reducing their side effects and so was prescribed by the patient's oncologist. Accordingly, first and second delivery devices containing the selected two anti-cancer drugs in powder form are connected in series with a third delivery device containing the iRGD also in powder form, with the last or most distal of the devices connected to the I.V. line luer connector leading to the port. A pumped diluent source is connected to the first or most proximal delivery device and operated to one-by-one reconstitute, the upstream reconstituted drug or peptide then serving to reconstitute or put in solution each subsequent powder, and then ultimately co-administer the anti-cancer drugs and peptide through the patient's port.

Example 3

Self-Injection of Liquid Aspirin

This example demonstrates the use of a solution delivery device according to aspects of the present invention in the self-administration of liquid, injectable aspirin in response to cardiovascular symptoms.

An injector is configured with a solution delivery device containing a lyophilized mixture of aspirin and trehalose (Lyo A/T) and connected in series with a pre-filled reservoir having a spring-biased plunger together delivering a nominal 5 ml dosage. The Lyo A/T is indicated for use in providing anti-inflammatory and analgesic effects known in non-steroidal anti-inflammatory drugs (NSAID) such as aspirin, with the trehalose working in conjunction with the aspirin to inhibit apoptosis while maintaining the anti-inflammatory effect. A 55-year-old male experiencing the onset of cardiovascular symptoms potentially indicative of a heart attack or a severe migraine employs the injector to, in a single step through activation of the injector as by jabbing himself in the thigh, reconstitute and administer the Lyo A/T and thereby receive temporary relief from his symptoms until further medical treatment can be administered as needed.

Example 4

In Field Neurotoxin Treatment

This example demonstrates the use of a solution delivery device according to aspects of the present invention in the in field-administration of atropine in the treatment of neurotoxin exposure.

A military dispatch deployed in the Middle East was subjected to a chemical weapons attack, with many soldiers exposed to the deadly neurotoxic agent sarin and requiring immediate treatment. Injectors carried in the field by the unit configured to each nominally deliver 2 mg of atropine by intramuscular injection, the atropine competing with ACh for the muscuranic ACh receptors and thus helping to protect accumulation of excess ACh during nerve agent poisoning and thereby reverse its effect, were employed to quickly reconstitute and administer the atropine and save the lives of the affected soldiers. Beyond the initial, immediate, life-saving injections, further injections were similarly administered to maintain and stabilize the health of the soldiers, each such dosage being conveniently self-administered or administered by generally untrained or non-medical personnel using the injectors configured with a solution delivery device containing the lyophilized atropine.

Example 5

Antivenom Self-Injection

This example demonstrates the use of a solution delivery device according to aspects of the present invention in the self-administration of an antivenom after a snake bite.

A 22-year-old female was alone on a hike in the woods when a rattlesnake struck and bit her in the left calf as she unexpectedly came upon the snake while stepping over a log in the trail. She retreated from the vicinity of the snake and took a snake bite injector from her backpack. The injector including a solution delivery device containing nominally 0.2 ml of freeze-dried polyvalent antivenom, more particularly crotalidae polyvalent immune fab (ovine) snake antivenom produced and sold under the CroFab® trademark, was immediately jabbed by the hiker into her left calf to rapidly reconstitute and administer the antivenom and thereby substantially combat the venom, as by binding to and neutralizing the venom, and thereby alleviate symptoms and prevent further harm from the bite until full medical attention could be provided, the antivenom remaining effective even though the hiker had purchased the injector nearly two years prior due to the relatively long shelf-life associated with lyophilized or freeze-dried drugs and other such agents.

Example 6

Treatment of an Opioid Drug Overdose

This example demonstrates the use of a solution delivery device according to aspects of the present invention in the treatment of an opioid drug overdose.

A mother came into her teenage son's bedroom to find him unconscious on the floor. With a glance at an open and empty bottle of her prescription pain medicine Vicodin® nearby, her worst fears were realized—a suicide attempt. She ran to the kitchen and retrieved an injector configured with a solution delivery device containing 2 mg of naloxone hydrochloride as sold under the trademark Evzio®, returned to her son, and jabbed the injector into his abdomen to rapidly reconstitute the powder naloxone and deliver the drug to her son subcutaneously through the injector needle. Though not immediately conscious, his heart rate and breathing noticeably increased from the dangerous levels they had dropped to and he generally was more stable. The mother had a second injector on hand, knowing that could administer a further 2 mg dose of naloxone within 2 or 3 minutes as needed, and up to 10 mg total, and she then called 911 and monitored her son's vitals closely until trained medical assistance arrived. In the end, her son survived thanks particularly to the early and substantially fail-safe administration of naloxone made possible by an on-hand injector.

Example 7

Treatment of Hypoglycemia by Self-Injection

This example demonstrates the use of a solution delivery device according to aspects of the present invention in the self-administration of glucose in a case of hypoglycemia.

A 45-year-old female with diabetes was restless in the night and, being hot and hungry, went down to the kitchen for a snack. Not finding anything appealing in the refrigerator and feeling weak, she sat down on the couch. Soon she was laying on the couch and feeling increasingly weak and sweaty and began to suspect that she was having a "diabetic crash," or was suffering from hypoglycemia. Recalling that she had taken an insulin injection before going to bed and that her appetite had not been very good the day before and so fearing that her blood sugar was going far too low and that she was on the border of "insulin shock," she fortunately was able to reach for a glucose injector on the end table near the couch and jab it into her thigh to self-administer a life-saving nominal dose of 5 mg of a-glucopyranose crystallized from water solution as contained in powder form in the solution delivery device installed in the injector. The injected glucose began to increase her blood sugar levels back toward the acceptable preprandial blood glucose range of 4.0 to 6.0 mmol/L (72 to 108 mg/dl), as confirmed by a subsequent in-home glucose test. She was then able to regulate and manage her diabetes and bring her blood sugar back under control through diet and medication, avoiding the adverse and potentially fatal effects of unchecked hypoglycemia.

Example 8

Co-Injection of Drugs in Treatment of Multiple Sclerosis

This example demonstrates the use of two solution delivery devices in series according to aspects of the present invention in the co-injection of drugs in the treatment of multiple sclerosis.

A 36-year-old female with multiple sclerosis undergoes a routine regimen in disease management including subcutaneous or intramuscular interferon beta b injections, which balances the expression of pro- and anti-inflammatory agents in the brain and thereby reduces the number of inflammatory cells that cross the blood-brain barrier. Since interferon beta b is known to cause skin reactions at the injection site immediately or over time that may include cutaneous necrosis, a preventative antidote is to be co-injected. Accordingly, first and second delivery devices are provided and connected in series, the first such device closest to the cannula containing the interferon beta b in powder form, alone or in combination with human serum albumin, and second such device upstream of the first and to which the diluent delivery syringe is connected containing the skin reaction preventative antidote. Activation of the syringe plunger forces the diluent such as sterile water for injection (WFI) into the second solution container device so as to reconstitute the antidote, which reconstituted composition then passes into the first delivery device so as to reconstitute or solubilize the interferon beta b, thereby rapidly and conveniently reconstituting and co-injecting the primary MS drug along with an antidote aimed at preventing or reducing its most common adverse side effect of skin irritation potentially leading to necrosis if not addressed.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular apparatus, methodology, configuration, size, shape, material of construction, protocol, etc., described herein, but may include any such technology now known or later developed in any combination without departing from the spirit and scope of the specification. As such, various modifications or changes to or alternative configurations of the disclosed subject matter can be made in accordance with the teachings herein without departing from the spirit and scope of the present specification. The drawings, whether or not identified as schematics, are not to be taken to scale or to purport any particular dimensions unless expressly so indicated; rather, the drawings convey structure and concepts as relating to the present specification and no more unless stated otherwise. Lastly, the terminology used herein is for the purpose of describing particular embodiments only, and is not intended to limit the scope of the present invention. Accordingly, the present invention is not limited to that precisely as shown and described.

Certain embodiments of the present invention are described herein, including the best mode known to the inventor(s) for carrying out the invention. Of course, variations on these described embodiments will become apparent to those of ordinary skill in the art upon reading the foregoing description. The inventor expects skilled artisans to employ such variations as appropriate, and the inventor intends for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the present invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using "consisting of" or "consisting essentially of" language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The invention claimed is:

1. A solution delivery device comprising:
    a container component having a proximally-extending engagement wall and an internal cavity with a size selected to contain a predetermined quantity of a first constituent, wherein the engagement wall terminates proximally in a radially-inwardly projecting engagement lip, the container component further having a distal end with an external ejection connector port;
    a plug component configured for selective engagement with the container component in at least first and second operational modes, the plug component having a proximal end, a distal end, and a side wall having an outer surface disposed between the ends and formed with an outwardly-opening engagement groove, the side wall and distal end together defining a plug periphery, the plug component further having an external inlet connector port substantially at the proximal end and an internal flow path from the inlet connector port to a plug outlet port intersecting the plug periphery, the plug component being formed on the distal end with a plug distal surface; and
    an elongated channel wall installed within the internal cavity of the container component to form an elongated mixing channel, the channel wall having a wall top surface and being located within the container component such that the mixing channel has a substantially closed bottom and an open top adjacent the wall top surface, the mixing channel having an input end in fluid communication with the plug outlet port and an output end in fluid communication with the ejection connector port;
    wherein in the first operational mode the plug component is partially inserted within the container component such that the plug distal surface is spaced from the wall top surface so as to facilitate the fluid communication between the internal cavity of the container component, and particularly the mixing channel, and the surrounding atmosphere;
    wherein the wall top surface of the elongated channel wall is located within the container component facing the plug component so that when the plug component and the container component are fully assembled together in the second operational mode as by the engagement lip of the container component engaging the engagement groove of the plug component, the plug distal surface contacts the wall top surface and substantially closes the top of the elongated mixing channel so that the only access to the first constituent is provided by the input and output ends of the mixing channel; and
    wherein forcing a second constituent through the inlet connector port with the device in the second operational mode causes the second constituent to flow through the internal flow path of the plug component and out the plug outlet port and into the input end of the mixing channel so as to mix with the first constituent, whereby the first and second constituents are sufficiently mixed as together traversing the mixing channel from the inlet end to the outlet end and then out through the ejection connector port as a delivery solution without the need for a separate mixing, shaking, reconstituting, or priming step.

2. The device according to claim 1, wherein the plug component further comprises a radially-outwardly projecting retention lip distal of the engagement groove, wherein in the first operational mode with the plug component partially inserted within the container component the retention lip seats on the engagement lip of the container component, whereby the plug component is suspended within the container component.

3. The device according to claim 2, wherein the engagement groove is formed between a proximal radially-outwardly extending plug flange and the radially-outwardly projecting retention lip.

4. The device according to claim 1, wherein the container component further comprises a base wall with an inner surface and an interconnecting groove formed in the inner surface of the base wall so as to be in fluid communication with the input end of the mixing channel.

5. The device according to claim 4, wherein the interconnecting groove is substantially lengthwise along the container component base wall and of sufficient length to be in fluid communication with the plug outlet port upon assembly of the plug component within the container component in the second operational mode, whereby the mixing channel provides an indirect flow path between the plug outlet port and the ejection connector port.

6. The device according to claim 4, wherein the container component further comprises a distribution groove formed in one of the inner surface of the base wall or the outer surface of the side wall so as to be in selective fluid communication with the interconnecting groove.

7. The device according to claim 6, wherein the distribution groove is formed as an upwardly-opening step in the inner surface of the base wall, such that the base wall has a stepped inner bore.

8. The device according to claim 1, wherein the outer surface of the side wall of the plug component is formed having a plug seating portion configured to seat against a container seating portion of an inner surface of a base wall of the container component distal of the engagement wall upon assembly of the plug component within the container component in the second operational mode.

9. The device according to claim 8, wherein the plug seating portion and the container seating portion are configured for a net-fit engagement.

10. The device according to claim 1, wherein a base wall of the container component terminates proximally in a substantially radially-outwardly extending container flange having the proximally-extending engagement wall.

11. The device according to claim 10, wherein:
the plug component is formed having a stepped side wall defined by a distally-facing shoulder separating a relatively larger diameter proximal plug engagement portion from a relatively smaller diameter distal plug seating portion; and
the distance from the engagement lip to the container flange of the container component is substantially equivalent to the distance from the engagement groove to the shoulder of the plug component, whereby engagement of the engagement lip within the engagement groove upon assembly of the plug component within the container component in the second operational mode substantially positions the shoulder of the plug component adjacent to the container flange of the container component.

12. The device according to claim 11, wherein the distance from the container flange to the wall top surface of the elongated channel wall installed within the internal cavity of the container component is substantially equivalent to the distance from the shoulder to the distal end of the plug component, whereby assembly of the plug component within the container component in the second operational mode such that the engagement lip of the container component is engaged within the engagement groove of the plug component and the shoulder of the plug component is positioned adjacent to the container flange of the container component causes the plug distal surface of the plug component to substantially seat against the wall top surface of the elongated channel wall of the container component to substantially close the top of the mixing channel and further causes the plug seating portion of the plug component to seat within a container seating portion of the container component to substantially seal the mixing channel other than the input end in fluid communication with the plug outlet port.

13. The device according to claim 10, wherein at least one container vent hole is formed within the container flange radially outwardly of the base wall, whereby in the first operational mode with the plug component partially inserted within the container component there is fluid communication between the inner cavity of the container component and the surrounding atmosphere at least through the at least one container vent hole.

14. The device according to claim 1, wherein the radially-inwardly projecting engagement lip is flexible and shifting the device to the second operational mode with the plug component fully assembled within the container component involves shifting the radially-inwardly projecting engagement lip proximally relative to the radially-outwardly projecting retention lip so as to pass thereover and seat proximally thereof and adjacent thereto.

15. The device according to claim 1, wherein the radially-inwardly projecting engagement lip is formed on a flexible leg defining a portion of the engagement wall of the container component.

16. The device according to claim 15, wherein the flexible leg is defined by a section of the engagement wall bounded by offset lengthwise notches so as to function as a living hinge.

17. The device according to claim 1, wherein:
the plug component is formed at the plug distal end with a distally-opening insert receiving cavity in fluid communication with the internal flow path; and
a plug insert is received within the insert receiving cavity, the plug insert formed on a top surface with at least one horizontal groove so as to be in fluid communication with the flow path and on an outer surface with at least one vertical groove intersecting and in fluid communication with the horizontal groove, the vertical groove further intersecting a distally-facing bottom surface of the plug insert, the vertical groove defining the plug outlet port and the lower surface defining the plug distal surface.

18. The device according to claim 1, wherein:
the container component is formed with a container indexing surface; and
the plug component is formed with a plug indexing surface configured to selectively engage the container indexing surface as the plug component is seated within the container component, whereby in the second operational mode the plug outlet port is positioned substantially adjacent to the input end of the mixing channel.

19. The device according to claim 1, wherein a container outlet cap is configured for selective sealable engagement with the external ejection connector port, the container outlet cap having an outlet cap wall terminating distally in an outlet cap base defining an outlet cap base surface, the outlet cap base surface being substantially planar and the outlet cap wall defining an outlet cap perimeter such that the device is capable of standing vertically on the container outlet cap.

20. The device according to claim 1, wherein:
the first constituent is substantially in one of powder form or liquid form; and
the second constituent is substantially in liquid form.

21. A method of employing a solution delivery device as defined in claim 1, the method comprising the steps of:
a. filling the predetermined quantity of the first constituent within the internal cavity of the container component;

b. positioning the plug component in the container component in the first operational mode of the device wherein the plug distal surface is spaced from the first constituent;
c. acting on the first constituent with the device in the first operational mode;
d. shifting the plug component to the second operational mode of the device wherein the plug component is fully seated within the container component and the plug distal surface is substantially adjacent to the first constituent; and
e. flowing the second constituent through an internal flow path formed within the plug component and into the internal cavity of the container component so as to contact the first constituent;
whereby the first and second constituents are sufficiently mixed in forming the delivery solution without the need for a separate mixing, shaking, reconstituting, or priming step.

22. The method according to claim 21, wherein the step of shifting the plug component to the second operational mode comprises snapping the plug component within the container component.

23. The method according to claim 21, wherein the step of flowing the second constituent further comprises activating an injector wherein the device is operably installed.

24. A solution delivery device according to claim 1 in combination with an injector.

25. The combination according to claim 24, wherein the device is slidably installed within a housing of the injector.

26. The combination according to claim 24, further comprising one of a membrane or a plug temporarily sealing the external inlet connector port of the device.

27. The combination according to claim 26, wherein a reservoir is engaged with the external inlet connector port of the plug component, the reservoir containing the second constituent.

28. The combination according to claim 27, wherein a plunger is operable within the reservoir to act on the second constituent, the plunger being biased distally by a plunger spring.

29. The combination according to claim 27, wherein the device, the reservoir, the membrane or the plug, and a shielded cannula assembly together comprise an injector sub-assembly slidably installed within the housing, the injector sub-assembly being biased distally by an assembly spring anchored against a proximal housing cap engaged with the housing, whereby axial movement of the injector sub-assembly against the assembly spring as when the injector is to be activated by pushing proximally on the shielded cannula assembly compresses the plunger spring and shifts the plunger distally relative to the injector sub-assembly and particularly the reservoir, the membrane or plug being configured to fail upon proximal movement of the injector sub-assembly and distal movement of the plunger under the increased force of the plunger spring, whereby the second constituent stored in the reservoir is freed and forced to flow out of the reservoir and through the external inlet connector port of the plug component into the container component and there mix with the first constituent housed within the internal cavity of the container component to form the delivery solution then expelled through a cannula of the shielded cannula assembly.

* * * * *